US007071205B2

(12) United States Patent
Zhi et al.

(10) Patent No.: US 7,071,205 B2
(45) Date of Patent: Jul. 4, 2006

(54) 5-CYCLOALKENYL 5H-CHROMENO[3,4-F]QUINOLINE DERIVATIVES AS SELECTIVE PROGESTERONE RECEPTOR MODULATOR COMPOUNDS

(75) Inventors: Lin Zhi, San Diego, CA (US); Cornelis Arjan Van Oeveren, Carlsbad, CA (US); Bijan Pedram, San Diego, CA (US); Donald S. Karanewsky, Escondido, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 0 days.

(21) Appl. No.: 10/684,229

(22) Filed: Oct. 10, 2003

(65) Prior Publication Data
US 2004/0152718 A1 Aug. 5, 2004

Related U.S. Application Data

(60) Provisional application No. 60/417,975, filed on Oct. 11, 2002.

(51) Int. Cl.
A61K 31/4741 (2006.01)
C07D 491/02 (2006.01)

(52) U.S. Cl. ..................................... 514/285; 546/62
(58) Field of Classification Search ................ 514/285; 546/62
See application file for complete search history.

(56) References Cited

U.S. PATENT DOCUMENTS

| 5,506,102 A | 4/1996 | McDonnell et al. ............ 435/6 |
| 5,688,808 A | 11/1997 | Jones et al. .................. 514/285 |
| 5,688,810 A | 11/1997 | Jones et al. .................. 514/311 |
| 5,693,646 A | 12/1997 | Jones et al. |
| 5,693,647 A | 12/1997 | Jones et al. |
| 5,696,127 A | 12/1997 | Jones et al. |
| 5,696,130 A | 12/1997 | Jones et al. .................. 514/291 |
| 5,696,133 A | 12/1997 | Jones et al. .................. 514/314 |
| 5,808,139 A | 9/1998 | Pathirana et al. ............ 560/138 |
| 5,994,544 A | 11/1999 | Jones et al. .................. 546/62 |
| 6,093,821 A | 7/2000 | Jones et al. .................. 544/333 |
| 6,093,825 A | 7/2000 | Jones et al. .................. 546/62 |
| 6,093,826 A | 7/2000 | Edwards et al. .............. 546/62 |
| 6,121,450 A | 9/2000 | Jones et al. .................. 546/81 |
| 6,172,241 B1 | 1/2001 | Edwards et al. ............. 549/280 |
| 6,268,497 B1 | 7/2001 | Edwards et al. .............. 546/62 |
| 6,306,851 B1 | 10/2001 | Santilli et al. ............. 514/230.5 |
| 6,319,912 B1 | 11/2001 | Grubb et al. ................ 514/171 |
| 6,329,416 B1 | 12/2001 | Grubb et al. ................ 514/415 |
| 6,339,098 B1 | 1/2002 | Collins et al. .............. 514/373 |
| 6,355,648 B1 | 3/2002 | Fensome et al. ............. 514/275 |
| 6,358,947 B1 | 3/2002 | Zhi et al. .................. 514/229.5 |
| 6,358,948 B1 | 3/2002 | Zhang et al. ............... 514/230.5 |
| 6,369,056 B1 | 4/2002 | Zhang et al. ............... 514/230.5 |
| 6,380,178 B1 | 4/2002 | Grubb et al. ................ 514/171 |
| 6,380,207 B1 | 4/2002 | Coghlan et al. ............. 514/285 |
| 6,380,235 B1 | 4/2002 | Zhang et al. ................ 514/395 |
| 6,391,907 B1 | 5/2002 | Fensome et al. ............. 514/409 |
| 6,399,593 B1 | 6/2002 | Grubb et al. ................ 514/171 |
| 6,407,101 B1 | 6/2002 | Collins et al. ............. 514/230.5 |
| 6,417,214 B1 | 7/2002 | Ullrich et al. .............. 514/378 |
| 6,436,929 B1 | 8/2002 | Zhang et al. .............. 514/230.5 |
| 6,441,019 B1 | 8/2002 | Santilli et al. .............. 514/409 |
| 6,444,668 B1 | 9/2002 | Grubb et al. .............. 514/230.5 |
| 6,448,405 B1 | 9/2002 | Jones et al. .................... 546/62 |
| 6,462,032 B1 | 10/2002 | Grubb et al. ................ 514/171 |
| 6,498,154 B1 | 12/2002 | Grubb et al. ................ 514/171 |
| 6,503,939 B1 | 1/2003 | Grubb et al. ................ 514/415 |
| 6,506,766 B1 | 1/2003 | Coghlan et al. ............. 514/285 |
| 6,509,334 B1 | 1/2003 | Zhang et al. .............. 514/230.5 |
| 6,521,657 B1 | 2/2003 | Fensome et al. ............. 514/414 |
| 6,544,970 B1 | 4/2003 | Grubb et al. ................ 514/171 |
| 6,566,358 B1 | 5/2003 | Zhi et al. .................. 514/230.5 |
| 6,566,372 B1 | 5/2003 | West et al. .................. 514/312 |
| 6,583,145 B1 | 6/2003 | Fensome et al. ............. 514/256 |
| 6,608,068 B1 | 8/2003 | Fensome et al. ............. 514/256 |
| 6,693,103 B1 | 2/2004 | Zhang et al. ................ 514/256 |
| 6,696,459 B1 | 2/2004 | Jones et al. .................. 514/285 |
| 6,713,478 B1 | 3/2004 | Zhang et al. .............. 514/230.5 |
| 6,759,408 B1 | 7/2004 | Grubb et al. .............. 514/230.5 |
| 6,794,373 B1 | 9/2004 | Grubb et al. ................ 514/171 |
| 6,835,744 B1 | 12/2004 | Ullrich et al. .............. 514/409 |
| 6,841,568 B1 | 1/2005 | Fensome et al. ............. 514/415 |
| 2003/0216388 A1 | 11/2003 | Zhang et al. .............. 514/230.5 |
| 2003/0220388 A1 | 11/2003 | Fensome et al. ............. 514/414 |
| 2003/0225109 A1 | 12/2003 | Fensome et al. ............. 514/256 |
| 2004/0147530 A1 | 7/2004 | Zhi et al. .................... 514/256 |
| 2004/0152717 A1 | 8/2004 | Zhi et al. .................... 514/285 |
| 2004/0186101 A1 | 9/2004 | Zhang et al. .............. 514/230.5 |

FOREIGN PATENT DOCUMENTS

WO 9619458 6/1996

(Continued)

OTHER PUBLICATIONS

Berger, T. S., et al., Interaction of Glucocorticoid Analogues with the Human Glucocorticoid Receptor. J. Steroid Biochem. Mol. Bio. 1992, 41, 733-738.

Pathirana, C., et al., Nonsteroidal Human Progesterone Receptor Modulators from the Marine Alga Cymopolia Babata. Mol. Pharm. 1995, 47, 630-635.

International Search Report for Corresponding Application PCT/US03/24419 filed Aug. 4, 2003 (dated Jan. 29, 2004).

(Continued)

Primary Examiner—Charanjit S. Aulakh
(74) Attorney, Agent, or Firm—Fish & Richardson P.C.; Stephanie Seidman; Frank J. Miskiel

(57) ABSTRACT

The present invention is directed to compounds, pharmaceutical compositions, and methods for modulating processes mediated by Progesterone Receptor. Also provided are methods of making such compounds and pharmaceutical compositions.

29 Claims, No Drawings

FOREIGN PATENT DOCUMENTS

| | | |
|---|---|---|
| WO | WO 99/41256 A1 | 8/1999 |
| WO | 0066103 | 11/2000 |
| WO | 0066163 | 11/2000 |
| WO | 0066164 | 11/2000 |
| WO | 0066165 | 11/2000 |
| WO | 0066166 | 11/2000 |
| WO | 0066167 | 11/2000 |
| WO | 0066168 | 11/2000 |
| WO | 0066225 | 11/2000 |
| WO | 0066554 | 11/2000 |
| WO | 0066555 | 11/2000 |
| WO | 0066556 | 11/2000 |
| WO | 0066560 | 11/2000 |
| WO | 0066564 | 11/2000 |
| WO | 0066570 | 11/2000 |
| WO | 0066571 | 11/2000 |
| WO | 0066574 | 11/2000 |
| WO | 0066581 | 11/2000 |
| WO | 0066590 | 11/2000 |
| WO | 0066591 | 11/2000 |
| WO | 0066592 | 11/2000 |
| WO | 0116108 | 3/2001 |
| WO | WO 02/02565 | 1/2002 |
| WO | WO 99/41257 A1 | 4/2002 |
| WO | 2004033459 | 4/2004 |
| WO | 2004033460 | 4/2004 |
| WO | 2004033461 | 4/2004 |

OTHER PUBLICATIONS

Tegley, Christopher et al., "5-Benzylidene 1,2-Dihydrochromeno[3,4-f]quinolines, A Novel Class of Nonsteroidal Human Progesterone Receptor Agonists", Journal of Medicinal Chemistry, American Chemical Society. Washington, US, vol. 41, No. 3, 1998, pp. 4354-4359.

Zhi, Lin et al., "5-Aryl-1,2-dihydrochromeno[3,4-f]quinolines: A Novel Class of Nonsteroidal Human Progesterone Receptor Agonists", *Journal of Medicinal Chemistry*, American Chemical Society. Washington, US, vol. 41, No. 3, 1998, pp. 291-302.

Zhi, L. et al., "5-Alkyl 1,2-Dihydrochromeno[3-4f]quinolines: A Novel Class of Nonsteroidal Progesterone Receptor Modulators", *Bioorganic & Medicinal Chemistry Letters*, Oxford GB, vol. 8, No. 23, Dec. 1, 1998, pp. 3365-3370.

Zhi, Lin et al., "Novel Class of Non-Steroidal Progesterone Receptor Antagonist", *Expert Opinion on Therapeutic Patents*, Ashley Publications, GB, vol. 9, No. 6, 1999, pp. 695-700.

Clemm et al., "Definition of the critical cellular components which distinguish between hormone and antihormone activated progesterone receptor," Journal of Steroid Biochemistry and Molecular Biology 53(1-6):487-495. (1995).

Crombie et al., "Anti-progesterone effects on maternal recognition and behaviour imprinted during first pregnancy in mice," Journal of Endocrinology 147(2):331-337. (1995).

Edwards et al., "5-Aryl-1,2-dihydro-5H-chromeno[3,4-f]quinolines as potent, orally active, nonsteroidal progesterone receptor agonists: the effect of D-ring substituents," Journal of Medicinal Chemistry. 41(3):303-310 (1998).

Edwards et al., "Preparation, resolution, and biological evaluation of 5-aryl-1, 2-dihydro-5H-chromeno[3,4-f]quinolines: potent, orally active, nonsteroidal progesterone receptor agonists," Journal of Medicinal Chemistry 41(15):2779-2785 (1998).

Hamann et al., "Nonsteroidal progesterone receptor antagonists based on a conformationally-restricted subseries of 6-aryl-1,2-dihyrdo-2,2,4-trimethylquinolines," Bioorganic & Medicinal Chemistry Letters 8(19):2731-2736 (1998).

Mais et al., "Specific interactions of progestins and anti-progestins with progesterone antibodies, plasma binding proteins and the human recombinant receptor," Journal of Steroid Biochemistry and Molecular Biology 54(1-2):63-69. (1995).

McDonnell, D. P. and M.E. Goldman, "RU486 exerts antiestrogenic activities through a novel progesterone receptor A form-mediated mechanism," The Journal of Biological Chemistry 269(16):11945-11949. (1994).

McDonnell et al., "Definition of the cellular mechanisms which distinguish between hormone and antihormone activated steroid receptors," Seminars in Cancer Biology, 5(5):327-336 (1994).

McDonnell et al., "The human progesterone receptor A-form functions as a transcriptional modulator of mineralocorticoid receptor transcriptional activity," Journal of Steroid Biochemistry and Molecular Biology 48(5-6):425-432. (1994).

Miner, J. N. and C.M. Tyree, "Drug discovery and the intracellular receptor family," Vitamins and Hormones. 62:253-280. (2001).

Parandoosh et al., "Progesterone and oestrogen receptors in the decidualized mouse uterus and effects of different types of anti-progesterone treatment," Journal of Reproduction and Fertility 105(2):215-220. (1995).

Rosen et al., "Intracellular receptors and signal transducers and activators of transcription superfamilies—novel targets for small-molecule drug discovery," Journal of Medicinal Chemistry 38(25):4855-4874 (1995).

Santiso-Mere, D. and D.P. McDonnell, "Applied nuclear receptor research in the drug discovery process," Chimica Oggi. 12(5-6):29-36. (1994).

Taylor et al., "Activity of progesterone and anti-progestins in a rat mammary primary cell culture system," Journal of Steroid Biochemistry and Molecular Biology 58(1):117-121 (1996).

Vegeto et al., "Human progesterone receptor A form is a cell- and promoter-specific repressor of human progesterone receptor B function," Molecular Endocrinology. 7(10):1244-1255. (1993).

Wagner et al., "The novel progesterone receptor antagonists RTI 3021-012 and RTI 3021-022 exhibit complex glucocorticoid receptor antagonist activities: Implications for the development of dissociated antiprogestins," Endocrinology 140(3):1449-1458 (1999).

Wen et al., "The A and B isoforms of the human progesterone receptor operate through distinct signaling pathways within target cells," Molecular and Cellular Biology 14(12):8356-8364 (1994).

Zhang et al., "6-Aryl-1,4-dihydro-benzo[d][1,3]oxazin-2-ones: A Novel Class of Potent, Selective, and Orally Active Nonsteroidal Progesterone Receptor Antagonists," Journal of Medicinal Chemistry 45(20):4379-4382 (2002).

Zhang et al., "Synthesis and progesterone receptor antagonist activities of 6-aryl benzimidazolones and benzothiazolones," Bioorganic & Medicinal Chemistry Letters 11(20):2747-2750 (2001).

Zhi et al., "Development of progesterone receptor antagonists from 1,2-dihydrochromeno[3,4-f]quinoline agonist pharmacophore," Bioorganic & Medicinal Chemistry Letters. 13(12):2075-2078. (2003).

Zhi, et al. "Synthesis and Biological Activity of 5-Methylidine 1,2-Dihydrochromeno[3,4-f]quinoline Derivatives as Progesterone Receptor Modulators" Bioorganic & Medicinal Chemistry Letters 13:2071-2074 (2003).

Zhi et al., "5-Aryl-1,2,3,4-tetrahydrochromeno[3,4-f]quinolin-3-ones as a novel class of nonsteroidal progesterone receptor agonists: effect of A-ring modification," Journal of Medicinal Chemistry. 42(8):1466-1472 (1999).

Zhi et al., "5-Benzylidene-1,2-dihydrochromeno[3,4-f]quinolines as Selective Progesterone Receptor Modulators," Journal of Medicinal Chemistry 46(19):4104-4112 (2003).

Zhi et al., "Nonsteroidal progesterone receptor antagonists based on 6-thiophenehydroquinolines," Bioorganic & Medicinal Chemistry Letters. 10(5):415-418 (2000).

5-CYCLOALKENYL 5H-CHROMENO[3,4-F]QUINOLINE DERIVATIVES AS SELECTIVE PROGESTERONE RECEPTOR MODULATOR COMPOUNDS

RELATED APPLICATIONS

This application claims the benefit of priority of U.S. Provisional Application Ser. No. 60/417,975 filed Oct. 11, 2002, the entire disclosure of which is incorporated herein by reference.

FIELD OF THE INVENTION

This invention relates to nonsteroidal 5-cycloalkenyl 5H-chromeno[3,4-f]quinoline derivatives that may be modulators (i.e., agonists, partial agonists and antagonists) of progesterone receptors and to methods for the making and use of such compounds.

BACKGROUND OF THE INVENTION

Progesterone receptor (PR) modulators have been widely used in regulation of female reproduction systems and in treatment of female hormone dependent diseases. The effectiveness of known steroidal PR modulators is often tempered by their undesired side-effect profile, particularly during long-term administration. For example, the effectiveness of synthetic progestins, such as norgestrel, as female birth control agents must be weighed against the increased risk of breast cancer and heart disease. Similarly, the progesterone antagonist, mifepristone (RU486), if administered for chronic indications, such as uterine fibroids, endometriosis and certain hormone-dependent cancers, could lead to homeostatic imbalances in a patient due to its inherent cross-reactivity as a glucocorticoid receptor (GR) antagonist. Accordingly, identification of compounds that have good receptor-selectivity for PR over other steroid hormone receptors as well as good tissue-selectivity (e.g., selectivity for uterine tissue over breast tissue) would be of significant value in the improvement of women's health.

A group of nonsteroidal molecules, which contain a di- or tetra-hydroquinoline ring as core pharmacophore (U.S. Pat. Nos. 5,693,646; 5,693,647 and 5,696,127; PCT Int'l. Publication Nos. WO 99/41256 A1 and WO 99/41257 A1) have been described as steroid receptor modulator compounds.

The entire disclosures of the patents, publications and references referred to herein are incorporated by reference herein and are not admitted to be prior art.

SUMMARY OF THE INVENTION

The present invention is directed to compounds, pharmaceutical compositions, and methods for modulating processes mediated by Progesterone Receptor. More particularly, the invention relates to nonsteroidal compounds and compositions which may be high affinity, high specificity agonists, partial agonists (i.e., partial activators and/or tissue-specific activators) and/or antagonists for progesterone receptors. Also provided are methods of making such compounds and pharmaceutical compositions.

Compounds of the present invention may be represented by the formulae:

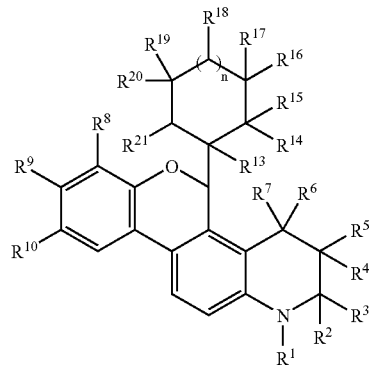

wherein:

$R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;

$R^2$ and $R^3$ each independently is selected from the group of hydrogen, $C_1$–$C_6$ alkyl, and $C_1$–$C_6$ haloalkyl; or $R^2$ and $R^3$ taken together form a cycloalkyl ring of from three to twelve carbons;

$R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or $R^5$ and $R^7$ taken together form a bond; or $R^6$ and $R^7$ taken together are selected from the group of methylidene, mono-substituted methylidene, di-substituted methylidene and carbonyl;

$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl, $C_2$–$C_8$ alkynyl;

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;

$R^{13}$ is hydrogen; or $R^{13}$ and $R^{14}$ taken together form a bond;

$R^{14}$ through $R^{20}$ each independently is selected from the group of hydrogen, F, Cl, Br, $OR^{11}$, $C_1$–$C_4$ alkyl, $C_1$–$C_4$ haloalkyl, and $C_1$–$C_4$ heteroalkyl; or $R^{14}$ and $R^{15}$ taken together are selected from the group of methylidene, carbonyl and thiocarbonyl; or $R^{16}$ and $R^{17}$ taken together are selected from the group of methylidene, mono-substituted methylidene, di-substituted methylidene, ethylidene, carbonyl and thiocarbonyl; or $R^{14}$ and $R^{16}$ taken together form a bond or "—O—" bridge; or $R^{16}$ and $R^{18}$ taken together form a bond when n is 1; or $R^{16}$ and $R^{19}$ taken together form a bond when n is 0;

$R^{21}$ is hydrogen; or $R^{21}$ and $R^{20}$ taken together form a bond;

n is 0, 1, 2, or 3;

and pharmaceutically acceptable salts and prodrugs thereof.

DEFINITIONS AND NOMENCLATURE

As used herein, the following terms are defined with the following meanings, unless explicitly stated otherwise. Furthermore, in an effort to maintain consistency in the naming of compounds of similar structure but differing substituents, the compounds described herein are named according to the following general guidelines. The numbering system for the location of substituents on such compounds is also provided.

A 5H-chromeno[3,4-f]quinoline is defined by the following structure:

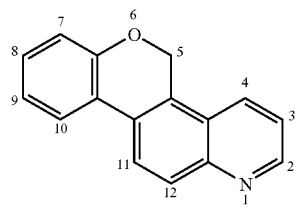

The term "alkyl," alone or in combination, refers to an optionally substituted straight-chain or branched-chain or cyclic-chain alkyl radical having from 1 to about 12 carbon atoms. The term also includes substituted straight-chain or branched-chain alkyl radicals having from 1 to about 6 carbon atoms as well as those having from 1 to about 4 carbon atoms. Examples of alkyl radicals include methyl, ethyl, n-propyl, isopropyl, cyclopropyl, n-butyl, isobutyl, sec-butyl, tert-butyl, tert-amyl, pentyl, hexyl, heptyl, octyl and the like.

The term "alkenyl," alone or in combination, refers to an optionally substituted straight-chain or branched-chain hydrocarbon radical having one or more carbon-carbon double-bonds and having from 2 to about 18 carbon atoms. The term also includes substituted straight-chain or branched-chain alkyl radicals having one or more carbon-carbon double bonds and having from 2 to about 6 carbon atoms as well as those having from 2 to about 4 carbon atoms. Examples of alkenyl radicals include ethenyl, propenyl, 1,3-butadienyl and the like.

"Methylidene," alone or in combination, refers to $=CH_2$ and may be optionally substituted.

"Allyl," alone or in combination, refers to $-CH_2-CH=CH_2$ and may be optionally substituted.

The term "alkynyl," alone or in combination, refers to an optionally substituted straight-chain or branched-chain hydrocarbon radical having one or more carbon-carbon triple-bonds and having from 2 to about 12 carbon atoms. The term also includes substituted straight-chain or branched-chain alkyl radicals having one or more carbon-carbon triple bonds and having from 2 to about 6 carbon atoms as well as those having from 2 to about 4 carbon atoms. Examples of alkynyl radicals include ethynyl, propynyl, butynyl and the like.

The term "heteroalkyl," "heteroalkenyl" and "heteroalkynyl" refer to alkyl, alkenyl and alkynyl radicals, respectively, as described above, in which one or more skeletal atoms are heteroatoms such as, for example, oxygen, nitrogen, sulfur or combinations thereof. The terms heteroalkyl, heteroalkenyl and heteroalkynyl include radicals in which 1 to about 6 skeletal atoms are oxygen, nitrogen, sulfur or combinations thereof, as well as those in which 1 to 4 skeletal atoms are oxygen, nitrogen, sulfur or combinations thereof and those in which 1 to 2 skeletal atoms are oxygen, nitrogen, sulfur or combinations thereof.

The term "aryl," alone or in combination, refers to an optionally substituted aromatic ring system. The term aryl includes monocyclic aromatic rings, polyaromatic rings and polycyclic aromatic ring systems containing from to six about twenty carbon atoms. The term aryl also includes monocyclic aromatic rings, polyaromatic rings and polycyclic ring systems containing from six to about 12 carbon atoms, as well as those containing from 6 to about 10 carbon atoms. The polyaromatic and polycyclic aromatic rings systems may contain from two to four rings. Examples of aryl radicals include, without limitation, phenyl, biphenyl, naphthyl and anthryl ring systems.

The term "heteroaryl" refers to an optionally substituted aromatic ring system containing from about five to about 20 skeletal ring atoms and having one or more heteroatoms such as, for example, oxygen, nitrogen and sulfur. The term heteroaryl also includes optionally substituted aromatic ring systems having from 5 to about 12 skeletal ring atoms, as well as those having from 5 to about 10 skeletal ring atoms. The term heteroaryl may include five- or six-membered heterocyclic rings, polycyclic heteroaromatic ring systems and polyheteroaromatic ring systems where the ring system has two, three or four rings. The terms heterocyclic, polycyclic heteroaromatic and polyheteroaromatic include ring systems containing optionally substituted heteroaromatic rings having more than one heteroatom as described above (e.g., a six membered ring with two nitrogens), including polyheterocyclic ring systems of from two to four rings. The term heteroaryl includes ring systems such as, for example, furanyl, benzofuranyl, chromenyl, pyridyl, pyrrolyl, indolyl, quinolinyl, N-alkyl pyrrolyl, pyridyl-N-oxide, pyrimidyl, pyrazinyl, imidazolyl, pyrazolyl, oxazolyl, benzothiophenyl, purinyl, indolizinyl, thienyl and the like.

The terms haloalkyl, haloalkenyl, haloalkynyl and haloalkoxy include alkyl, alkenyl, and alkynyl structures, as described above, that are substituted with one or more fluorines, chlorines, bromines or iodines, or with combinations thereof.

The terms cycloalkyl, aryl, arylalkyl, heteroaryl, alkyl, alkynyl, alkenyl, haloalkyl and heteroalkyl include optionally substituted cycloalkyl, aryl, arylalkyl, heteroaryl, alkyl, alkynyl, alkenyl, haloalkyl and heteroalkyl radicals.

The term "carbocycle" includes optionally substituted, saturated or unsaturated, three- to eight-membered cyclic structures in which all of the skeletal atoms are carbon.

The term "heterocycle" includes optionally substituted, saturated or unsaturated, three- to eight-membered cyclic structures in which one or more skeletal atoms is oxygen, nitrogen, sulfur, or combinations thereof.

The term "acyl" includes alkyl, aryl, heteroaryl, arylalkyl or heteroarylalkyl substituents attached to a compound via a carbonyl functionality (e.g., —CO-alkyl, —CO-aryl, —CO-arylalkyl or —CO-heteroarylalkyl, etc.).

The term "halogen" includes F, Cl, Br and I.

The term "mediate" means affect or influence, frequently indirectly or via some intervening action. Thus, for example, conditions mediated by a progesterone receptor are those in which a progesterone receptor plays a role. Progesterone receptors are known to play a role in conditions including, for example, infertility, contraception, pregnancy maintenance and termination, female hormone deficiency, female sexual dysfunction, dysfunctional uterine bleeding, endometriosis, mood disorder, osteoporosis, and hormone-dependent cancers.

The term "receptor-selectivity" refers to the conditions where a compound displays modulating activity towards one or more particular receptors (e.g., a progesterone receptors) while displaying substantially less or no cross-reactivity towards one or more different receptors (e.g., glucocorticoid receptors). Thus, for example, selective compounds of the present invention may display modulating activity towards progesterone receptors without displaying substantial cross-reactivity towards another steroid hormone receptors. Compounds may be selective for a single receptor, group of similar receptors or multiple receptors.

The term "tissue-selectivity" refers to compounds that display substantial modulating activity in one tissue (e.g., uterine tissue) while displaying lesser modulating activity in at least one other tissue (e.g., breast tissue). Thus, for example, tissue-selective compounds of the present invention may display substantial modulating activity in uterine and vaginal tissues with lesser modulating activity (partial agonistic or partial antagonistic) in breast tissues relative to the activities of the marketed steroidal progestins in all of the target tissues.

The term "modulate" means affect or influence, for example, the amount, degree or proportion. Thus, compounds that "modulate" a receptor affect the activity, either positively or negatively, of that receptor. The term may be used to refer to the activity of compounds of a receptor as, for example, an agonist, partial agonist or antagonist. The term also may be used to refer to the effect that a compound has on a physical and/or physiological condition of an individual. For example, certain compounds of the present invention may be used to modulate fertility in an individual. That is, certain compounds of this invention may be used to increase the fertility of an individual, while other compounds of this invention may be used to decrease the fertility of an individual.

A compound that binds to a receptor and mimics the effect of the native or endogenous ligand is referred to as an "agonist," while a compound that binds to a receptor and inhibits or has an effect that is opposite that of the native or endogenous ligand is called an "antagonist." "Partial agonists" give an effect of the same type as the native or endogenous ligand, but of a lower magnitude, while "partial antagonists" are incompletely inhibitory or opposite that of the native or endogenous ligand.

DETAILED DESCRIPTION OF THE INVENTION

Compounds of the present invention may be represented by the formulae:

(I)

wherein:

$R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;

$R^2$ and $R^3$ each independently is selected from the group of hydrogen, $C_1$–$C_6$ alkyl, and $C_1$–$C_6$ haloalkyl; or $R^2$ and $R^3$ taken together form a cycloalkyl ring of from three to twelve carbons;

$R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or $R^5$ and $R^7$ taken together form a bond; or $R^6$ and $R^7$ taken together are selected from the group of methylidene, mono-substituted methylidene, di-substituted methylidene and carbonyl;

$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;

$R^{13}$ is hydrogen; or $R^{13}$ and $R^{14}$ taken together form a bond;

$R^{14}$ through $R^{20}$ each independently is selected from the group of hydrogen, F, Cl, Br, $OR^{11}$, $C_1$–$C_4$ alkyl, $C_1$–$C_4$ haloalkyl, and $C_1$–$C_4$ heteroalkyl; or $R^{14}$ and $R^{15}$ taken together are selected from the group of methylidene, carbonyl and thiocarbonyl; or $R^{16}$ and $R^{17}$ taken together are selected from the group of methylidene, mono-substituted methylidene, di-substituted methylidene, ethylidene, carbonyl and thiocarbonyl; or $R^{14}$ and $R^{16}$ taken together form a bond or "—O—" bridge; or $R^{16}$ and $R^{18}$ taken together form a bond when n is 1; or $R^{16}$ and $R^{19}$ taken together form a bond when n is 0;

$R^{21}$ is hydrogen; or $R^{21}$ and $R^{20}$ taken together form a bond;

n is 0, 1, 2, or 3;

and pharmaceutically acceptable salts and prodrugs thereof.

Compounds of the invention include those represented by the formulae:

(II)

wherein:

$R^2$ and $R^3$ each independently is selected from the group of hydrogen, $C_1$–$C_4$ alkyl, and $C_1$–$C_4$ haloalkyl;

$R^6$ is selected from the group of hydrogen, F, Cl, Br, CN, $OR^{11}$, $C_1$–$C_4$ alkyl, and $C_1$–$C_4$ haloalkyl;

$R^8$ and $R^{10}$ each independently is selected from the group of hydrogen, F, Cl, Br, CN, $OR^{11}$, $NR^{11}R^{12}$, $SR^{11}$, $COR^{11}$, $C_1$–$C_4$ alkyl, $C_1$–$C_4$ heteroalkyl, $C_1$–$C_4$ haloalkyl, allyl, and $C_2$–$C_4$ alkenyl;

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;

$R^{14}$, $R^{15}$, $R^{18}$, $R^{22}$, $R^{23}$, $R^{24}$ each independently is selected from the group of hydrogen, F, Cl, $OR^{11}$, $C_1$–$C_4$ alkyl, $C_1$–$C_4$ haloalkyl, and $C_1$–$C_4$ heteroalkyl;

$R^{22}$, $R^{23}$, $R^{24}$ together consists of not more than 3 carbon atoms;

$R^{16}$ taken together with one of $R^{14}$, $R^{18}$, and $R^{22}$ form a bond or "—O—" bridge;

n is 0, 1, 2, or 3;

and pharmaceutically acceptable salts and prodrugs thereof.

In the following table, the inventors contemplate any combination of the following Markush groups and those described above for the various variables.

TABLE A

Table of Markush Groups by Variable

|   | Markush Group A | Markush Group B | Markush Group C | Markush Group D |
|---|---|---|---|---|
| $R^1$ | H, $C_1$–$C_4$ alkyl, $C_1$–C haloalkyl, $C_1$–$C_4$ heteroalkyl, $COR^{11}$, $CO_2R^{11}$, $SO_2R^{11}$ and $CONR^{11}R^{12}$ | H, $C_1$–$C_4$ alkyl, $COR^{11}$, $SO_2R^{11}$ and $CONR^{11}R^{12}$ | H and methyl | H |
| $R^2$ | H, $C_1$–$C_6$ alkyl and $C_1$–$C_6$ haloalkyl | $C_1$–$C_4$ alkyl and $C_1$–$C_4$ haloalkyl | H and methyl | H |
|   | $R^2$ and $R^3$ taken together form a $C_3$–$C_{12}$ cycloalkyl ring | $R^2$ and $R^3$ taken together form a $C_4$–$C_{10}$ cycloalkyl ring | $R^2$ and $R^3$ taken together form a $C_6$–$C_8$ cycloalkyl ring | $R^2$ and $R^3$ taken together form a $C_5$–$C_6$ cycloalkyl ring |
| $R^3$ | H, $C_1$–$C_6$ alkyl and $C_1$–$C_6$ haloalkyl | $C_1$–$C_4$ alkyl and $C_1$–$C_4$ haloalkyl | H and methyl | H |
| $R^4$ | H, F, Cl, Br, CN, $OR^{11}$, $C_1$–$C_4$ alkyl, $C_1$–$C_4$ haloalkyl and $C_1$–$C_4$ heteroalkyl | H, F, $OR^{11}$ and $C_1$–$C_4$ alkyl | H, F and methyl | H |
| $R^5$ | H, F, Cl, Br, CN, $OR^{11}$, $C_1$–$C_4$ alkyl, $C_1$–$C_4$ haloalkyl, and $C_1$–$C_4$ heteroalkyl | H, F and $C_1$–$C_4$ alkyl | H, F and methyl | H |
|   | $R^5$ and $R^7$ taken together form a bond |   |   |   |
| $R^6$ | H, F, Cl, Br, CN, $OR^{11}$, $C_1$–$C_4$ alkyl, $C_1$–$C_4$haloalkyl, and $C_1$–$C_4$ heteroalkyl | H, F, Cl, Br, CN, $OR^{11}$, $C_1$–$C_4$ alkyl, and $C_1$–$C_4$ haloalkyl | H and $C_1$–$C_4$ alkyl | methyl |
|   | $R^6$ and $R^7$ taken together form a methylidene, mono-substituted methylidene, di-substituted methylidene or carbonyl | $R^6$ and $R^7$ taken together form a methylidene or carbonyl |   | $R^6$ and $R^7$ taken together form a methylidene |
| $R^7$ | H, F, Cl, Br, CN, $OR^{11}$, $C_1$–$C_4$ alkyl, $C_1$–$C_4$ haloalkyl and $C_1$–$C_4$ heteroalkyl | H, F, $C_1$–$C_4$ alkyl and $C_1$–$C_4$ haloalkyl | H, F and methyl | H and F |
|   | $R^5$ and $R^7$ taken together form a bond |   |   |   |
|   | $R^6$ and $R^7$ taken together form a | $R^6$ and $R^7$ taken together form a | R and $R^7$ taken together form a | $R^6$ and $R^7$ taken together form a |

TABLE A-continued

Table of Markush Groups by Variable

| | Markush Group A | Markush Group B | Markush Group C | Markush Group D |
|---|---|---|---|---|
| | methylidene, mono-substituted methylidene, di-substituted methylidene or carbonyl | methylidene or carbonyl | carbonyl | methylidene |
| $R^8$ | H, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl | H, F, Cl, Br, $NO_2$, CN, $OR^{11}$, $SR^{11}$, $C_1$–$C_6$ alkyl, $C_1$–$C_6$ heteroalkyl, and $C_1$–$C_6$ haloalkyl | H, F, and $OR^{11}$ | H |
| $R^9$ | H, F, Cl, Br, I, $NO_2$, CN, $OR^{11}$, $NR^{11}R^{12}$, $SR^{11}$, $COR^{11}$, $CO_2R^{11}$, $CONR^HR^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl | H, F, Cl, Br, $NO_2$, CN, $OR^{11}$, $SR^{11}$, $C_1$–$C_6$ alkyl, $C_1$–$C_6$ heteroalkyl, and $C_1$–$C_6$ haloalkyl | H, F, and $OR^{11}$ | H |
| $R^{10}$ | H, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl | H, F, Cl, Br, $NO_2$, CN, $OR^{11}$, $SR^{11}$, $C_1$–$C_6$ alkyl, $C_1$–$C_6$ heteroalkyl and $C_1$–$C_6$ haloalkyl | H, F, and $OR^{11}$ | F |
| $R^{11}$ | H, $C_1$–$C_4$ alkyl, $C_1$–$C_4$ heteroalkyl and $C_1$–$C_4$ haloalkyl | H and $C_1$–$C_4$ alkyl | H and $C_1$–$C_2$ alkyl | H |
| $R^{12}$ | H, $C_1$–$C_4$ alkyl, $C_1$–$C_4$ heteroalkyl and $C_1$–$C_4$ haloalkyl | H and $C_1$–$C_4$ alkyl | H and $C_1$–$C_2$ alkyl | H |
| $R^{13}$ | H $R^{13}$ and $R^{14}$ taken together form a bond | | | |
| $R^{14}$ | H, F, Cl, Br, $OR^{11}$, $C_1$–$C_4$ alkyl, $C_1$–$C_4$ haloalkyl and $C_1$–$C_4$ heteroalkyl $R^{13}$ and $R^{14}$ taken together form a bond $R^{14}$ and $R^{15}$ taken together form a methylidene, carbonyl or | H, F, Cl, $C_1$–$C_4$ alkyl and $C_1$–$C_4$ haloalkyl $R^{14}$ and $R^{15}$ taken together form a methylidene or carbonyl | H, F, $C_1$–$C_2$ alkyl, and $C_1$–$C_2$ haloalkyl | H $R^{14}$ and $R^{15}$ taken together form a methylidene |

TABLE A-continued

Table of Markush Groups by Variable

| | Markush Group A | Markush Group B | Markush Group C | Markush Group D |
|---|---|---|---|---|
| | thiocarbonyl $R^{14}$ and $R^{16}$ taken together form a bond or "—O—" bridge | | $R^{14}$ and $R^{16}$ taken together form a "—O—" bridge | $R^{14}$ and $R^{16}$ taken together form a bond |
| $R^{15}$ | H, F, Cl, Br, $OR^{11}$, $C_1$–$C_4$ alkyl, $C_1$–$C_4$ haloalkyl and $C_1$–$C_4$ heteroalkyl | H, F, Cl, $C_1$–$C_4$ alkyl and $C_1$–$C_4$ haloalkyl | H and $C_1$–$C_4$ alkyl | H |
| | $R^{14}$ and $R^{15}$ taken together form a methylidene, carbonyl or thiocarbonyl | $R^{14}$ and $R^{15}$ taken together form a methylidene or carbonyl | | $R^{14}$ and $R^{15}$ taken together form a methylidene |
| $R^{16}$ | H, F, Cl, Br, $OR^{11}$, $C_1$–$C_4$ alkyl, $C_1$–$C_4$ haloalkyl and $C_1$–$C_4$ heteroalkyl | H, F, $OR^{11}$, $C_1$–$C_4$ alkyl, and $C_1$–$C_4$ haloalkyl | H, F, and $C_1$–$C_4$ alkyl | H |
| | $R^{14}$ and $R^{15}$ taken together form a bond or "—O—" bridge | | $R^{14}$ and $R^{16}$ taken together form a "—O—" bridge | $R^{14}$ and $R^{16}$ taken together form a bond |
| | $R^{16}$ and $R^{17}$ taken together form a methylidene, mono-substituted methylidene, di-substituted methylidene, ethylidene, carbonyl or thiocarbonyl | $R^{16}$ and $R^{17}$ taken together form a methylidene, mono-substituted methylidene, di-substituted methylidene, or ethylidene | $R^{16}$ and $R^{17}$ taken together form a methylidene or ethylidene | $R^{16}$ and $R^{17}$ taken together form a methylidene |
| | $R^{16}$ and $R^{18}$ taken together form a bond | | | |
| | $R^{16}$ and $R^{19}$ taken together form a bond | | | |
| $R^{17}$ | H, F, Cl, Br, $OR^{11}$, $C_1$–$C_4$ alkyl, $C_1$–$C_4$ haloalkyl and $C_1$–$C_4$ heteroalkyl | H, F, Cl, $C_1$–$C_4$ alkyl and $C_1$–$C_4$ haloalkyl | H and $C_1$–$C_2$ alkyl | methyl |
| | $R^{16}$ and $R^{17}$ taken together form a methylidene, mono-substituted methylidene, di-substituted methylidene, ethylidene, carbonyl or thiocarbonyl | $R^{16}$ and $R^{17}$ taken together form a methylidene, mono-substituted methylidene, di-substituted methylidene, or ethylidene | $R^{16}$ and $R^{17}$ taken together form a methylidene or ethylidene | $R^{16}$ and $R^{17}$ taken together form a methylidene |
| $R^{18}$ | H, F, Cl, Br, $OR^{11}$, $C_1$–$C_4$ alkyl, $C_1$–$C_4$ haloalkyl and $C_1$–$C_4$ heteroalkyl | H, F, Cl, $C_1$–$C_4$ alkyl and $C_1$–$C_4$ haloalkyl | H, F and $C_1$–$C_4$ alkyl | H |
| | $R^{16}$ and $R^{18}$ taken together form a bond | | | |
| $R^{19}$ | H, F, Cl, Br, $OR^{11}$, $C_1$–$C_4$ alkyl, $C_1$–$C_4$ haloalkyl and $C_1$–$C_4$ | H, F, Cl, $C_1$–$C_4$ alkyl and $C_1$–$C_4$ haloalkyl | H, F and $C_1$–$C_4$ alkyl | H |

TABLE A-continued

Table of Markush Groups by Variable

|  | Markush Group A | Markush Group B | Markush Group C | Markush Group D |
|---|---|---|---|---|
|  | heteroalkyl $R^{16}$ and $R^{19}$ taken together form a bond |  |  |  |
| $R^{20}$ | H, F, Cl, Br, $OR^{11}$, $C_1$–$C_4$ alkyl, $C_1$–$C_4$ haloalkyl and $C_1$–$C_4$ heteroalkyl $R^{21}$ and $R^{20}$ taken together form a bond | H, F, Cl, $C_1$–$C_4$ alkyl and $C_1$–$C_4$ haloalkyl | H, F and $C_1$–$C_2$ alkyl | H |
| $R^{21}$ | H $R^{21}$ and $R^{20}$ taken together form a bond |  |  |  |
| n |  | 0, 1, 2, or 3 | 0 or 1 |  | 1 |

In one aspect, the present invention provides a pharmaceutical composition comprising an effective amount of a progesterone receptor modulator compound according to any one of formulae I through II shown above wherein $R^1$ through $R^{24}$, and n all have the same definitions as given above.

In another aspect, the present invention comprises a method of modulating processes mediated by progesterone receptors comprising administering to a patient an effective amount of a compound according to any one of the formulae I through II shown above, wherein $R^1$ through $R^{24}$, and n all have the same definitions as those given above.

Any of the compounds of the present invention can be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those skilled in the art.

The PR agonist, partial agonist and antagonist compounds of the present invention may be particularly useful for female hormone replacement therapy and as modulators of fertility (e.g., as contraceptives, contragestational agents or abortifacients, in vitro fertilization, pregnancy maintenance), either alone or in conjunction with one or more estrogen receptor modulators. The PR modulator compounds of this invention may be also used in the treatment of dysfunctional uterine bleeding, dysmenorrhea, endometriosis, leiomyomas (uterine fibroids), hot flushes, mood disorders, and meningiomas. The PR modulator compounds of this invention also may be used in the treatment of various hormone-dependent cancers, including, without limitation, cancers of ovaries, breast, endometrium and prostate. The PR modulator compounds of this invention can also be used in treatment of female osteoporosis, either alone or in combination with one or more estrogen receptor modulators.

It will be understood by those skilled in the art that while the compounds of the present invention will typically be employed as a selective agonists, partial agonists or antagonists, that there may be instances where a compound with a mixed steroid receptor profile is preferred. For example, use of a PR agonist (i.e., progestin) in female contraception often leads to the undesired effects of increased water retention and acne flare ups. In this instance, a compound that is primarily a PR agonist, but also displays some AR and MR modulating activity, may prove useful. Specifically, the mixed MR effects would be useful to control water balance in the body, while the AR effects would help to control any acne flare ups that occur.

Furthermore, it will be understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative PR modulator compounds (i.e., agonists, partial agonists and antagonists) according to the present invention include:

(±)-(5l,1'l)-5-(3-methyl-2-cyclohexenyl)-9-fluoro-1,2-dihydro-2,2,4-trimethyl-5H-chromeno[3,4-f]quinoline (compound 24);

(±)-(5l,1'u)-5-(3-methyl-2-cyclohexenyl)-9-fluoro-1,2-dihydro-2,2,4-trimethyl-5H-chromeno[3,4-f]quinoline (compound 25);

(+)-(5l,1'l)-5-(3-methyl-2-cyclohexenyl)-9-fluoro-1,2-dihydro-2,2,4-trimethyl-5H-chromeno[3,4-f]quinoline (compound 27);

(−)-(5l,1'l)-5-(3-methyl-2-cyclohexenyl)-9-fluoro-1,2-dihydro-2,2,4-trimethyl-5H-chromeno[3,4-f]quinoline (compound 28);

(±)-(5l,1′l)-5-(3-methyl-2-cyclohexenyl)-9-hydroxy-1,2-dihydro-2,2,4-trimethyl-5H-chromeno[3,4-f]quinoline (compound 29);

(±)-(5l,1′u)-5-(3-methyl-2-cyclohexenyl)-9-hydroxy-1,2-dihydro-2,2,4-trimethyl-5H-chromeno[3,4-f]quinoline (compound 30);

(+)-(5l,1′l)-5-(3-methyl-2-cyclohexenyl)-9-hydroxy-1,2-dihydro-2,2,4-trimethyl-5H-chromeno[3,4-f]quinoline (compound 32);

(−)-(5l,1′l)-5-(3-methyl-2-cyclohexenyl)-9-hydroxy-1,2-dihydro-2,2,4-trimethyl-5H-chromeno[3,4-f]quinoline (compound 33);

(±)-(5l,1′l)-5-(3-methyl-2-cyclohexenyl)-7,9-difluoro-1,2-dihydro-2,2,4-trimethyl-5H-chromeno[3,4-f]quinoline (compound 34);

(±)-(5l,1′u)-5-(3-methyl-2-cyclohexenyl)-7,9-difluoro-1,2-dihydro-2,2,4-trimethyl-5H-chromeno[3,4-f]quinoline (compound 35);

(+)-(5l,1′l)-5-(3-methyl-2-cyclohexenyl)-7,9-difluoro-1,2-dihydro-2,2,4-trimethyl-5H-chromeno[3,4-f]quinoline (compound 37);

(−)-(5l,1′l)-5-(3-methyl-2-cyclohexenyl)-7,9-difluoro-1,2-dihydro-2,2,4-trimethyl-5H-chromeno[3,4-f]quinoline (compound 38);

(±)-(5l,1′l)-5-(3-methyl-2-cyclohexenyl)-9-methoxy-1,2-dihydro-2,2,4-trimethyl-5H-chromeno[3,4-f]quinoline (compound 39);

(±)-(5l,1′l)-5-(3-methyl-2-cyclohexenyl)-9-fluoro-1,2-dihydro-2,2-dimethyl-5H-chromeno[3,4-f]quinoline (compound 41);

(±)-(5l,1′u)-5-(3-methyl-2-cyclohexenyl)-9-fluoro-1,2-dihydro-2,2-dimethyl-5H-chromeno[3,4-f]quinoline (compound 42);

(±)-(5l,1′l)-5-(3-methyl-2-cyclopentenyl)-9-fluoro-1,2-dihydro-2,2,4-trimethyl-5H-chromeno[3,4-f]quinoline (compound 44);

(±)-(5l,1′u)-5-(3-methyl-2-cyclopentenyl)-9-fluoro-1,2-dihydro-2,2,4-trimethyl-5H-chromeno[3,4-f]quinoline (compound 45);

(±)-(5l,1′l)-5-(3,5,5-trimethyl-2-cyclohexenyl)-9-fluoro-1,2-dihydro-2,2,4-trimethyl-5H-chromeno[3,4-f]quinoline (compound 47);

(±)-(5l,1′u)-5-(3,5,5-trimethyl-2-cyclohexenyl)-9-fluoro-1,2-dihydro-2,2,4-trimethyl-5H-chromeno[3,4-f]quinoline (compound 48);

(±)-(5l,1′l)-5-(3-methyl-2-cyclopentenyl)-7,9-difluoro-1,2-dihydro-2,2,4-trimethyl-5H-chromeno[3,4-f]quinoline (compound 50);

(±)-(5l,1′u)-5-(3-methyl-2-cyclopentenyl)-7,9-difluoro-1,2-dihydro-2,2,4-trimethyl-5H-chromeno[3,4-f]quinoline (compound 51);

(±)-5-(3-methyl-3-cyclopentenyl)-7,9-difluoro-1,2-dihydro-2,2,4-trimethyl-5H-chromeno[3,4-f]quinoline (compound 52);

(±)-5-(2-cyclopenta-1,3-dienyl)-9-fluoro-1,2-dihydro-2,2,4-trimethyl-5H-chromeno[3,4-f]quinoline (compound 53);

(±)-(5l,1′l)-5-(3-ethyl-2-cyclohexenyl)-9-fluoro-1,2-dihydro-2,2,4-trimethyl-5H-chromeno[3,4-f]quinoline (compound 55);

(±)-(5l,1′u)-5-(3-ethyl-2-cyclohexenyl)-9-fluoro-1,2-dihydro-2,2,4-trimethyl-5H-chromeno[3,4-f]quinoline (compound 56);

(±)-(5l,1′l)-5-(3-methyl-2-cyclohexenyl)-7-fluoro-1,2-dihydro-2,2,4-trimethyl-5H-chromeno[3,4-f]quinoline (compound 58);

(±)-(5l,1′u)-5-(3-methyl-2-cyclohexenyl)-7-fluoro-1,2-dihydro-2,2,4-trimethyl-5H-chromeno[3,4-f]quinoline (compound 59);

(±)-(5l,1′)-5-(3-ethyl-2-cyclohexenyl)-7,9-difluoro-1,2-dihydro-2,2,4-trimethyl-5H-chromeno[3,4-f]quinoline (compound 61);

(±)-(5l,1′l)-5-(3-ethylidenecyclohexyl)-7,9-difluoro-1,2-dihydro-2,2,4-trimethyl-5H-chromeno[3,4-f]quinoline (compound 62);

(±)-(5l,1′l)-5-(3-methyl-3-cyclohexenyl)-7,9-difluoro-1,2-dihydro-2,2,4-trimethyl-5H-chromeno[3,4-f]quinoline (compound 63);

(±)-(5l,1′l)-5-(3-methyl-2-cyclohexenyl)-9-fluoro-1,2-dihydro-8-methoxy-2,2,4-trimethyl-5H-chromeno[3,4-f]quinoline (compound 64);

(±)-(5l,1′u)-5-(3-methyl-2-cyclohexenyl)-9-fluoro-1,2-dihydro-8-methoxy-2,2,4-trimethyl-5H-chromeno[3,4-f]quinoline (compound 65);

(±)-(5l,1′l)-5-(2-cyclopentenyl)-7,9-difluoro-1,2-dihydro-2,2,4-trimethyl-5H-chromeno[3,4-f]quinoline (compound 67);

(±)-(5l,1′u)-5-(2-cyclopentenyl)-7,9-difluoro-1,2-dihydro-2,2,4-trimethyl-5H-chromeno[3,4-f]quinoline (compound 68);

(±)-5-(1-cyclopentenyl)-7,9-difluoro-1,2-dihydro-2,2,4-trimethyl-5H-chromeno[3,4-f]quinoline (compound 69);

(±)-(5l,1′l)-5-(2,3-dimethyl-2-cyclopentenyl)-7,9-difluoro-1,2-dihydro-2,2,4-trimethyl-5H-chromeno[3,4-f]quinoline (compound 71);

(+)-(5l,1′l)-5-(2,3-dimethyl-2-cyclopentenyl)-7,9-difluoro-1,2-dihydro-2,2,4-trimethyl-5H-chromeno[3,4-f]quinoline (compound 73);

(−)-(5l,1′l)-5-(2,3-dimethyl-2-cyclopentenyl)-7,9-difluoro-1,2-dihydro-2,2,4-trimethyl-5H-chromeno[3,4-f]quinoline (compound 74);

(±)-(5l,1′l)-5-(2-cyclohexenyl)-7,9-difluoro-1,2-dihydro-2,2,4-trimethyl-5H-chromeno[3,4-f]quinoline (compound 75);

(±)-(5l,1′u)-5-(2-cyclohexenyl)-7,9-difluoro-1,2-dihydro-2,2,4-trimethyl-5H-chromeno[3,4-f]quinoline (compound 76);

(±)-(5l,1′l)-5-(2-cyclohexenyl)-7,9-difluoro-1,2,3,4-tetrahydro-2,2-dimethyl-4-methylidene-5H-chromeno[3,4-f]quinoline (compound 77);

(±)-(5l,1′l)-5-(2-methylidenecyclohexyl)-9-fluoro-1,2-dihydro-2,2,4-trimethyl-5H-chromeno[3,4-f]quinoline (compound 79);

(±)-(5l,1′u)-5-(2-methylidenecyclohexyl)-9-fluoro-1,2-dihydro-2,2,4-trimethyl-5H-chromeno[3,4-f]quinoline (compound 80);

(±)-(5l,1′)-5-(2-oxocyclohexyl)-9-fluoro-1,2-dihydro-2,2,4-trimethyl-5H-chromeno[3,4-f]quinoline (compound 81);

(±)-(5l,1′u)-5-(2-oxocyclohexyl)-9-fluoro-1,2-dihydro-2,2,4-trimethyl-5H-chromeno[3,4-f]quinoline (compound 82);

(±)-(5l,1′l)-5-(3-methyl-2-cyclohexenyl)-9-methoxy-1,2-dihydro-1,2,2,4-tetramethyl-5H-chromeno[3,4-f]quinoline (compound 83);

(±)-5-(2-cyclohexenyl)-9-fluoro-1,2-dihydro-2,2,4-trimethyl-5H-chromeno[3,4-f]quinoline (compound 84);

(±)-(5l,1′l)-5-(2,3-dimethyl-2-cyclohexenyl)-7,9-difluoro-1,2-dihydro-2,2,4-trimethyl-5H-chromeno[3,4-f]quinoline (compound 85);

(±)-5-(3-methylidene-cyclohexyl)-7,9-difluoro-1,2-dihydro-2,2,4-trimethyl-5H-chromeno[3,4-f]quinoline (compound 87);

(±)-(5l,1'u)-5-(3-ethylidenecyclohexyl)-7,9-difluoro-1,2-dihydro-2,2,4-trimethyl-5H-chromeno[3,4-f]quinoline (compound 88);

(±)-(5l,1'l)-5-(2-cycloheptenyl)-7,9-difluoro-1,2-dihydro-2,2,4-trimethyl-5H-chromeno[3,4-f]quinoline (Compound 89);

(±)-(5l,1'l)-5-(2-cyclooctenyl)-7,9-difluoro-1,2-dihydro-2,2,4-trimethyl-5H-chromeno[3,4-f]quinoline (Compound 91);

(±)-(5l,1'u)-5-(2-cyclooctenyl)-7,9-difluoro-1,2-dihydro-2,2,4-trimethyl-5H-chromeno[3,4-f]quinoline (Compound 92);

(±)-(5l,1'l)-5-(2,3-epoxy-3-methylcyclohexyl)-7,9-difluoro-1,2-dihydro-2,2,4-trimethyl-5H-chromeno[3,4-f]quinoline (Compound 94);

(±)-(5l,1'l)-5-(3-methyl-2-cyclohexenyl)-7,9-difluoro-1,2,3,4-tetrahydro-2,2-dimethyl-4-methylene-5H-chromeno[3,4-f]quinolin-3-ol (Compound 95);

(±)-(5l,1'l)-5-(2,3-epoxy-2,3-dimethylcyclopentyl)-7,9-difluoro-1,2-dihydro-2,2,4-trimethyl-5H-chromeno[3,4-f]quinoline (Compound 96);

(±)-(5l,1'u)-5-(2,3-epoxy-3-methylcyclohexyl)-7,9-difluoro-1,2-dihydro-2,2,4-trimethyl-5H-chromeno[3,4-f]quinoline (Compound 97); and (±)-(5l,1'l)-5-(3-methyl-2-cyclohexenyl)-7,9-difluoro-1,2,3,4-tetrahydro-2,2-dimethyl-5H-chromeno[3,4-f]quinolin-4-one (Compound 98).

The sequence of steps for the general schemes to synthesize the compounds of the present invention is shown below. In each of the Schemes the R groups (e.g., $R^1$, $R^2$, etc.) correspond to the specific substitution patterns noted in the Examples. However, it will be understood by those skilled in the art that other functionalities disclosed herein at the indicated positions of compounds of formulae I and II also comprise potential substituents for the analogous positions on the structures within the Schemes. In a further aspect, the present invention contains a novel process for the preparation of the compounds of the present invention.

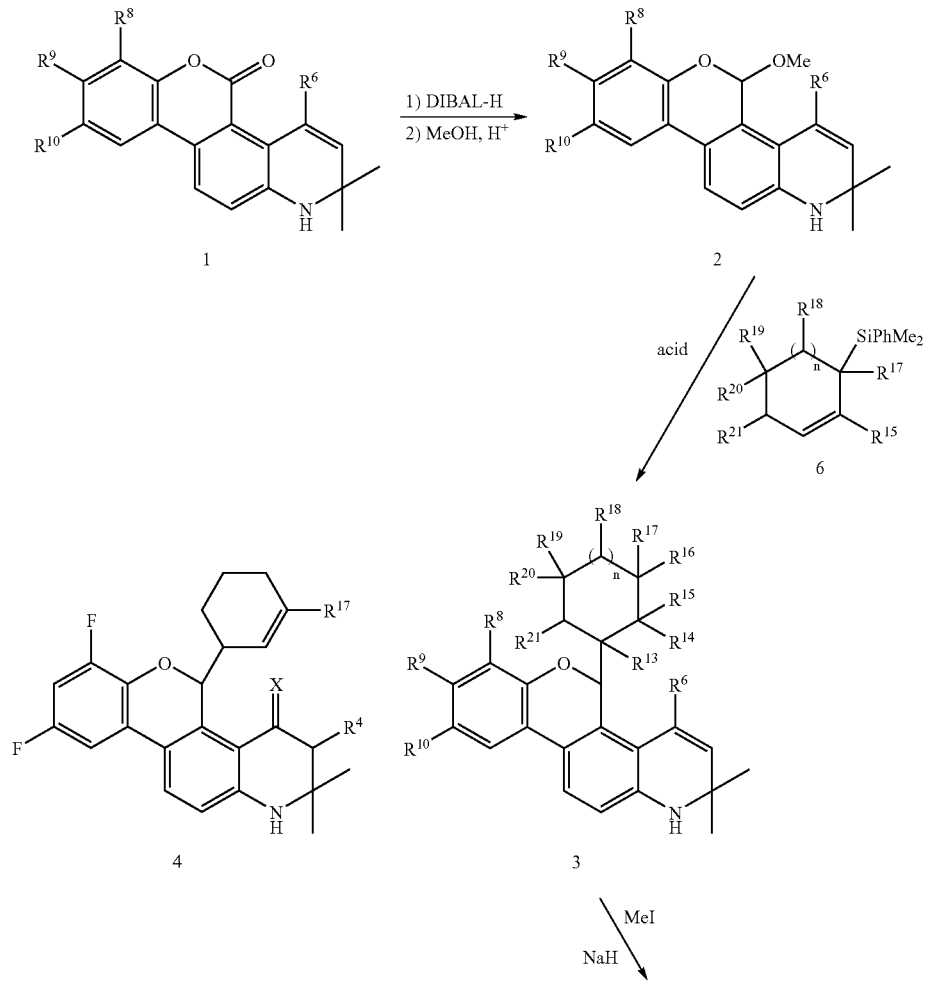

Scheme I

-continued

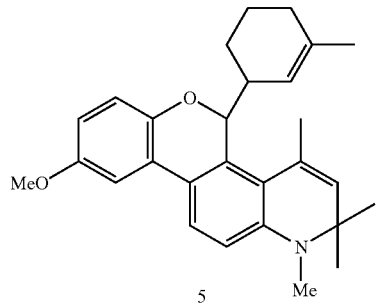

Scheme I describes the synthesis of the 5-cycloalkenyl analogues 3, 4 and 5. Reduction of lactones 1, which were prepared by the previously disclosed methods (U.S. Pat. Nos. 5,693,646; 5,693,647 and 5,696,127), with DIBAL-H followed by acid catalyzed methylation provides lactal intermediates 2. Treatment of the lactal 2 with a nucleophile, such as a cyclic allylsilane 6, in the presence of a Lewis acid, such as $BF_3$-$OEt_2$, affords the final product 3. Compound of structure 4 may also isolated as a minor product. Methylation of compound 3 with iodomethane in the presence of a base, such as sodium hydride, provides N-methylated product of structure 5.

The compounds of the present invention also include racemates, stereoisomers and mixtures of said compounds, including isotopically-labeled and radio-labeled compounds. Such isomers can be isolated by standard resolution techniques, including fractional crystallization and chiral column chromatography.

As noted above, any of the PR modulator compounds of the present invention can be combined in a mixture with a pharmaceutically acceptable carrier to provide pharmaceutical compositions useful for treating the biological conditions or disorders noted herein in mammalian, and particularly in human patients. The particular carrier employed in these pharmaceutical compositions may take a wide variety of forms depending upon the type of administration desired. Suitable administration routes include enteral (e.g., oral), topical, suppository, inhalable and parenteral (e.g., intravenous, intramuscular and subcutaneous).

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent a desirable oral dosage form for the pharmaceutical compositions of the present invention.

For parenteral administration, the carrier will typically comprise sterile water, although other ingredients that aid in solubility or serve as preservatives may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin and water in oil emulsions such as Eucerin™, available from Beiersdorf (Cincinnati, Ohio). Examples of suitable cream bases are Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Warner-Lambert (Morris Plains, N.J.).

The pharmaceutical compositions and compounds of the present invention will generally be administered in the form of a dosage unit (e.g., tablet, capsule, etc.). The compounds of the present invention generally are administered in a daily dosage of from about 1 µg/kg of body weight to about 50 mg/kg of body weight. Typically, the compounds of the present invention are administered in a daily dosage of from about 2 µg/kg to about 25 mg/kg of body weight. Most often, the compounds of the present invention are administered in a daily dosage of from about 10 µg/kg to about 5 mg/kg body weight. As recognized by those skilled in the art, the particular quantity of pharmaceutical composition according to the present invention administered to a patient will depend upon a number of factors, including, without limitation, the biological activity desired, the condition of the patient, and tolerance for the drug.

The compounds of this invention also have utility when radio- or isotopically-labeled as ligands for use in assays to determine the presence of PR in a cell background or extract. They are particularly useful due to their ability to selectively activate progesterone receptors, and can therefore be used to determine the presence of such receptors in the presence of other steroid receptors or related intracellular receptors.

The compounds and pharmaceutical compositions of the present invention may be extremely potent activators of PR. For example, the compounds and compositions of the present invention may display 50% maximal activation of PR at a concentration of less than 50 nM. Some compounds and compositions of the present invention may display 50% maximal activation of PR at a concentration of less than 20 nM, and some may display such activity at a concentration of less than 10 nM.

The invention will be further illustrated by reference to the following non-limiting Examples.

EXAMPLE 1

Preparation of (±)-(5l,1'l)-5-(3-methyl-2-cyclohexenyl)-9-fluoro-1,2-dihydro-2,2,4-trimethyl-5H-chromeno[3,4-f]quinoline and (±)-(5l,1'u)-5-(3-methyl-2-cyclohexenyl)-9-fluoro-1,2-dihydro-2,2,4-trimethyl-5H-chromeno[3,4-f]quinoline (Compounds 24 and 25, Structure 3 of Scheme I, where $R^8=R^9=R^{13}=R^{15}=R^{18}=R^{19}=R^{20}=R^{21}=H$, $R^{10}=F$, $R^6=R^{17}=$methyl, $R^{14}/R^{16}=$a bond, n=1)

These compounds were prepared according the following general procedure:

A mixture of a 5-methoxy-5H-chromeno[3,4-f]quinoline, such as 9-fluoro-2,2,4-trimethyl-5-methoxy-1,2-dihydro-5H-chromeno[3,4-f]quinoline (compound 26, Structure 2 of Scheme I, where $R^8=R^9=H$, $R^{10}=F$, $R^6=$methyl), and a cyclic allylsilane derivative, such as 3-(dimethylphenylsilyl)-3-methyl-1-cyclohexene (Structure 6 of Scheme I, where $R^{17}=$methyl, $R^{15}=R^{18}=R^{19}=R^{20}=R^{21}=H$, n=1) (1.0–1.5 equiv.), in dry $CH_2Cl_2$ was cooled to −25° C., after which a Lewis acid such as $BF_3Et_2O$ (excess) was added dropwise. The resulting mixture was stirred at −25° C. for half an hour, then warmed up gradually to 0° C. and quenched with slow addition of aqueous $NaHCO_3$ (concentrated). The reaction mixture was extracted with $CH_2Cl_2$ (3×). The extracts were washed with brine, combined, dried over anhydrous $Na_2SO_4$, filtered, and concentrated. Purification by flash chromatography (hexane:EtOAc, 9:1) afforded 40–90% of a diastereomeric mixture of the 5-alkenyl products, which then were separated by prep TLC or HPLC.

Compound 24 was isolated as the major isomer: $^1$H-NMR (500 MHz, $CDCl_3$) 7.38 (d, J=8.2, 1H), 7.29 (dt, J=9.4, 3.1, 1H), 6.91 (dd, J=8.6, 4.9, 1H), 6.82 (dt, J=8.6, 3.1, 1H), 6.61 (d, J=8.2, 1H), 5.64 (s, 1H), 5.52 (d, J=14.0, 1H), 5.51 (s, 1H), 4.00 (s, 1H), 2.40 (m, 1H), 2.24 (s, 3H), 1.87 (m, 1H), 1.80 (m, 1H), 1.64 (m, 1H), 1.56 (s, 3H), 1.38 (s, 3H), 1.28 (m, 1H), 1.22 (m, 1H), 1.14 (s, 3H), 1.06 (m, 1H).

Compound 25 was isolated as a minor isomer: $^1$H NMR (500 MHz, $CDCl_3$) 7.38 (d, J=8.2, 1H), 7.29 (dt, J=9.4, 3.1, 1H), 6.86 (m, 1H), 6.82 (m, 1H), 6.61 (dd, J=8.2, 1.8, 1H), 5.63 (d, J=10.1, 1H), 5.47 (s, 1H), 4.89 (s, 1H), 3.99 (s, 1H), 2.38 (m, 1H), 2.17 (s, 3H), 1.88 (m, 2H), 1.77 (m, 1H), 1.69 (m, 2H), 1.54 (s, 3H), 1.48 (m, 1H), 1.38 (d, J=1.8, 3H), 1.20 (d, J=1.2, 3H).

EXAMPLE 2

Preparation of (+)-(5l,1'l)-5-(3-methyl-2-cyclohexenyl)-9-fluoro-1,2-dihydro-2,2,4-trimethyl-5H-chromeno[3,4-f]quinoline and (−)-(5l,1'l)-5-(3-methyl-2-cyclohexenyl)-9-fluoro-1,2-dihydro-2,2,4-trimethyl-5H-chromeno[3,4-f]quinoline (Compounds 27 and 28, Structure 3 of Scheme I, where $R^8=R^9=R^{13}=R^{15}=R^{18}=R^{19}=R^{20}=R^{21}=H$, $R^{10}=F$, $R^6=R^{17}=$methyl, $R^{14}/R^{16}=$a bond, n=1)

These compounds were obtained through chiral HPLC separation of compound 24 using a Chiral AD Semiprep Column, 250×20 mm ID, 90% Hexanes/EtOH. Data for compound 27, $[\alpha]^{22}_D=+332.3$ and compound 28, $[\alpha]^{22}_D=-317.1$ (EtOH).

EXAMPLE 3

Preparation of (±)-(5l,1'l)-5-(3-methyl-2-cyclohexenyl)-9-hydroxy-1,2-dihydro-2,2,4-trimethyl-5H-chromeno[3,4-f]quinoline and (±)-(5l,1'u)-5-(3-methyl-2-cyclohexenyl)-9-hydroxy-1,2-dihydro-2,2,4-trimethyl-5H-chromeno[3,4-f]quinoline (Compounds 29 and 30, Structure 3 of Scheme I, where $R^8=R^9=R^{13}=R^{15}=R^{18}=R^{19}=R^{20}=R^{21}=H$, $R^{10}=$hydroxy, $R^6=R^{17}=$methyl, $R^{14}/R^{16}=$a bond, n=1)

These compounds were prepared in a similar fashion as that described in Example 1 general procedure from 3-(dimethylphenylsilyl)-3-methyl-1-cyclohexene (Structure 6 of Scheme I, where $R^{17}=$methyl, $R^{15}=R^{18}=R^{19}=R^{20}=R^{21}=H$, n=1) and 9-hydroxy-2,2,4-trimethyl-5-methoxy-1,2-dihydro-5H-chromeno[3,4-f]quinoline (Compound 31, Structure 2 of Scheme I, where $R^8=R^9=H$, $R^{10}=$hydroxy, $R^6=$methyl).

Compound 29 was isolated as the major isomer: $^1$H NMR (500 MHz, $CDCl_3$) 7.38 (d, J=8.2, 1H), 7.10 (d, J=2.4, 1H), 6.86 (d, J=8.5, 1H), 6.82 (dt, J=8.6, 3.1, 1H), 6.62 (dd, J=8.5, 2.7, 1H), 6.60 (d, J=8.2, 1H), 5.67 (s, 1H), 5.50 (s, 1H), 5.48 (d, J=12.2, 1H), 3.96 (s, 1H), 2.42 (m, 1H), 2.24 (s, 3H), 1.87 (m, 1H), 1.77 (m, 1H), 1.66 (s, 3H), 1.64 (m, 1H), 1.38 (s, 3H), 1.28 (m, 1H), 1.20 (m, 1H), 1.13 (s, 3H), 1.02 (m, 1H).

Compound 30 was isolated as a minor isomer: $^1$H NMR (500 MHz, $CDCl_3$) 7.38 (d, J=8.8, 1H), 7.18 (d, J=3.7, 1H), 7.10 (d, J=3.7, 1H), 6.81 (d, J=7.9, 1H), 6.62 (m, 1H), 5.59 (d, J=10.2, 1H), 5.47 (s, 1H), 4.90 (s, 1H), 4.45 (s, 1H), 3.96 (s, 1H), 2.40 (m, 1H), 2.17 (s, 3H), 1.88 (m, 1H), 1.78 (m, 1H), 1.68 (m, 1H), 1.60 (s, 3H), 1.38 (s, 3H), 1.30 (m, 2H), 1.20 (s, 3H), 0.90 (m, 1H).

EXAMPLE 4

Preparation of (+)-(5l,1'l)-5-(3-methyl-2-cyclohexenyl)-9-hydroxy-1,2-dihydro-2,2,4-trimethyl-5H-chromeno[3,4-f]quinoline and (−)-(5l,1'l)-5-(3-methyl-2-cyclohexenyl)-9-hydroxy-1,2-dihydro-2,2,4-trimethyl-5H-chromeno[3,4-f]quinoline (Compounds 32 and 33, Structure 3 of Scheme I, where $R^8=R^9=R^{13}=R^{15}=R^{18}=R^{19}=R^{20}=R^{21}=H$, $R^{10}=$hydroxy, $R^6=R^{17}=$methyl, $R^{14}/R^{16}=$a bond, n=1)

These compounds were obtained through chiral HPLC separation of compound 29 using a Chiral AD Semiprep Column, 250×20 mm ID, 90% Hexanes/EtOH. Data for compound 32, $[\alpha]^{22}_D=+201.6$ and compound 33, $[\alpha]^{22}_D=-207.7$ (EtOH).

EXAMPLE 5

Preparation of (±)-(5l,1'l)-5-(3-methyl-2-cyclohexenyl)-7,9-difluoro-1,2-dihydro-2,2,4-trimethyl-5H-chromeno[3,4-f]quinoline, (+)-(5l,1'u)-5-(3-methyl-2-cyclohexenyl)-7,9-difluoro-1,2-dihydro-2,2,4-trimethyl-5H-chromeno[3,4-f]quinoline (Compounds 34 and 35, Structure 3 of Scheme I, where $R^9=R^{13}=R^{15}=R^{18}=R^{19}=R^{20}=R^{21}=H$, $R^8=R^{10}=$fluorine, $R^6=R^{17}=$methyl, $R^{14}/R^{16}=$a bond, n=1) and (±)-5-(3-methylidene-cyclohexyl)-7,9-difluoro-1,2-dihydro-2,2,4-trimethyl-5H-chromeno[3,4-f]quinoline (Compounds 87, Structure 3 of Scheme I, where $R^9=R^{13}=R^{14}=R^{15}=R^{18}=R^{19}=R^{20}=R^{21}=H$, $R^8=R^{10}=$fluorine, $R^6=$methyl, $R^{16}/R^{17}=$methylidene, n=1)

These compounds were prepared in a similar fashion as that described in Example 1 general procedure from 3-dimethylphenylsilyl-3-methyl-1-cyclohexene (Structure 6 of Scheme I, where $R^{17}=$methyl, $R^{15}=R^{18}=R^{19}=R^{20}=R^{21}=H$, n=1) and 7,9-difluoro-1,2-dihydro-2,2,4-trimethyl-5-methoxy-5H-chromeno[3,4-f]quinoline (Compound 36, Structure 5 of Scheme I, where $R^8=R^{10}=$fluorine, $R^9=H$, $R^6=$methyl).

Compound 34 was isolated as a major product: $^1$H NMR (500 MHz, $CDCl_3$) 7.36 (d, J=8.2, 1H), 7.29 (dt, J=9.4, 1.8, 1H), 6.70 (td, J=9.5, 3.0, 1H), 6.61 (d, J=8.2, 1H), 5.64 (d, J=9.5, 1H), 5.63 (s, 1H), 5.51 (s, 1H), 4.04 (s, 1H), 2.38 (m, 1H), 2.24 (s, 3H), 1.88 (m, 1H), 1.77 (m, 1H), 1.69 (m, 1H), 1.65 (s, 3H), 1.39 (s, 3H), 1.30 (m, 1H), 1.25 (m, 1H), 1.14 (s, 3H), 1.10 (m, 1H).

Compound 35 was isolated as a miner product: 1H NMR (500 MHz, $CDCl_3$) 7.35 (d, J=8.2, 1H), 7.10 (dt, J=9.8, 2.4, 1H), 6.70 (td, J=10.8, 3.0, 1H), 6.61 (d, J=8.2, 1H), 5.74 (d, J=10.4, 1H), 5.48 (s, 1H), 4.87 (s, 1H), 4.03 (s, 1H), 2.37 (m, 1H), 2.17 (s, 3H), 1.90 (m, 1H), 1.78 (m, 1H), 1.72 (m, 2H), 1.54 (s, 3H), 1.52 (m, 1H), 1.38 (s, 3H), 1.20 (d, J=1.21, 3H).

Compound 87 was isolated as a 1.6:1 mixture of two diastereomers: $^1$H NMR (500 MHz, $CDCl_3$) 7.36 (d, J=8.2, 1H), 7.34 (d, J=8.2, 1H), 7.14–7.08 (m, 2H), 6.73–6.67 (m, 2H), 6.60 (d, J=11.3, 1H), 6.58 (d, J=8.2, 1H), 6.10 (d, J=10.1, 1H), 5.72 (d, J=10.1, 1H), 5.64 (d, J=9.2, 1H), 5.62 (s, 1H), 5.51 (s, 1H), 5.42 (s, 1H), 5.39–5.37 (m, 1H), 5.31–5.29 (m, 1H), 4.08–4.02 (m, 1H), 4.01–3.99 (m, 1H), 2.33–2.30 (m, 2H), 2.24 (s, 3H), 2.23 (s, 3H), 2.20–2.00 (m, 4H), 1.99–1.86 (m, 2H), 1.84–1.78 (m, 2H), 1.39 (s, 3H), 1.36 (s, 3H), 1.32–1.22 (m, 4H), 1.14 (s, 3H), 1.13 (s, 3H), 0.98–0.92 (m, 2H).

EXAMPLE 6

Preparation of (+)-(5l,1'l)-5-(3-methyl-2-cyclohexenyl)-7,9-difluoro-1,2-dihydro-2,2,4-trimethyl-5H-chromeno[3,4-f]quinoline and (−)-(5l,1'l)-5-(3-methyl-2-cyclohexenyl)-7,9-difluoro-1,2-dihydro-2,2,4-trimethyl-5H-chromeno[3,4-f]quinoline (Compounds 37 and 38, Structure 3 of Scheme I, where $R^9=R^{13}=R^{15}=R^{18}=R^{19}=R^{20}=R^{21}=H$, $R^8=R^{10}=$fluorine, $R^6=R^{17}=$methyl, $R^{14}/R^{16}=$a bond, n=1)

These compounds were obtained through chiral HPLC separation of compound 34 using a Chiral AD Semiprep Column, 250×20 mm ID, 90% Hexanes/EtOH. Data for compound 37, $[\alpha]^{22}_D=+342.4$ and compound 38, $[\alpha]^{22}_D=-340.0$ (EtOH).

EXAMPLE 7

Preparation of (±)-(5l,1'l)-5-(3-methyl-2-cyclohexenyl)-9-methoxy-1,2-dihydro-2,2,4-trimethyl-5H-chromeno[3,4-f]quinoline (Compound 39. Structure 3 of Scheme I, where $R^8=R^9=R^{13}=R^{15}=R^{18}=R^{19}=R^{20}=R^{21}=H$, $R^{10}=$methoxy, $R^6=R^{17}=$methyl, $R^{14}/R^{16}=$a bond, n=1)

This compound was prepared in a similar fashion as that described in Example 1 general procedure from 3-(dimethylphenylsilyl)-3-methyl-1-cyclohexene (Structure 6 of Scheme I, where $R^{17}=$methyl, $R^{15}=R^{18}=R^{19}=R^{20}=R^{21}=H$, n=1) and 5,9-dimethoxy-1,2-dihydro-2,2,4-trimethyl-5H-chromeno[3,4-f]quinoline (Compound 40, Structure 2 of Scheme I, where $R^5=R^9=H$, $R^{10}=$methoxy, $R^6=$methyl) as a yellow solid: $^1$H NMR (500 MHz, CDCl$_3$) 7.43 (d, J=7.9, 1H), 7.16 (s, 1H), 6.92 (d, J=8.9, 1H), 6.72 (m, 1H), 6.62 (m, 1H), 5.59 (s, 1H), 5.49 (s, 1H), 5.48 (d, J=9.8, 1H), 3.96 (s, 1H), 3.82 (s, 3H), 2.41 (m, 1H), 2.24 (s, 3H), 1.87 (m, 1H), 1.78 (m, 1H), 1.62 (m, 1H), 1.57 (s, 3H), 1.38 (s, 3H), 1.26 (m, 1H), 1.20 (m, 1H), 1.13 (s, 3H), 1.04 (m, 1H).

EXAMPLE 8

Preparation of (±)-(5l,1'l)-5-(3-methyl-2-cyclohexenyl)-9-fluoro-1,2-dihydro-2,2-dimethyl-5H-chromeno[3,4-f]quinoline and (±)-(5l,1'u)-5-(3-methyl-2-cyclohexenyl)-9-fluoro-1,2-dihydro-2,2-dimethyl-5H-chromeno[3,4-f]quinoline (Compounds 41 and 42, Structure 3 of Scheme I, where $R^6=R^8=R^9=R^{13}=R^{15}=R^{18}=R^{19}=R^{20}=R^{21}=H$, $R^{10}=$fluorine, $R^{17}=$methyl, $R^{14}/R^{16}=$a bond, n=1)

These compounds were prepared in a similar fashion as that described in Example 1 general procedure from 3-(dimethylphenylsilyl)-3-methyl-1-cyclohexene (Structure 6 of Scheme I, where $R^{17}=$methyl, $R^{15}=R^{18}=R^{19}=R^{20}=R^{21}=H$, n=1) and 9-fluoro-1,2-dihydro-2,2-dimethyl-5-methoxy-5H-chromeno[3,4-f]quinoline (Compound 43, Structure 5 of Scheme I, where $R^{10}=$fluorine, $R^6=R^8=R^9=H$).

Compound 41 was isolated as a major product: $^1$H NMR (500 MHz, CDCl$_3$) 7.38 (d, J=8.5, 1H), 7.28 (dd, J=9.8, 3.1, 1H), 6.89 (dd, J=8.5, 4.9, 1H), 6.79 (dt, J=8.6, 2.8, 1H), 6.48 (d, J=8.5, 1H), 6.43 (d, J=10.1, 1H), 5.62 (s, 1H), 5.58 (d, J=10.1, 1H), 5.10 (d, J=9.2, 1H), 3.86 (s, 1H), 2.44 (m, 1H), 1.89 (m, 1H), 1.80 (m, 1H), 1.74 (m, 1H), 1.56 (s, 3H), 1.35 (s, 3H), 1.34 (m, 2H), 1.31 (s, 3H), 1.27 (m, 1H).

Compound 42 was isolated as a minor product: $^1$H NMR (500 MHz, CDCl$_3$) 7.31 (d, J=8.5, 1H), 7.28 (dd, J=8.9, 2.1, 1H), 6.87 (dd, J=9.2, 5.2, 1H), 6.80 (dt, J=8.2, 3.1, 1H), 6.49 (d, J=8.2, 1H), 6.36 (d, J=10.1, 1H), 5.55 (d, J=10.4, 1H), 5.10 (d, J=10.1, 1H), 4.88 (s, 1H), 3.88 (s, 1H), 2.44 (m, 1H), 1.90 (m, 1H), 1.72 (m, 1H), 1.60 (m, 2H), 1.56 (s, 3H), 1.52 (m, 2H), 1.35 (s, 3H), 1.32 (s, 3H).

EXAMPLE 9

Preparation of (±)-(5l,1'l)-5-(3-methyl-2-cyclopentenyl)-9-fluoro-1,2-dihydro-2,2,4-trimethyl-5H-chromeno[3,4-f]quinoline and (±)-(5l,1'u)-5-(3-methyl-2-cyclopentenyl)-9-fluoro-1,2-dihydro-2,2,4-trimethyl-5H-chromeno[3,4-f]quinoline (Compounds 44 and 45, Structure 3 of Scheme I, where $R^8=R^9=R^{13}=R^{15}=R^{19}=R^{20}=R^{21}=H$, $R^{10}=F$, $R^6=R^{17}=$methyl $R^{14}/R^{16}=$a bond, n=0)

These compounds were prepared in a similar fashion as that described in Example 1 general procedure from 3-(dimethylphenylsilyl)-3-methylcyclopentene (Compound 46, Structure 6 of Scheme I, where $R^{17}=$methyl, $R^{15}=R^{19}=R^{20}=R^{21}=H$, n=0) and compound 26 (Structure 2 of Scheme I, where $R^8=R^9=H$, $R^{10}=$fluorine, $R^6=$methyl).

Compound 44 was isolated as a major product: $^1$H NMR (500 MHz, CDCl$_3$) 7.38 (d, J=8.5, 1H), 7.29 (dd, J=10.4, 2.8, 1H), 6.86 (dd, J=8.9, 5.2, 1H), 6.79 (dt, J=8.2, 3.1, 1H), 6.60 (d, J=8.2, 1H), 5.61 (d, J=8.8, 1H), 5.52 (s, 1H), 5.34 (s, 1H), 3.99 (s, 1H), 3.00 (m, 1H), 2.24 (s, 3H), 2.29 (m, 1H), 1.63 (m, 2H), 1.55 (s, 3H), 1.38 (s, 3H), 1.14 (s, 3H), 1.06 (m, 1H).

Compound 45 was isolated as a minor product: $^1$H NMR (500 MHz, CDCl$_3$) 7.38 (d, J=8.2, 1H), 7.29 (dd, J=8.8, 1.8, 1H), 6.85 (dd, J=8.6, 5.2, 1H), 6.81 (dt, J=8.2, 3.1, 1H), 6.60 (d, J=8.2, 1H), 5.55 (d, J=10.4, 1H), 5.47 (s, 1H), 4.81 (s, 1H), 3.99 (s, 1H), 2.96 (m, 1H), 2.34 (m, 1H), 2.18 (m, 1H), 2.14 (s, 3H), 2.09 (m, 1H), 1.91 (m, 1H), 1.55 (s, 3H), 1.38 (s, 3H), 1.20 (s, 3H).

EXAMPLE 10

Preparation of (±)-(5l,1'l)-5-(3,5,5-trimethyl-2-cyclohexenyl)-9-fluoro-1,2-dihydro-2,2,4-trimethyl-5H-chromeno[3,4-f]quinoline and (±)-(5l,1'u)-5-(3,5,5-trimethyl-2-cyclohexenyl)-9-fluoro-1,2-dihydro-2,2,4-trimethyl-5H-chromeno[3,4-f]quinoline (Compounds 47 and 48, Structure 3 of Scheme I, where $R^8=R^9=R^{13}=R^{15}=R^{18}=R^{21}=H$, $R^{10}=$fluorine, $R^6=R^{17}=R^{19}=R^{20}=$methyl, $R^{14}/R^{16}=$a bond, n=1)

These compounds were prepared in a similar fashion as that described in Example 1 general procedure from 3-(dimethylphenylsilyl)-3,5,5-trimethylcyclohexene (Compound 49, Structure 6 of Scheme I, where $R^{17}=R^{19}=R^{20}=$methyl, $R^{15}=R^{18}=R^{21}=H$, n=1) and compound 26 (Structure 2 of Scheme I, where $R^{10}=$fluorine, $R^6=$methyl, $R^8=R^9=H$).

Compound 47 was isolated as a major product: $^1$H NMR (500 MHz, CDCl$_3$) 7.39 (d, J=8.2, 1H), 7.30 (dd, J=9.8, 3.1, 1H), 6.91 (dd, J=8.9, 4.9, 1H), 6.82 (dt, J=8.6, 3.1, 1H), 6.62 (d, J=8.2, 1H), 5.64 (s, 1H), 5.52 (d, J=9.5, 1H), 5.51 (d, J=1.2, 1H), 4.01 (s, 1H), 2.43 (m, 1H), 2.22 (d, J=1.2, 3H), 1.77 (d, J=17.1, 1H), 1.65 (s, 3H), 1.48 (d, J=17.4, 1H), 1.38 (s, 3H), 1.12 (s, 3H), 0.88 (t, J=12.2, 1H), 0.81 (s, 3H), 0.77 (m, 1H), 0.58 (s, 3H).

Compound 48 was isolated as a minor isomer: $^1$H NMR (500 MHz, CDCl$_3$) 7.38 (d, J=8.2, 1H), 7.28 (dd, J=10.1, 2.7, 1H), 6.87 (dd, J=8.9, 5.2, 1H), 6.82 (dt, J=7.9, 2.8, 1H), 6.62 (d, J=8.2, 1H), 5.56 (d, J=10.1, 1H), 5.50 (s, 1H), 4.94 (s, 1H), 3.99 (s, 1H), 2.42 (m, 1H), 2.17 (s, 3H), 1.83 (s, 1H), 1.56 (m, 4H), 1.38 (s, 3H), 1.22 (s, 3H), 0.97 (s, 3H), 0.58 (s, 3H).

EXAMPLE 11

Preparation of (±)-(5l,1'l)-5-(3-methyl-2-cyclopentenyl)-7,9-difluoro-1,2-dihydro-2,2,4-trimethyl-5H-chromeno[3,4-f]quinoline, (±)-(5l,1'u)-5-(3-methyl-2-cyclopentenyl)-7,9-difluoro-1,2-dihydro-2,2,4-trimethyl-5H-chromeno[3,4-f]quinoline (Compounds 50, 51, Structure 3 of Scheme I, where $R^9=R^{13}=R^{15}=R^{19}=R^{20}=R^{21}=H$, $R^8=R^{10}=$fluorine, $R^6=R^{17}=$methyl, $R^{14}/R^{16}=$a bond, n=0) and (±)-5-(3-methyl-3-cyclopentenyl)-7,9-difluoro-1,2-dihydro-2,2,4-trimethyl-5H-chromeno[3,4-f]quinoline (Compound 52, Structure 3 of Scheme I, where $R^9=R^{13}=R^{14}=R^{15}=R^{20}=R^{21}=H$, $R^8=R^{10}=$fluorine, $R^6=R^{17}=$methyl, $R^{16}/R^{19}=$a bond, n=0)

These compounds were prepared in a similar fashion as that described in Example 1 general procedure from compound 46 (Structure 6 of Scheme I, where $R^{17}=$methyl, $R^{15}=R^{19}=R^{20}=R^{21}=H$, n=0) and compound 36 (Structure 2 of Scheme I, where $R^9=H$, $R^8=R^{10}=$fluorine, $R^6=$methyl).

Compound 50 was isolated as a major product: $^1$H NMR (500 MHz, CDCl$_3$) 7.35 (d, J=8.2, 1H), 7.08 (d, J=9.5, 1H), 6.68 (dt, J=9.6, 2.8, 1H), 6.60 (d, J=8.2, 1H), 5.73 (d, J=8.5, 1H), 5.53 (s, 1H), 5.32 (s, 1H), 4.04 (s, 1H), 2.98 (m, 1H), 2.30 (m, 1H), 2.24 (s, 3H), 2.12 (m, 1H), 1.66 (s, 3H), 1.65 (m, 1H), 1.38 (s, 3H), 1.14 (s, 3H), 0.88 (m, 1H).

Compound 51 was isolated as a minor product: $^1$H NMR (500 MHz, CDCl$_3$) 7.35 (d, J=8.5, 1H), 7.09 (d, J=7.9, 1H), 6.85 (t, 8.5, 1H), 6.60 (d, J=8.2, 1H), 5.68 (d, J=10.4, 1H), 5.48 (s, 1H), 4.79 (s, 1H), 3.99 (s, 1H), 2.95 (m, 1H), 2.36 (m, 1H), 2.18 (m, 1H), 2.14 (s, 3H), 1.94 (m, 1H), 1.65 (s, 3H), 1.38 (s, 3H), 1.20 (s, 3H), 0.88 (m, 1H).

Compound 52 was isolated as minor products: (syn:anti ratio of 2.2:1) $^1$H NMR (500 MHz, CDCl$_3$) 7.33 (d, J=8.6, 1H), 7.10 (dt, J=9.8, 2.8, 1H), 6.69 (td, J=9.5, 2.7, 1H), 6.61 (d, J=8.2, 1H), 5.93 (d, J=8.9, 1H), 5.53 (s, 1H), 5.41 (s, 1H), 4.03 (s, 1H), 2.88 (m, 1H), 2.23 (d, J=0.6, 3H), 2.04 (m, 1H), 1.66 (s, 3H), 1.52 (m, 1H), 1.56 (m, 1H), 1.38 (s, 3H), 1.15 (s, 3H), 0.88 (m, 1H).

EXAMPLE 12

Preparation of (±)-5-(2-cyclopenta-1,3-dienyl)-9-fluoro-1,2-dihydro-2,2,4-trimethyl-5H-chromeno[3,4-f]quinoline (Compound 53, Structure 3 of Scheme I, where $R^8=R^9=R^{15}=R^{17}=R^{20}=H$, $R^{10}=$fluorine, $R^6=$methyl, $R^{13}/R^{14}=$a bond, $R^{19}/R^{21}$ a bond, n=0)

This compound was prepared in a similar fashion as that described in Example 1 general procedure from 5-(dimethylphenylsilyl)-1,3-cyclopentadiene (Compound 54, Structure 6 of Scheme I, where $R^{15}=R^{17}=R^{20}=H$, $R^{19}/R^{21}=$a bond, n=0) and compound 26 (Structure 2 of Scheme I, where $R^{10}=$fluorine, $R^6=$methyl, $R^8=R^9=H$) as a yellow solid: $^1$H NMR (500 MHz, CDCl$_3$) 7.37 (d, J=8.2, 1H), 7.23 (dd, J=9.5, 2.8, 1H), 6.79 (dd, J=8.6, 4.9, 1H), 6.74 (td, J=8.4, 2.8, 1H), 6.64 (d, J=8.2, 1H), 6.61 (s, 1H), 6.33 (dd, J=5.2, 1.2, 1H), 6.22 (dt, J=5.2, 1.8, 1H), 5.94 (t, J=1.4, 1H), 5.48 (s, 1H), 3.94 (s, 1H), 3.08 (dd, J=23.8, 1.5, 1H), 2.95 (dd, J=23.8, 1.5, 1H), 2.11 (d, J=1.5, 3H), 1.28 (s, 3H), 1.25 (s, 3H).

EXAMPLE 13

Preparation of (±)-(5l,1'l)-5-(3-ethyl-2-cyclohexenyl)-9-fluoro-1,2-dihydro-2,2,4-trimethyl-5H-chromeno[3,4-f]quinoline and (±)-(5l,1'u)-5-(3-ethyl-2-cyclohexenyl)-9-fluoro-1,2-dihydro-2,2,4-trimethyl-5H-chromeno[3,4-f]quinoline (Compounds 55 and 56, Structure 3 of Scheme I, where $R^8=R^9=R^{13}=R^{15}=R^{18}=R^{19}=R^{20}=R^{21}=H$, $R^{10}=$fluorine, $R^6=$methyl, $R^{17}=$ethyl, $R^{14}/R^{16}=$a bond, n=1)

These compounds were prepared in a similar fashion as that described in Example 1 general procedure from 3-(dimethylphenylsilyl)-3-ethylcyclohexene (Compound 57, Structure 6 of Scheme I, where $R^{17}=$ethyl, $R^{15}=R^{18}=R^{19}=R^{20}=R^{21}=H$, n=1) and compound 26 (Structure 2 of Scheme I, where $R^{10}=$fluorine, $R^6=$methyl, $R^8=R^9=H$).

Compound 55 was isolated as a major product: $^1$H NMR (500 MHz, CDCl$_3$) 7.38 (d, J=8.2, 1H), 7.29 (dd, J=9.8, 3.1, 1H), 6.90 (dd, J=8.9, 4.9, 1H), 6.81 (dt, J=8.2, 2.8, 1H), 6.61 (d, J=8.2, 1H), 5.59 (s, 1H), 5.56 (d, J=9.5, 1H), 5.50 (d, J=0.9, 1H), 4.00 (s, 1H), 2.40 (m, 1H), 2.24 (d, J=0.9, 3H), 1.93 (q, J=6.7, 2H), 1.88 (m, 1H), 1.80 (m, 1H), 1.67 (m, 1H), 1.38 (s, 3H), 1.27 (m, 1H), 1.22 (m, 1H), 1.14 (s, 3H), 0.98 (m, 1H), 0.95 (t, J=7.6, 3H).

Compound 56 was isolated as a minor product: $^1$H NMR (500 MHz, CDCl$_3$) 7.38 (d, J=7.9, 1H), 7.29 (dd, J=9.8, 3.1, 1H), 6.86 (m, 1H), 6.82 (m, 1H), 6.61 (d, J=8.2, 1H), 5.59 (d, J=10.7, 1H), 5.46 (s, 1H), 4.92 (s, 1H), 3.98 (s, 1H), 2.40 (m, 1H), 2.18 (s, 3H), 1.98 (m, 1H), 1.85 (q, J=7.9, 2H), 1.70 (m, 3H), 1.46 (m, 1H), 1.38 (s, 3H), 1.20 (s, 3H), 0.98 (m, 1H), 0.94 (t, J=7.6, 3H).

EXAMPLE 14

Preparation of (±)-(5l,1'l)-5-(3-methyl-2-cyclohexenyl)-7-fluoro-1,2-dihydro-2,2,4-trimethyl-5H-chromeno[3,4-f]quinoline and (±)-(5l,1'u)-5-(3-methyl-2-cyclohexenyl)-7-fluoro-1,2-dihydro-2,2,4-trimethyl-5H-chromeno[3,4-f]quinoline (Compounds 58 and 59, Structure 3 of Scheme I, where $R^9=R^{10}=R^{13}=R^{15}=R^{18}=R^{19}=R^{20}=R^{21}=H$, $R^8=$fluorine, $R^6=R^{17}=$methyl, $R^{14}/R^{16}=$a bond, n=1)

These compounds were prepared in a similar fashion as that described in Example 1 general procedure from 3-(dimethylphenylsilyl)-3-methyl-1-cyclohexene (Structure 6 of Scheme I, where $R^{17}=$methyl, $R^{15}=R^{18}=R^{19}=R^{20}=R^{21}=H$, n=1) and 7-fluoro-1,2-dihydro-2,2,4-trimethyl-5-methoxy-5H-chromeno[3,4-f]quinoline (Compound 60, Structure 2 of Scheme I, where $R^8=$fluorine, $R^6=$methyl, $R^9=R^{10}=H$).

Compound 58 was isolated as a major product: $^1$H NMR (500 MHz, acetone-d$_6$) 7.54 (d, J=8.2, 1H), 7.50 (d, J=7.6, 1H), 6.95 (m, 2H), 6.75 (d, J=8.2, 1H), 5.64 (s, 1H), 5.63 (s, 1H), 5.62 (d, J=9.5, 1H), 5.54 (s, 1H), 2.36 (m, 1H), 2.23 (s, 3H), 1.90 (m, 1H), 1.78 (m, 1H), 1.70 (m, 1H), 1.62 (s, 3H), 1.37 (s, 3H), 1.29 (m, 2H), 1.13 (s, 3H).

Compound 59 was isolated as a minor product: $^1$H NMR (500 MHz, acetone-d$_6$) 7.53 (d, J=8.5, 1H), 7.50 (d, J=6.7, 1H), 6.96 (m, 2H), 6.76 (d, J=8.2, 1H), 5.73 (d, J=10.4, 1H), 5.64 (s, 1H, 5.51 (d, J=1.2, 1H), 4.96 (m, 1H), 2.35 (m, 1H), 2.18 (s, 3H), 1.90 (m, 1H), 1.80 (m, 1H), 1.73 (m, 1H), 1.58 (s, 3H), 1.48 (m, 1H), 1.37 (s, 3H), 1.28 (m, 1H), 1.21 (s, 3H).

EXAMPLE 15

Preparation of (±)-(5l,1'l)-5-(3-ethyl-2-cyclohexenyl)-7,9-difluoro-1,2-dihydro-2,2,4-trimethyl-5H-chromeno[3,4-f]quinoline (Compound 61, Structure 3 of Scheme I, where $R^9=R^{13}=R^{15}=R^{18}=R^{19}=R^{20}=R^{21}=H$, $R^8=R^{10}=$fluorine, $R^6=$methyl, $R^{17}=$ethyl, $R^{14}/R^{16}=$a bond, n=1), (±)-(5l,1'l)-5-(3-ethylidenecyclohexyl)-7,9-difluoro-1,2-dihydro-2,2,4-trimethyl-5H-chromeno[3,4-f]quinoline (Compound 62, Structure 3 of Scheme I, where $R^9=R^{13}=R^{14}=R^{15}=R^{18}=R^{19}=R^{20}=R^{21}=H$, $R^8=R^{10}=$fluorine, $R^6=$methyl, $R^{16}/R^{17}=$ethylidene, n=1) and (±)-(5l,1'u)-5-(3-ethylidenecyclohexyl)-7,9-difluoro-1,2-dihydro-2,2,4-trimethyl-5H-chromeno[3,4-f]quinoline (Compound 88, Structure 3 of Scheme I, where $R^9=R^{13}=R^{14}=R^{15}=R^{18}=R^{19}=R^{20}=R^{21}=H$, $R^8=R^{10}=$fluorine, $R^6=$methyl, $R^{16}/R^{17}=$ethylide, n=1)

These compounds were prepared in a similar fashion as that described in Example 1 general procedure from compound 57 (Structure 6 of Scheme I, where $R^{17}=$ethyl, $R^{15}=R^{18}=R^{19}=R^{20}=R^{21}=H$, n=1) and compound 36 (Structure 5 of Scheme II, where $R^8=R^{10}=$fluorine, $R^6=$methyl, $R^9=H$).

Compound 61 was isolated as a major product: $^1$H NMR (500 MHz, CD$_3$COCD$_3$) 7.54 (d, J=8.2, 1H), 7.31 (dt, J=8.9, 1.8, 1H), 6.83 (td, 9.4, 3.0, 1H), 6.76 (d, J=8.2, 1H), 5.72 (m, 2H), 5.55 (d, J=4.9, 1H), 5.53 (s, 1H), 2.80 (s, 3H), 2.36 (m, 1H), 2.22 (s, 3H), 1.90 (q, J=7.6, 2H), 1.82 (m, 1H), 1.72 (m, 1H), 1.30 (m, 1H), 1.37 (s, 3H), 1.14 (s, 3H), 0.90 (t, J=7.6, 3H).

Compound 62 was isolated as a minor product: $^1$H NMR (500 MHz, CD$_3$COCD$_3$) 7.51 (d, J=8.2, 1H), 7.30 (dt, J=10.1, 2.8, 1H), 6.83 (td, 9.6, 2.8, 1H), 6.75 (d, J=8.6, 1H), 5.87 (d, J=10.1, 1H), 5.71 (s, 1H), 5.57 (d, J=1.5, 1H), 5.03 (m, 1H), 2.84 (s, 3H), 2.39 (m, 1H), 2.16 (m, 1H), 2.22 (m, 1H), 1.90 (m, 2H), 1.82 (m, 1H), 1.70 (m, 1H), 1.60 (m, 1H), 1.50 (m, 1H), 1.38 (s, 3H), 1.14 (s, 3H), 0.83 (d, J=7.3, 3H).

Compound 88 was isolated as a 1:1 mixture of two E/Z-isomers: $^1$H NMR (500 MHz, acetone-d$_6$) 7.50 (d, J=8.5, 1H), 7.49 (d, J=8.5, 1H), 7.34–7.24 (m, 2H), 6.90–6.80 (m, 2H), 6.64 (d, J=8.5, 1H), 6.61 (d, J=8.5, 1H), 5.86 (d, J=7.9, 1H), 5.80 (d, J=7.9, 1H), 5.49 (s, 1H), 5.36 (s, 1H), 5.34 (s, 1H), 5.22 (s, 1H), 5.16 (s, 1H), 4.79 (s, 1H), 2.44–2.38 (m, 1H), 2.34–2.28 (m, 1H), 2.25 (s, 3H), 2.23 (s, 3H), 1.90–1.74 (m, 6H), 1.68–1.58 (m, 2H), 1.34 (s, 3H), 1.30 (s, 3H), 1.36–1.22 (m, 8H), 1.22 (s, 3H), 1.18 (s, 3H), 0.92–0.84 (m, 6H).

EXAMPLE 16

Preparation of (±)-(5l,1'l)-5-(3-methyl-3-cyclohexenyl)-7,9-difluoro-1,2-dihydro-2,2,4-trimethyl-5H-chromeno[3,4-f]quinoline (Compound 63, Structure 3 of Scheme I, where $R^9=R^{13}=R^{14}=R^{15}=R^{19}=R^{20}=R^{21}=H$, $R^8=R^{10}=$fluorine, $R^6=R^{17}=$methyl, $R^{16}/R^{18}=$a bond, n=1)

This compound was isolated as a minor product after treatment of compound 34 (Structure 3 of Scheme I, where $R^9=R^{13}=R^{15}=R^{18}=R^{19}=R^{20}=R^{21}=H$, $R^8=R^{10}=$fluorine, $R^6=R^{17}=$methyl, $R^{14}/R^{16}=$a bond, n=1) with acid: $^1$H NMR (500 MHz, CDCl$_3$) 7.33 (d, J=8.5, 1H), 7.10 (d, J=10.1, 1H), 6.70 (td, J=10.4, 2.4, 1H), 6.60 (d, J=8.5, 1H), 6.01 (d, J=7.9, 1H), 5.51 (s, 1H), 5.47 (s, 1H), 4.04 (s, 1H), 2.41 (m, 1H), 2.24 (s, 3H), 1.95 (m, 2H), 1.86 (s, 3H), 1.52 (m, 1H), 1.38 (s, 3H), 1.18 (m, 1H), 1.14 (s, 3H), 1.12 (m, 1H), 0.97 (m, 1H).

EXAMPLE 17

Preparation of (±)-(5l,1'l)-5-(3-methyl-2-cyclohexenyl)-9-fluoro-1,2-dihydro-8-methoxy-2,2,4-trimethyl-5H-chromeno[3,4-f]quinoline and (±)-(5l,1'u)-5-(3-methyl-2-cyclohexenyl)-9-fluoro-1,2-dihydro-8-methoxy-2,2,4-trimethyl-5H-chromeno[3,4-f]quinoline (Compounds 64 and 65, Structure 3 of Scheme I, where $R^8=R^{13}=R^{15}=R^{18}=R^{19}=R^{20}=R^{21}=H$, $R^9=$methoxy, $R^6=R^{17}=$methyl, $R^{10}=$fluorine, $R^{14}/R^{16}=$a bond, n=1)

These compounds were prepared in a similar fashion as that described in Example 1 general procedure from 3-(dimethylphenylsilyl)-3-methyl-1-cyclohexene (Structure 6 of Scheme I, where $R^{17}=$methyl, $R^{15}=R^{18}=R^{19}=R^{20}=R^{21}=H$, n=1) and 9-fluoro-1,2-dihydro-5,8-dimethoxy-2,2,4-trimethyl-5H-chromeno[3,4-f]quinoline (Compound 66, Structure 2 of Scheme I, where $R^8=H$, $R^6=$methyl, $R^9=$methoxy, $R^{10}=$fluorine).

Compound 64 was isolated as a major product: $^1$H NMR (500 MHz, CD$_3$COCD$_3$) 7.44 (d, J=12.5, 1H), 7.42 (d, J=8.2, 1H), 6.73 (d, J=6.6, 1H), 6.71 (d, J=7.2, 1H), 5.68 (s, 1H), 5.52 (m, 2H), 5.48 (s, 1H), 3.90 (s, 3H), 2.40 (m, 1H), 2.20 (s, 3H), 2.08 (m, 1H), 1.96 (m, 1H), 1.78 (m, 1H), 1.65 (m, 1H), 1.63 (s, 3H), 1.36 (s, 3H), 1.26 (m, 2H), 1.12 (s, 3H).

Compound 65 was isolated as a minor product: $^1$H NMR (500 MHz, CD$_3$COCD$_3$) 7.44 (d, J=12.5, 1H), 7.42 (d, J=8.2, 1H), 6.73 (d, J=8.2, 1H), 6.70 (d, J=7.6, 1H), 5.63 (s, 1H), 5.48 (s, 1H), 5.46 (d, J=12.5, 1H), 4.96 (m, 1H), 3.88 (s, 3H), 2.39 (m, 1H), 2.20 (s, 3H), 1.94 (m, 1H), 1.78 (m, 1H), 1.72 (m, 1H), 1.57 (s, 3H), 1.46 (m, 1H), 1.36 (s, 3H), 1.28 (m, 2H), 1.20 (s, 3H).

EXAMPLE 18

Preparation of (±)-(5l,1'l)-5-(2-cyclopentenyl)-7,9-difluoro-1,2-dihydro-2,2,4-trimethyl-5H-chromeno[3,4-f]quinoline, (±)-(5l,1'u)-5-(2-cyclopentenyl)-7,9-difluoro-1,2-dihydro-2,2,4-trimethyl-5H-chromeno[3,4-f]quinoline (Compounds 67, 68, Structure 3 of Scheme I, where $R^9=R^{13}=R^{15}=R^{17}=R^{19}=R^{20}=R^{21}=H$, $R^8=R^{10}=$fluorine, $R^6=$methyl, $R^{14}/R^{16}=$a bond, n=0) and (±)-5-(1-cyclopentenyl)-7,9-difluoro-1,2-dihydro-2,2,4-trimethyl-5H-chromeno[3,4-f]quinoline (Compound 69, Structure 3 of Scheme I, where $R^9=R^{15}=R^{16}=R^{17}=R^{19}=R^{20}=R^{21}=H$, $R^8=R^{10}=$fluorine, $R^6=$methyl, $R^{13}/R^{14}=$a bond, n=0)

These compounds were prepared in a similar fashion as that described in Example 1 general procedure from 3-(dimethylphenylsilyl)cyclopentene (Compound 70, Structure 6 of Scheme I, where $R^{15}=R^{17}=R^{19}=R^{20}=R^{21}=H$, n=0) and compound 36 (Structure 2 of Scheme I, where $R^8=R^{10}=$fluorine, $R^6=$methyl, $R^9=H$).

Compound 61 was isolated as a major product: $^1$H NMR (500 MHz, CDCl$_3$) 7.37 (d, J=8.2, 1H), 7.10 (dt, J=9.5, 2.7, 1H), 6.71 (td, J=9.5, 3.1, 1H), 6.61 (d, J=8.2, 1H), 5.77 (ddd, 1H), 5.71 (d, J=10.4, 1H), 5.48 (d, J=1.2, 1H), 5.23 (ddd, 1H), 5.53 (s, 1H), 4.02 (s, 1H), 3.01 (m, 1H), 2.46 (m, 1H), 2.28 (m, 1H), 2.07 (m, 1H), 1.95 (m, 1H), 1.39 (s, 3H), 1.28 (m, 2H), 1.19 (s, 3H).

Compound 62 was isolated as a minor product: $^1$H NMR (500 MHz, CDCl$_3$) 7.37 (d, J=8.2, 1H), 7.09 (dt, J=9.8, 1.8, 1H), 6.69 (td, J=9.6, 2.8, 1H), 6.61 (d, J=8.6, 1H), 5.78 (m, 1H), 5.77 (s, 1H), 5.75 (s, 1H), 5.74 (m, 1H), 5.53 (s, 1H), 4.05 (s, 1H), 2.93 (m, 1H), 2.38 (m, 1H), 2.24 (d, J=0.9, 3H), 1.63 (m, 2H), 1.39 (s, 3H), 1.15 (s, 3H).

Compound 63 was isolated as a minor product: $^1$H NMR (500 MHz, CDCl$_3$) 7.31 (d, J=8.6, 1H), 7.04 (m, 1H), 6.66 (m, 1H), 6.61 (d, J=8.6, 1H), 6.31 (m, 1H), 5.49 (m, 1H), 5.16 (q, J=1.8, 1H), 3.96 (s, 1H), 2.52 (m, 1H), 2.35 (m, 1H), 2.18 (s, 3H), 1.85 (m, 1H), 1.78 (m, 1H), 1.29 (d, J=20.8, 3H), 1.16 (m, 2H), 1.15 (s, 3H).

EXAMPLE 19

Preparation of (±)-(5l,1'l)-5-(2,3-dimethyl-2-cyclopentenyl)-7,9-difluoro-1,2-dihydro-2,2,4-trimethyl-5H-chromeno[3,4-f]quinoline (Compound 71, Structure 3 of Scheme I, where $R^9=R^{13}=R^{19}=R^{20}=R^{21}=H$, $R^8=R^{10}=$fluorine, $R^6=R^{15}=R^{17}=$methyl, $R^{14}/R^{16}=$a bond, n=0)

This compound was prepared in a similar fashion as that described in Example 1 general procedure from 3-(dimethylphenylsilyl)-2,3-dimethylcyclopentene (Compound 72, Structure 6 of Scheme I, where $R^{19}=R^{20}=R^{21}=H$, $R^{15}=R^{17}=$methyl, n=0) and compound 36 (Structure 2 of Scheme I, where $R^8=R^{10}=$fluorine, $R^6=$methyl, $R^9=$H) as a yellow solid: $^1$H NMR (500 MHz, CDCl$_3$) 7.32 (d, J=8.2, 1H), 7.09 (dt, J=9.8, 2.7, 1H), 6.69 (td, J=10.8, 2.8, 1H), 6.59 (d, J=7.5, 1H), 5.92 (d, J=8.2, 1H), 5.53 (s, 1H), 4.01 (s, 1H), 2.86 (m, 1H), 2.29 (m, 1H), 2.22 (s, 3H), 2.00 (m, 1H), 1.57 (s, 3H), 1.55 (s, 3H), 1.50 (m, 1H), 1.38 (s, 3H), 1.14 (s, 3H).

EXAMPLE 20

Preparation of (+)-(5l,1'l)-5-(2,3-dimethyl-2-cyclopentenyl)-7,9-difluoro-1,2-dihydro-2,2,4-trimethyl-5H-chromeno[3,4-f]quinoline and (−)-(5l,1'l)-5-(2,3-dimethyl-2-cyclopentenyl)-7,9-difluoro-1,2-dihydro-2,2,4-trimethyl-5H-chromeno[3,4-f]quinoline (Compounds 73 and 74, Structure 3 of Scheme I, where $R^9=R^{13}=R^{19}=R^{20}=R^{21}=H$, $R^8=R^{10}=$fluorine, $R^6=R^{15}=R^{17}=$methyl, $R^{14}/R^{16}=$a bond, n=0)

These compounds were obtained through chiral HPLC separation of compound 71 using a Chiral AD Semiprep Column, 250×20 mm ID, 90% Hexanes/EtOH. Data for compound 73, $[\alpha]^{22}_D=+256.7$ and compound 74, $[\alpha]^{22}_D=-263.8$ (EtOH).

EXAMPLE 21

Preparation of (±)-(5l,1'l)-5-(2-cyclohexenyl)-7,9-difluoro-1,2-dihydro-2,2,4-trimethyl-5H-chromeno[3,4-f]quinoline, (±)-(5l,1'u)-5-(2-cyclohexenyl)-7,9-difluoro-1,2-dihydro-2,2,4-trimethyl-5H-chromeno[3,4-f]quinoline (Compounds 75 and 76, Structure 3 of Scheme I, where $R^9=R^{15}=R^{16}=R^{17}=R^{18}=R^{19}=R^{20}=R^{21}=H$, $R^8=R^{10}=$fluorine $R^6=$methyl, $R^{13}/R^{14}=$a bond, n=1) and (±)-(5l,1'l-5-(2-cyclohexenyl)-7,9-difluoro-1,2,3,4-tetrahydro-2,2-dimethyl-4-methylidene-5H-chromeno[3,4-f]quinoline (Compound 77, Structure 4 of Scheme I, where $R^4=R^{17}=H$, X=O)

These compounds were prepared in a similar fashion as that described in Example 1 general procedure from 3-(dimethylphenylsilyl)cyclohexene (Compound 78, Structure 6 of Scheme I, where $R^{15}=R^{17}=R^{18}=R^{19}=R^{20}=R^{21}=H$, n=1) and compound 36 (Structure 2 of Scheme I, where $R^8=R^{10}=$fluorine, $R^6=$methyl, $R^9=$H).

Compound 75 was isolated as a major product: $^1$H NMR (500 MHz, CDCl$_3$) 7.35 (d, J=8.2, 1H), 7.08 (td, J=9.8, 1.8, 1H), 6.69 (dt, J=9.5, 3.0, 1H), 6.61 (d, J=8.2, 1H), 5.90 (d, J=11.0, 1H), 5.76 (m, 1H), 5.68 (d, J=9.5, 1H), 5.52 (d, J=1.2, 1H), 4.06 (s, 1H), 2.41 (m, 1H), 2.24 (d, J=1, 3H), 1.94 (m, 2H), 1.66 (m, 2H), 1.39 (s, 3H), 1.28 (m, 1H), 1.25 (m, 1H), 1.14 (s, 3H).

Compound 76 was isolated as a minor product: $^1$H NMR (500 MHz, CDCl$_3$) 7.35 (d, J=8.2, 1H), 7.10 (td, J=9.8, 1.8, 1H), 6.70 (dt, J=8.6, 2.7, 1H), 6.60 (d, J=8.2, 1H), 5.78 (d, J=10.4, 1H), 5.68 (m, 1H), 5.48 (s, 1H), 5.12 (d, J=7.9, 1H), 4.04 (s, 1H), 2.41 (m, 1H), 2.20 (s, 3H), 1.98 (m, 2H), 1.78 (m, 2H), 1.38 (s, 3H), 1.28 (m, 1H), 1.25 (m, 1H), 1.18 (s, 3H).

Compound 77 was isolated as a minor product: $^1$H NMR (500 MHz, CDCl$_3$) 7.31 (d, J=8.6, 1H), 7.08 (m, 1H), 6.68 (m, 1H), 6.43 (d, J=8.2, 1H), 5.85 (m, 1H), 5.73 (m, 1H), 5.40 (s, 1H), 5.18 (s, 1H), 4.04 (s, 1H), 2.33 (d, J=11.3, 1H), 2.27 (d, J=12.2, 1H), 2.00 (m, 1H), 1.93 (m, 1H), 1.68 (m, 1H), 1.94 (m, 2H), 1.34 (s, 3H), 1.18 (m, 1H), 1.14 (s, 3H), 0.86 (m, 2H).

EXAMPLE 22

Preparation of (±)-(5l,1'l)-5-(2-methylidenecyclohexyl)-9-fluoro-1,2-dihydro-2,2,4-trimethyl-5H-chromeno[3,4-f]quinoline and (±)-(5l,1'u)-5-(2-methylidenecyclohexyl)-9-fluoro-1,2-dihydro-2,2,4-trimethyl-5H-chromeno[3,4-f]quinoline (Compounds 79 and 80, Structure 3 of Scheme I, where $R^8=R^9=R^{13}=R^{16}=R^{17}=R^{18}=R^{19}=R^{20}=R^{21}=H$, $R^{10}=$fluorine, $R^6=$methyl, $R^{14}/R^{15}=$methylidene, n=1)

(±)-(5l,1'l)-5-(2-oxocyclohexyl)-9-fluoro-1,2-dihydro-2,2,4-trimethyl-5H-chromeno[3,4-f]quinoline and (±)-(5l,1'u)-5-(2-oxocyclohexyl)-9-fluoro-1,2-dihydro-2,2,4-trimethyl-5H-chromeno[3,4-f]quinoline (Compounds 81 and 82, Structure 3 of Scheme I, where $R^8=R^9=R^{13}=R^{16}=R^{17}=R^{18}=R^{19}=R^{20}=R^{21}=H$, $R^{10}=$fluorine, $R^6=$methyl, $R^{14}/R^{15}=$carbonyl, n=1)

Compounds 81 and 82 were prepared in a similar fashion as that described in Example 1 general procedure from 1-(trimethylsilyloxy)cyclohexene and compound 26 (Structure 2 of Scheme I, where $R^{10}=$fluorine, $R^6=$methyl, $R^8=R^9=$H).

Compound 81 was isolated as a major product: $^1$H NMR (500 MHz, CDCl$_3$) 7.36 (d, J=8.6, 1H), 7.30 (dd, J=13.4, 4.6, 1H), 6.81 (d, J=7.0, 1H), 6.80 (d, J=8.2, 1H), 6.61 (d, J=8.5, 1H), 6.58 (d, J=9.2, 1H), 5.49 (s, 1H), 3.99 (s, 1H), 2.84 (m, 1H), 2.45 (m, 1H), 2.28 (s, 3H), 2.24 (m, 1H), 1.99 (m, 1H), 1.68 (m, 2H), 1.40 (m, 2H), 1.37 (s, 3H), 1.11 (s, 3H).

Compound 82 was isolated as a minor product: $^1$H NMR (500 MHz, CDCl$_3$) 7.36 (d, J=8.6, 1H), 7.30 (dd, J=7.3, 1H), 6.81 (d, J=8.8, 1H), 6.79 (d, J=7.6, 1H), 6.59 (d, J=8.2, 1H), 6.44 (d, J=5.8, 1H), 5.49 (s, 1H), 3.99 (s, 1H), 2.59 (m, 1H), 2.35 (m, 1H), 2.26 (s, 3H), 2.20 (m, 1H), 1.90 (m, 2H), 1.80 (m, 1H), 1.70 (m, 2H), 1.45 (m, 2H), 1.37 (s, 3H), 1.12 (s, 3H).

The title compounds 79 and 80 were prepared by using a Wittig procedure from compounds 81 and 82. Data for compound 79: $^1$H NMR (500 MHz, CDCl$_3$) 7.38 (d, J=8.2, 1H), 7.31 (dd, J=7.6, 2.8, 1H), 6.78 (m, 1H), 6.80 (d, J=8.2, 1H), 6.61 (m, 1H), 6.02 (d, J=10.1, 1H), 5.52 (s, 1H), 4.83 (s, 1H), 4.71 (s, 1H), 4.02 (s, 1H), 2.50 (m, 1H), 2.42 (s, 3H), 2.30 (m, 1H), 2.07 (m, 1H), 1.60 m, m1H), 1.45 (m, 2H), 1.39 (s, 3H), 1.30 (m, 1H), 1.18 (m, 1H), 1.12 (s, 3H, 1.08 (m, 1H). Data for compound 80: $^1$H NMR (500 MHz, CDCl$_3$) 7.38 (d, J=8.8, 1H), 7.34 (m, 1H), 6.78 (m, 1H), 6.86 (m, 1H), 6.54 (d, J=8.9, 1H), 6.01 (d, J=9.2, 1H), 5.47 (s, 1H), 4.41 (s, 1H), 4.10 (s, 1H), 3.98 (s, 1H), 2.56 (m, 1H), 2.30 (s, 3H), 2.04 (m, 3H), 1.76 (m, 1H), 1.68 (m, 1H), 1.58 (m, 1H), 1.36 (s, 3H), 1.30 (m, 2H), 1.09 (s, 3H).

EXAMPLE 23

Preparation of (±)-(5l,1'l)-5-(3-methyl-2-cyclohexenyl)-9-methoxy-1,2-dihydro-1,2,2,4-tetramethyl-5H-chromeno[3,4-f]quinoline (Compound 83, Structure 5 of Scheme I)

This compound was prepared by methylation of compound 39 (Structure 3 of Scheme I, where $R^8=R^9=R^{13}=R^{15}=R^{18}=R^{19}=R^{20}=R^{21}=H$, $R^{10}=$methoxy, $R^6=R^{17}=$methyl, $R^{14}/R^{16}=$a bond, n=1) as a yellow solid: $^1$H NMR (500 MHz, CDCl$_3$) 7.56 (d, J=8.5, 1H), 7.28 (d, J=2.1, 1H), 6.92 (d, J=8.9, 1H), 6.75 (m, 2H), 5.69 (s, 1H), 5.54 (s, 1H), 5.50 (d, J=9.8, 1H), 3.83 (s, 3H), 2.89 (s, 3 H), 2.41 (m, 1H), 2.26 (s, 3H), 1.87 (m, 1H), 1.77 (m, 1H), 1.66 (s, 3H), 1.62 (m, 1H), 1.51 (s, 3H), 1.28 (m, 2H), 1.18 (m, 1H), 0.96 (s, 3H).

EXAMPLE 24

Preparation of (±)-5-(2-cyclohexenyl)-9-fluoro-1,2-dihydro-2,2,4-trimethyl-5H-chromeno[3,4-f]quinoline (Compounds 84, Structure 3 of Scheme I, where $R^8=R^9=R^{13}=R^{15}=R^{17}=R^{18}=R^{19}=R^{20}=R^{21}=H$, $R^{10}=F$, $R^6$=methyl, $R^{14}/R^{16}$=a bond, n=1)

This compound was prepared in a similar fashion as that described in Example 1 general procedure from 3-(dimethylphenylsilyl)cyclohexene (Compound 78, Structure 6 of Scheme I, where $R^{15}=R^{17}=R^{18}=R^{20}=R^{21}=H$, n=1) and compound 26 (Structure 2 of Scheme I, where $R^{10}$=fluorine, $R^6$=methyl, $R^8=R^9$=H) as a 1:1 mixture of two diastereomers: $^1$H NMR (500 MHz, CDCl$_3$) 7.38 (d, J=8.2, 1H), 7.38 (d, J=8.2, 1H), 7.30 (t, J=2.8, 1H), 7.28 (t, J=2.8, 1H), 6.90–6.85 (m, 2H), 6.85–6.80 (m, 2H), 6.61 (d, J=8.2, 1H), 6.61 (d, J=8.2, 1H), 5.91 (d, J=10.1, 1H), 5.78–5.71 (m, 1H), 5.67 (d, J=10.1, 1H), 5.70–5.64 (m, 1H), 5.57 (d, J=9.8, 1H), 5.51 (s, 1H), 5.47 (s, 1H), 5.18–5.14 (m, 1H), 4.02–3.98 (m, 2H), 2.46–2.38 (m, 1H), 2.24 (s, 3H), 2.20 (s, 3H), 2.04–1.90 (m, 4H), 1.80–1.70 (m, 3H), 1.68–1.62 (m, 1H), 1.48–1.42 (m, 1H), 1.49 (s, 3H), 1.47 (s, 3H), 1.32–1.22 (m, 2H), 1.16 (s, 3H), 1.14 (s, 3H), 0.98–0.92 (m, 2H).

EXAMPLE 25

Preparation of (±)-(5l,1'l)-5-(2,3-dimethyl-2-cyclohexenyl)-7,9-difluoro-1,2-dihydro-2,2,4-trimethyl-5H-chromeno[3,4-f]quinoline (Compound 85, Structure 3 of Scheme I, where $R^9=R^{13}=R^{18}=R^{19}=R^{20}=R^{21}=H$, $R^8=R^{10}$=fluorine, $R^6=R^{15}=R^{17}$=methyl, $R^{14}/R^{16}$=a bond, n=1)

This compound was prepared in a similar fashion as that described in Example 1 general procedure from 3-(dimethylphenylsilyl)-2,3-dimethylcyclohexene (Compound 86, Structure 6 of Scheme I, where $R^{18}=R^{19}=R^{20}=R^{21}=H$, $R^{15}=R^{17}$=methyl, n=1) and Compound 36 (Structure 2 of Scheme I, where $R^8=R^{10}$=fluorine, $R^9$=H, $R^6$=methyl) as a yellow solid: $^1$H NMR (500 MHz, acetone-d$_6$) 7.50 (d, J=8.2, 1H), 7.30 (dt, J=10.1, 1.8, 1H), 6.84 (td, J=9.8, 2.8, 1H), 6.75 (d, J=8.2, 1H), 6.01 (d, J=6.4, 1H), 5.72 (s, 1H), 5.55 (d, 1.2, 1H), 2.30 (m, 1H), 2.22 (s, 3H), 2.00–1.8 (m, 3H), 1.59 (s, 3H), 1.50 (s, 3H), 1.46–1.40 (m, 1H), 1.37 (s, 3H), 1.36–1.26 (m, 3H), 1.15 (s, 3H).

EXAMPLE 26

Preparation of (±)-(5l,1'l)-5-(2-cycloheptenyl)-7,9-difluoro-1,2-dihydro-2,2,4-trimethyl-5H-chromeno[3,4-f] quinoline (Compound 89, Structure 3 of Scheme I, where $R^9=R^{13}=R^{15}=R^{17}=R^{18}=R^{19}=R^{20}=R^{21}=H$, $R^8=R^{10}$=fluorine, $R^6$=methyl, $R^{14}/R^{16}$=a bond, n=2)

This compound was prepared in a similar fashion as that described in Example 1 general procedure from 3-(dimethylphenylsilyl)cycloheptene (Compound 90, Structure 6 of Scheme I, where $R^{15}=R^{17}=R^{18}=R^{19}=R^{20}=R^{21}=H$, n=2) and Compound 36 (Structure 2 of Scheme I, where $R^8=R^{10}$=fluorine, $R^9$=H, $R^6$=methyl) as a yellow solid: $^1$H NMR (500 MHz, CDCl$_3$) 7.36 (d, J=8.6, 1H), 7.10 (d, J=9.8, 1H), 6.68 (ddd, J=9.5, 2.8, 2.8, 1H), 6.61 (d, J=8.2, 1H), 6.03 (d, J=11.6, 1H), 5.84–5.76 (m, 1H), 5.80 (d, J=10.1, 1H), 5.52 (s, 1H), 4.10 (s, 1H), 2.47 (m, 1H), 2.24 (s, 3H), 2.12–2.04 (m, 2H), 1.94–1.84 (m, 1H), 1.78–1.84 (m, 1H), 1.44–1.44 (m, 1H), 1.38 (s, 3H), 1.24–1.18 (m, 2H), 1.11 (s, 3H), 0.98–0.92 (m, 1H).

EXAMPLE 27

Preparation of (±)-(5l,1'l)-5-(2-cyclooctenyl)-7,9-difluoro-1,2-dihydro-2,2,4-trimethyl-5H-chromeno[3,4-f] quinoline and (±)-(5l,1'u)-5-(2-cyclooctenyl)-7,9-difluoro-1,2-dihydro-2,2,4-trimethyl-5H-chromeno[3,4-f]quinoline (Compounds 91 and 92, Structure 3 of Scheme I, where $R^9=R^{13}=R^{15}=R^{17}=R^{18}=R^{19}=R^{20}=R^{21}=H$, $R^8=R^{10}$=fluorine, $R^6$=methyl, $R^{14}/R^{16}$=a bond, n=3)

These compounds were prepared in a similar fashion as that described in Example 1 general procedure from 3-(dimethylphenylsilyl)cyclooctene (Compound 93, Structure 6 of Scheme I, where $R^{13}=R^{15}=R^{17}=R^{18}=R^{19}=R^{20}=R^{21}=H$, n=3) and Compound 36 (Structure 2 of Scheme I, where $R^8=R^{10}$=fluorine, $R^9$=H, $R^6$=methyl) as a yellow solid: Compound 91 $^1$H NMR (500 MHz, CDCl$_3$) 7.36 (d, J=8.6, 1H), 7.10 (d, J=9.8, 1H), 6.68 (ddd, J=9.5, 2.8, 2.8, 1H), 6.58 (d, J=8.2, 1H), 5.87 (d, J=9.5, 1H), 5.74–5.66 (m, 1H), 5.56 (t, J=10.1, 1H), 5.52 (s, 1H), 4.03 (s, 1H), 2.90–2.80 (m, 1H), 2.26 (s, 3H), 1.88–1.80 (m, 1H), 1.54–1.46 (m, 2H), 1.40–1.32 (m, 2H), 1.23–1.17 (m, 2H), 1.38 (s, 3H), 1.24–1.18 (m, 2H), 1.19 (s, 3H), 1.07–0.98 (m, 1H); Compound 92 $^1$H NMR (500 MHz, CDCl$_3$) 7.33 (d, J=8.5, 1H), 7.11 (d, J=9.8, 1H), 6.71 (ddd, J=9.5, 2.8, 2.8, 1H), 6.61 (d, J=8.2, 1H), 5.87 (d, J=8.8, 1H), 5.54 (s, 1H), 5.54–5.48 (m, 1H), 5.23 (t, J=10.4, 1H), 4.01 (s, 1H), 2.88–2.80 (m, 1H), 2.26 (s, 3H), 1.96–1.88 (m, 1H), 1.84–1.70 (m, 2H), 1.54–1.46 (m, 2H), 1.45–1.38 (m, 1H), 1.38 (s, 3H), 1.36–1.26–1.17 (m, 2H), 1.20–1.00 (m, 2H), 1.10 (s, 3H).

EXAMPLE 28

Preparation of (±)-(5l,1'l)-5-(2,3-epoxy-3-methylcyclohexyl)-7,9-difluoro-1,2-dihydro-2,2,4-trimethyl-5H-chromeno[3,4-f]quinoline (Compound 94, Structure 3 of Scheme I, where $R^9=R^{13}=R^{15}=R^{18}=R^{19}=R^{20}=R^{21}=H$, $R^8=R^{10}$=fluorine, $R^6=R^{17}$=methyl, $R^{14}/R^{16}$=—O—, n=1) and (±)-(5l,1'l)-5-(3-methyl-2-cyclohexenyl)-7,9-difluoro-1,2,3,4-tetrahydro-2,2-dimethyl-4-methylene-5H-chromeno [3,4-f]quinolin-3-ol (Compound 95, Structure 4 of Scheme I, where $R^4$=hydroxy, $R^{17}$=methyl, X=O)

These compounds were prepared by epoxidation of Compound 34 (Structure 3 of Scheme I, where $R^9=R^{13}=R^{15}=R^{18}=R^{19}=R^{20}=R^{21}=H$, $R^8=R^{10}$=fluorine, $R^6=R^{17}$=methyl, $R^{14}/R^{16}$=a bond, n=1) according to a standard procedure as yellow solids: Compound 94, $^1$H NMR (500 MHz, acetone-d$_6$) 7.54 (d, J=8.5, 1H), 7.35 (ddd, J=9.2, 1.8, 1.8, 1H), 6.89 (ddd, J=9.5, 2.8, 2.8, 1H), 6.76 (d, J=8.5, 1H), 6.02 (d, J=10.1, 1H), 5.74 (s, 1H), 5.54 (s, 1H), 3.15 (d, J=2.1, 1H), 2.28 (d, J=0.6, 3H), 2.16–2.00 (m, 1H), 1.72–1.66 (m, 2H), 1.37 (s, 3H), 1.40–1.28 (m, 1H), 1.28 (s, 3H), 1.11 (s, 3H), 1.08–0.93 (m, 2H), 0.84–0.76 (m, 1H; Compound 95, $^1$H NMR (500 MHz, acetone-d$_6$) 7.48 (d, J=8.5, 1H), 7.28 (ddd, J=9.2, 1.8, 1.8, 1H), 6.83 (ddd, J=9.5, 2.8, 2.8, 1H), 6.60 (d, J=8.5, 1H), 5.80 (d, J=8.8, 1H), 5.70 (d, J=21.4, 1H), 5.68 (s, 1H), 5.55 (s, 1H), 5.41 (s, 1H), 4.55 (d, J=4.9, 1H), 4.18 (dt, J=4.6, 1.2, 1H), 2.30–2.22 (m, 1H), 1.90–1.74 (m, 1H), 1.74–1.66 (m, 1H), 1.58 (s, 3H), 1.35 (s, 3H), 1.32–1.24 (m, 4H), 1.08 (s, 3H).

EXAMPLE 29

Preparation of (±)-(5l,1'l)-5-(2,3-epoxy-2,3-dimethylcyclopentyl)-7,9-difluoro-1,2-dihydro-2,2,4-trimethyl-5H-chromeno[3,4-f]quinoline (Compound 96, Structure 3 of Scheme I, where $R^9=R^{13}=R^{19}=R^{20}=R^{21}=H$, $R^8=R^{10}$=fluorine, $R^6=R^5=R^{17}$=methyl, $R^{14}/R^{15}$=—O—, n=0)

This compound was prepared by epoxidation of Compound 71 (Structure 3 of Scheme I, where $R^9=R^{13}=R^{19}=R^{20}=R^{21}=H$, $R^8=R^{10}$=fluorine, $R^6=R^{15}=R^{17}$=methyl, $R^{14}/R^{16}$=a bond, n=0) as a solid: $^1$H NMR (500 MHz, acetone-$d_6$) 7.49 (d, J=8.5, 1H), 7.34 (ddd, J=9.2, 1.8, 1.8, 1H), 6.89 (ddd, J=9.5, 2.8, 2.8, 1H), 6.73 (d, J=8.6, 1H), 6.18 (d, J=9.5, 1H), 5.68 (s, 1H), 5.53 (s, 1H), 2.35 (dt, J=9.8, 1.8, 1H), 2.28 (d, J=0.6, 3H), 1.69 (dd, J=13.7, 8.2, 1H), 1.48 (s, 3H), 1.47–1.43 (m, 1H), 1.36 (s, 3H), 1.25 (s, 3H), 1.01 (s, 3H), 0.98–0.92 (m, 1H), 0.78–0.72 (m, 1H).

EXAMPLE 30

Preparation of (±)-(5l,1'u)-5-(2,3-epoxy-3-methylcyclohexyl)-7,9-difluoro-1,2-dihydro-2,2,4-trimethyl-5H-chromeno[3,4-f]quinoline (Compound 97, Structure 3 of Scheme I, where $R^9=R^{13}=R^{15}=R^{18}=R^{19}=R^{20}=R^{21}=H$, $R^8=R^{10}$=fluorine, $R^6=R^{17}$=methyl, $R^{14}/R^{16}$=—O—, n=1)

This compound was prepared by epoxidation of Compound 35 (Structure 3 of Scheme I, where $R^9=R^{13}=R^{15}=R^{18}=R^{19}R^{20}R^{21}$'H, $R^8=R^{10}$=fluorine, $R^6=R^{17}$=methyl, $R^{14}/R^{16}$=a bond, n=1) according to a standard procedure as yellow solids: Compound 97, $^1$H NMR (500 MHz, acetone-$d_6$) 7.57 (d, J=8.5, 1H), 7.35 (ddd, J=9.2, 1.8, 1.8, 1H), 6.88 (ddd, J=9.5, 2.8, 2.8, 1H), 6.80 (d, J=8.5, 1H), 5.94 (d, J=10.4, 1H), 5.77 (s, 1H), 5.61 (s, 1H), 2.65 (s, 1H), 2.27 (d, J=0.9, 3H), 2.12–2.06 (m, 1H), 1.86–1.80 (m, 1H), 1.76–1.68 (m, 1H), 1.66–1.58 (m, 1H), 1.46–1.40 (m, 1H), 1.37 (s, 3H), 1.36–1.26 (m, 2H), 1.21 (s, 3H), 1.11 (s, 3H).

EXAMPLE 31

Preparation of (±)-(5l,1'l)-5-(3-methyl-2-cyclohexenyl)-7,9-difluoro-1,2,3,4-tetrahydro-2,2-dimethyl-5H-chromeno[3,4-f]quinolin-4-one (Compound 98, Structure 4 of Scheme I, where $R^4$=H, $R^{17}$=methyl, X=O)

These compounds were prepared in a similar fashion as that described in Example 1 general procedure from 3-(dimethylphenylsilyl)-3-methyl-1-cyclohexene (Structure 6 of Scheme I, where $R^{17}$=methyl, $R^{15}=R^{18}=R^{19}=R^{20}=R^{21}$=H, n=1) and 7,9-difluoro-1,2,3,4-tetrahydro-5-methoxy-2,2-dimethyl-5H-chromeno[3,4-f]quinolin-4-one (Compound 99), $^1$H NMR (500 MHz, CDCl$_3$), 7.55 (d, J=8.9, 1H), 7.02–6.95 (m, 1H), 6.70–6.64 (m, 1H), 6.66 (d, J=8.6, 1H), 6.42 (d, J=5.8, 1H), 5.26 (s, 1H), 4.42 (s, 1H), 2.67 (d, J=15.2, 1H), 2.56 (d, J=15.0, 1H), 2.48 (m, 1H), 1.94–1.80 (m, 2H), 1.78–1.66 (m, 2H), 1.44 (s, 3H), 1.37 (s, 3H), 1.32 (s, 3H), 1.42–1.36 (m, 1H), 1.29–1.25 (m, 1H).

EXAMPLE 32

The in vitro activity of selected hPR modulator compounds of the present invention were evaluated utilizing the cotransfection assay, and in standard receptor competitive binding assays, according to the following illustrative Examples.

Cotransfection Assay

The function and detailed preparation procedure of the cotransfection assays have been described previously (Pathirana, C. et al., Nonsteroidal Human Progesterone Receptor Modulators from the Marine Alga Cymopolia Barbata. *Mol. Pharm.* 1995, 47, 630–635). Briefly, the cotransfection assays were carried out in CV-1 cells (African green monkey kidney fibroblasts), which were transiently transfected, by the standard calcium phosphate coprecipitation procedure (Berger, T. S. et al., Interaction of Glucocorticoid Analogues with the Human Glucocorticoid Receptor. *J. Steroid Biochem. Mol. Bio.* 1992, 41, 733–738) with the Plasmid containing receptor, MTV-LUC reporter, pRS-β-Gal, and filler DNA (*Rous sarcoma* virus chloramphenicol acetyltransferase). The agonist activity was determined by examining the LUC expression (normalized response) and the efficacy readout was a relative value to the maximal LUC expression produced by progesterone. All the cotransfection experiments were carried out in 96-well plates by automation (Beckman Biomomek automated workstation).

Receptor Binding Assays

The preparation of receptor binding assays for hPR-A was described in literature (Pathirana, C. et al., Nonsteroidal Human Progesterone Receptor Modulators from the Marine Alga Cymopolia Barbata. *Mol. Pharm.* 1995, 47, 630–635.)

The agonist, antagonist and binding activity assay results of selected progesterone receptor modulator compounds of the present invention and the standard reference compounds on PR are shown in Table 1 below. Efficacy is reported as the percent maximal response observed for each compound relative to the reference agonist and antagonist compounds indicated above. Also reported in Table 1 for each compound is its antagonist potency or IC$_{50}$ (which is the concentration (nM), required to reduce the maximal response by 50%), and its agonist potency or EC$_{50}$ (nM), which is the effective concentration that produced 50% of the maximum response.

TABLE 1

Agonist, antagonist and binding activity of progesterone receptor modulator compounds of present invention and the reference agonist compound, progesterone (Prog), and reference antagonist compound, RU486 and ZK299.

| Cmpd No. | PR Agonist CV-1 Cells | | PR Antagonist CV-1 Cells | | PR Binding |
|---|---|---|---|---|---|
| | Efficacy (%) | Potency (nM) | Efficacy (%) | Potency (nM) | K$_i$ (nM) |
| Prog | 100 | 2.9 | na | na | 3.5 |
| RU486 | na | na | 96 | 0.18 | 0.58 |
| ZK299 | na | na | 99 | 1.6 | 18 |
| 24 | 168 | 3.6 | na | na | 6.4 |
| 25 | 86 | 9.7 | na | na | 6.3 |
| 27 | 68 | 43 | na | na | 241 |
| 28 | 171 | 0.9 | na | na | 2.0 |
| 34 | 164 | 0.5 | na | na | 3.7 |
| 35 | 100 | 5.4 | na | na | 14 |
| 37 | na | na | 50 | 113 | >1000 |
| 38 | 166 | 0.6 | na | na | 1.9 |
| 41 | 122 | 10 | na | na | 11 |
| 42 | 27 | 38 | na | na | 143 |
| 44 | 123 | 6.7 | na | na | 7.7 |
| 45 | 94 | 9.1 | na | na | 17 |
| 64 | na | na | 80 | 1900 | 485 |
| 65 | na | na | 59 | 650 | 329 |
| 71 | 139 | 3.4 | na | na | 3.9 | na = not active (i.e. efficacy of <20 and potency of >10,000)

EXAMPLE 33

The in vivo activity of selected hPR modulator compounds of the present invention were evaluated utilizing the McPhail assay, according to the following illustrative Examples. The Clauberg or McPhail assay is a classic assay utilizing rabbits to measure progestational activity. The reason rabbit is used is because the results observed in rabbit have proved to be a good indicator and predictor of activity in the human. In this assay, immature rabbits are treated initially with estradiol, which induces growth in the uterus. This is followed by treatment with a progestin, which causes a large change in the glandular content of the uterus. It is this change in the glandular component, which is a measure of the progestational activity of a progestin. The measurement of these glandular changes are carried out histologically using stained sections of the uterus. The assay results of the new 5-cycloalkenyl compounds are tabulated in Table 2. The in vivo potency of the progestins is presented as the minimum active dose (MAD) in mg/kg.

TABLE 2

The potency (MAD in mg/kg) of selected 5-cycloalkenyl compounds of present invention in the McPhail assay.

| Compd # | MAD (mg/kg) | $EC_{50}$(nM) | $k_i$(nM) |
|---|---|---|---|
| 24 | 0.25 | 3.6 | 6.4 |
| 34 | 0.25 | 0.5 | 3.7 |
| 38 | 0.10 | 0.6 | 1.9 |
| 71 | 0.25 | 3.4 | 3.9 |

Pharmacological and Other Applications

The following Example provides illustrative pharmaceutical composition formulations:

EXAMPLE 34

Hard gelatin capsules are prepared using the following ingredients:

| | Quantity (mg/capsule) |
|---|---|
| COMPOUND 24 | 10 |
| Starch, dried | 100 |
| Magnesium stearate | 10 |
| Total | 120 mg |

The above ingredients are mixed and filled into hard gelatin capsules in 120 mg quantities.

A tablet is prepared using the ingredients below:

| | Quantity (mg/tablet) |
|---|---|
| COMPOUND 24 | 10 |
| Cellulose, microcrystalline | 200 |
| Silicon dioxide, fumed | 10 |
| Stearic acid | 10 |
| Total | 230 mg |

The components are blended and compressed to form tablets each weighing 230 mg. Tablets, each containing 10 mg of active ingredient, are made as follows:

| | Quantity (mg/tablet) |
|---|---|
| COMPOUND 24 | 10 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 100 mg |

The active ingredient, starch and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate and talc, previously passed through a No. 60 mesh U.S. sieve are then added to the granules which, after mixing, are compressed on a tablet machine to yield tablets each weighing 150 mg.

Suppositories, each containing 225 mg of active ingredient, may be made as follows:

| | Quantity (mg/suppository) |
|---|---|
| COMPOUND 24 | 20 |
| Saturated fatty acid glycerides | 2,000 |
| Total | 2,020 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

| | Quantity |
|---|---|
| COMPOUND 24 | 10 mg |
| isotonic saline | 1000 mL |
| glycerol | 100 mL |

The compound is dissolved in the glycerol and then the solution is slowly diluted with isotonic saline. The solution of the above ingredients is then administered intravenously at a rate of 1 mL per minute to a patient.

The present invention includes any combination of the various species and subgeneric groupings falling within the generic disclosure. This invention therefore includes the generic description of the invention with a proviso or negative limitation removing any subject matter from the genus, regardless of whether or not the excised material is specifically recited herein.

The scope of the invention is not to be limited by the description of the examples. Modifications and alterations of the present invention will be apparent to those skilled in the art without departing from the scope and spirit of the present invention.

Therefore, it will be appreciated that the scope of this invention is to be defined by the appended claims, rather than by the specific examples which have been presented by way of example.

What is claimed is:

1. A compound of the formula:

(I)

wherein:
- $R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;
- $R^2$ and $R^3$ each independently is selected from the group of hydrogen, $C_1$–$C_6$ alkyl, and $C_1$–$C_6$ haloalkyl; or
- $R^2$ and $R^3$ taken together form a cycloalkyl ring of from three to twelve carbons;
- $R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or
- $R^5$ and $R^7$ taken together form a bond; or
- $R^6$ and $R^7$ taken together are selected from the group of methylidene, mono-substituted methylidene, di-substituted methylidene and carbonyl;
- $R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;
- $R^{11}$ and $R^{12}$ each is independently selected from the group of hydrogen, $C_1$–$C_4$ alkyl, $C_1$–$C_4$ heteroalkyl, and $C_1$–$C_4$ haloalkyl;
- $R^{13}$ is hydrogen;
- $R^{14}$ through $R^{20}$ each independently is selected from the group of hydrogen, F, Cl, Br, $OR^{11}$, $C_1$–$C_4$ alkyl, $C_1$–$C_4$ haloalkyl, and $C_1$–$C_4$ heteroalkyl; or
- $R^{14}$ and $R^{15}$ taken together are selected from the group of methylidene, carbonyl and thiocarbonyl; or
- $R^{16}$ and $R^{17}$ taken together are selected from the group of methylidene, mono-substituted methylidene, di-substituted methylidene, carbonyl and thiocarbonyl; or
- $R^{14}$ and $R^{16}$ taken together form a bond or "—O—" bridge; or
- $R^{16}$ and $R^{18}$ taken together form a bond when n is 1; or
- $R^{16}$ and $R^{19}$ taken together form a bond when n is 0;
- $R^{21}$ is hydrogen; or
- $R^{21}$ and $R^{20}$ taken together form a bond;
- n is 0, 1, 2, or 3;

or a pharmaceutically acceptable salt thereof.

2. A compound of the formula:

(I)

wherein:
- $R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;
- $R^2$ and $R^3$ each independently is selected from the group of hydrogen, $C_1$–$C_6$ alkyl, and $C_1$–$C_6$ haloalkyl; or
- $R^2$ and $R^3$ taken together form a cycloalkyl ring of from three to twelve carbons;
- $R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or
- $R^5$ and $R^7$ taken together form a bond; or
- $R^6$ and $R^7$ taken together are selected from the group of methylidene, mono-substituted methylidene, di-substituted methylidene and carbonyl;
- $R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;
- $R^{11}$ and $R^{12}$ each is independently selected from the group of hydrogen, $C_1$–$C_4$ alkyl, $C_1$–$C_4$ heteroalkyl, and $C_1$–$C_4$ haloalkyl;
- $R^{13}$ is hydrogen; or
- $R^{13}$ and $R^{14}$ taken together form a bond;
- $R^{14}$ through $R^{20}$ each independently is selected from the group of hydrogen, F, Cl, Br, $OR^{11}$, $C_1$–$C_4$ alkyl, $C_1$–$C_4$ haloalkyl, and $C_1$–$C_4$ heteroalkyl; or
- $R^{14}$ and $R^{15}$ taken together are selected from the group of methylidene, carbonyl and thiocarbonyl; or
- $R^{16}$ and $R^{17}$ taken together are selected from the group of methylidene, mono-substituted methylidene, di-substituted methylidene, carbonyl and thiocarbonyl; or
- $R^{14}$ and $R^{16}$ taken together form a bond or "—O—" bridge;
- $R^{16}$ and $R^{19}$ taken together form a bond when n is 0;
- $R^{21}$ is hydrogen; or
- $R^{21}$ and $R^{20}$ taken together form a bond;
- n is 0, 1, 2, or 3;

or a pharmaceutically acceptable salt thereof.

3. A compound of the formula:

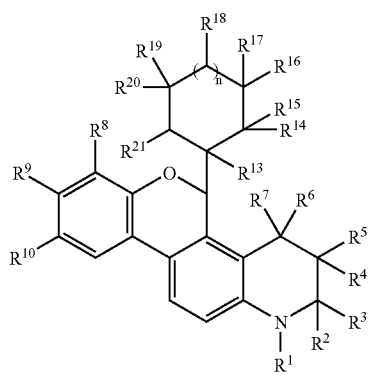

wherein:
R$^1$ is selected from the group of hydrogen, C$_1$–C$_4$ alkyl, C$_1$–C$_4$ haloalkyl, C$_1$–C$_4$ heteroalkyl, COR$^{11}$, CO$_2$R$^{11}$, SO$_2$R$^{11}$, and CONR$^{11}$R$^{12}$;
R$^2$ and R$^3$ each independently is selected from the group of hydrogen, C$_1$–C$_6$ alkyl, and C$_1$–C$_6$ haloalkyl; or
R$^2$ and R$^3$ taken together form a cycloalkyl ring of from three to twelve carbons;
R$^4$ through R$^7$ each independently is selected from the group of hydrogen, F, Cl, Br, CN, OR$^{11}$, C$_1$–C$_4$ alkyl, C$_1$–C$_4$ haloalkyl, and C$_1$–C$_4$ heteroalkyl; or
R$^5$ and R$^7$ taken together form a bond; or
R$^6$ and R$^7$ taken together are selected from the group of methylidene, mono-substituted methylidene, di-substituted methylidene and carbonyl;
R$^8$ through R$^{10}$ each independently is selected from the group of hydrogen, F, Cl, Br, I, NO$_2$, CN, OR$^{11}$, NR$^{11}$R$^{12}$, SR$^{11}$, COR$^{11}$, CO$_2$R$^{11}$, CONR$^{11}$R$^{12}$, C$_1$–C$_8$ alkyl, C$_1$–C$_8$ heteroalkyl, C$_1$–C$_8$ haloalkyl, allyl, C$_2$–C$_8$ alkenyl and C$_2$–C$_8$ alkynyl;
R$^{11}$ and R$^{12}$ each is independently selected from the group of hydrogen, C$_1$–C$_4$ alkyl, C$_1$–C$_4$ heteroalkyl, and C$_1$–C$_4$ haloalkyl;
R$^{13}$ is hydrogen; or
R$^{13}$ and R$^{14}$ taken together form a bond;
R$^{14}$ through R$^{20}$ each independently is selected from the group of hydrogen, F, Cl, Br, OR$^{11}$, C$_1$–C$_4$ alkyl, C$_1$–C$_4$ haloalkyl, and C$_1$–C$_4$ heteroalkyl; or
R$^{14}$ and R$^{15}$ taken together are selected from the group of methylidene, carbonyl and thiocarbonyl; or
R$^{16}$ and R$^{17}$ taken together are selected from the group of methylidene, mono-substituted methylidene, di-substituted methylidene, carbonyl and thiocarbonyl; or
R$^{14}$ and R$^{16}$ taken together form a bond or "—O—" bridge; or
R$^{16}$ and R$^{18}$ taken together form a bond when n is 1; or
R$^{16}$ and R$^{19}$ taken together form a bond when n is 0;
R$^{21}$ is hydrogen;
n is 0, 1, 2, or 3;
or a pharmaceutically acceptable salt thereof.

4. A pharmaceutical composition, comprising a pharmaceutically acceptable carrier and a compound of any one of claims 1–3.

5. A compound according to any one of claims 1, 2 or 3, wherein R$^1$ is selected from the group of hydrogen, C$_1$–C$_4$ alkyl, COR$^{11}$, SO$_2$R$^{11}$, and CONR$^{11}$R$^{12}$.

6. A compound according to any one of claims 1, 2 or 3, wherein R$^2$ and R$^3$ each independently is selected from the group of C$_1$–C$_4$ alkyl, and C$_1$–C$_4$ haloalkyl.

7. A compound according to any one of claims 1, 2 or 3, wherein:
R$^5$ and R$^7$ taken together form a bond;
R$^4$ and R$^6$ each independently is selected from the group of hydrogen, F, Cl, Br, CN, OR$^{11}$, C$_1$–C$_4$ alkyl, and C$_1$–C$_4$ haloalkyl.

8. A compound according to any one of claims 1, 2 or 3, wherein:
R$^6$ and R$^7$ taken together are selected from the group of methylidene, and carbonyl;
R$^4$ and R$^5$ each independently is selected from the group of hydrogen, F, and C$_1$–C$_4$ alkyl.

9. A compound according to any one of claims 1, 2 or 3, wherein R$^8$ through R$^{10}$ each independently is selected from the group of hydrogen, F, Cl, Br, NO$_2$, CN, OR$^{11}$, SR$^{11}$, C$_1$–C$_6$ alkyl, C$_1$–C$_6$ heteroalkyl, and C$_1$–C$_6$ haloalkyl.

10. A compound according to claim 9, wherein R$^8$ through R$^{10}$ each independently is selected from the group of hydrogen, F, and OR$^{11}$.

11. A compound according to any one of claims 1, 2 or 3, wherein R$^{11}$ through R$^{12}$ each independently is selected from the group of hydrogen, and C$_1$–C$_4$ alkyl.

12. A compound of the formula:

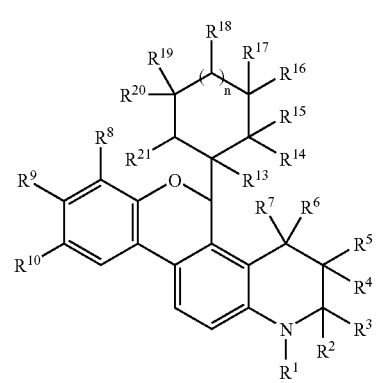

wherein:
R$^1$ is selected from the group of hydrogen, C$_1$–C$_4$ alkyl, C$_1$–C$_4$ haloalkyl, C$_1$–C$_4$ heteroalkyl, COR$^{11}$, CO$_2$R$^{11}$, SO$_2$R$^{11}$, and CONR$^{11}$R$^{12}$;
R$^2$ and R$^3$ each independently is selected from the group of hydrogen, C$_1$–C$_6$ alkyl, and C$_1$–C$_6$ haloalkyl; or
R$^2$ and R$^3$ taken together form a cycloalkyl ring of from three to twelve carbons;
R$^4$ through R$^7$ each independently is selected from the group of hydrogen, F, Cl, Br, CN, OR$^{11}$, C$_1$–C$_4$ alkyl, C$_1$–C$_4$ haloalkyl, and C$_1$–C$_4$ heteroalkyl; or
R$^5$ and R$^7$ taken together form a bond; or
R$^6$ and R$^7$ taken together are selected from the group of methylidene, mono-substituted methylidene, di-substituted methylidene and carbonyl;
R$^8$ through R$^{10}$ each independently is selected from the group of hydrogen, F, Cl, Br, I, NO$_2$, CN, OR$^{11}$, NR$^{11}$R$^{12}$, SR$^{11}$, COR$^{11}$, CO$_2$R$^{11}$, CONR$^{11}$R$^{12}$, C$_1$–C$_8$ alkyl, C$_1$–C$_8$ heteroalkyl, C$_1$–C$_8$ haloalkyl, allyl, C$_2$–C$_8$ alkenyl and C$_2$–C$_8$ alkynyl;
R$^{11}$ and R$^{12}$ each is independently selected from the group of hydrogen, C$_1$–C$_4$ alkyl, C$_1$–C$_4$ heteroalkyl, and C$_1$–C$_4$ haloalkyl;

41

$R^{13}$ is hydrogen;

$R^{14}$ and $R^{16}$ taken together form a bond or "—O—" bridge;

$R^{15}$, $R^{17}$, $R^{18}$, $R^{19}$, $R^{20}$ each independently is selected from the group of hydrogen, F, Cl, $C_1$–$C_4$ alkyl, and $C_1$–$C_4$ haloalkyl.

$R^{21}$ is hydrogen; and n is 0, 1, 2, or 3;

or a pharmaceutically acceptable salt thereof.

13. A compound of the formula:

(I)

wherein:

$R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;

$R^2$ and $R^3$ each independently is selected from the group of hydrogen, $C_1$–$C_6$ alkyl, and $C_1$–$C_6$ haloalkyl; or $R^2$ and $R^3$ taken together form a cycloalkyl ring of from three to twelve carbons;

$R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or $R^5$ and $R^7$ taken together form a bond; or $R^6$ and $R^7$ taken together are selected from the group of methylidene, mono-substituted methylidene, di-substituted methylidene and carbonyl;

$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;

$R^{13}$ is hydrogen;

$R^{14}$, $R^{15}$, $R^{18}$, $R^{19}$, $R^{20}$ each independently is selected from the group of hydrogen, F, Cl, $C_1$–$C_4$ alkyl, and $C_1$–$C_4$ haloalkyl.

$R^{16}$ and $R^{17}$ taken together are selected from the group of methylidene, mono-substituted methylidene, and di-substituted methylidene;

$R^{21}$ is hydrogen; or $R^{21}$ and $R^{20}$ taken together form a bond;

n is 0, 1, 2, or 3;

or a pharmaceutically acceptable salt thereof.

14. A compound of the formula:

(I)

wherein:

$R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;

$R^2$ and $R^3$ each independently is selected from the group of hydrogen, $C_1$–$C_6$ alkyl, and $C_1$–$C_6$ haloalkyl; or $R^2$ and $R^3$ taken together form a cycloalkyl ring of from three to twelve carbons;

$R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or $R^5$ and $R^7$ taken together form a bond; or $R^6$ and $R^7$ taken together are selected from the group of methylidene, mono-substituted methylidene, di-substituted methylidene and carbonyl;

$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;

$R^{13}$ is hydrogen;

$R^{14}$, $R^{15}$, $R^{17}$, $R^{20}$ each independently is selected from the group of hydrogen, F, Cl, $C_1$–$C_4$ alkyl, and $C_1$–$C_4$ haloalkyl $R^{16}$ and $R^{18}$ taken together form a bond when n is 1;

$R^{16}$ and $R^{19}$ taken together form a bond when n is 0;

$R^{21}$ is hydrogen; and n is 0, 1, 2, or 3;

or a pharmaceutically acceptable salt thereof.

15. A compound selected from the group of:

(±)-(5l, 1'l)-5-(3-methyl-2-cyclohexenyl)-9-fluoro-1,2-dihydro-2,2,4-trimethyl-5H-chromeno[3,4-f]quinoline (compound 24);

(±)-(5l, 1'u)-5-(3-methyl-2-cyclohexenyl)-9-fluoro-1,2-dihydro-2,2,4-trimethyl-5H-chromeno[3,4-f]quinoline (compound 25);

(+)-(5l,1'l)-5-(3-methyl-2-cyclohexenyl)-9-fluoro-1,2-dihydro-2,2,4-trimethyl-5H-chromeno[3,4-f]quinoline (compound 27);

(−)-(5l,1'l)-5-(3-methyl-2-cyclohexenyl)-9-fluoro-1,2-dihydro-2,2,4-trimethyl-5H-chromeno[3,4-f]quinoline (compound 28);

(±)-(5l,1'l)-5-(3-methyl-2-cyclohexenyl)-9-hydroxy-1,2-dihydro-2,2,4-trimethyl-5H-chromeno[3,4-f]quinoline (compound 29);

(±)-(5l,1'u)-5-(3-methyl-2-cyclohexenyl)-9-hydroxy-1,2-dihydro-2,2,4-trimethyl-5H-chromeno[3,4-f]quinoline (compound 30);

(+)-(5l,1'l)-5-(3-methyl-2-cyclohexenyl)-9-hydroxy-1,2-dihydro-2,2,4-trimethyl-5H-chromeno[3,4-f]quinoline (compound 32);

(−)-(5l,1'l)-5-(3-methyl-2-cyclohexenyl)-9-hydroxy-1,2-dihydro-2,2,4-trimethyl-5H-chromeno[3,4-f]quinoline (compound 33);

(±)-(5l,1'l)-5-(3-methyl-2-cyclohexenyl)-7,9-difluoro-1,2-dihydro-2,2,4-trimethyl-5H-chromeno[3,4-f]quinoline (compound 34);

(±)-(5l,1'u)-5-(3-methyl-2-cyclohexenyl)-7,9-difluoro-1,2-dihydro-2,2,4-trimethyl-5H-chromeno[3,4-f]quinoline (compound 35);

(+)-(5l,1'l)-5-(3-methyl-2-cyclohexenyl)-7,9-difluoro-1,2-dihydro-2,2,4-trimethyl-5H-chromeno[3,4-f]quinoline (compound 37);

(−)-(5l,1'l)-5-(3-methyl-2-cyclohexenyl)-7,9-difluoro-1,2-dihydro-2,2,4-trimethyl-5H-chromeno[3,4-f]quinoline (compound 38);

(±)-(5l,1'l)-5-(3-methyl-2-cyclohexenyl)-9-methoxy-1,2-dihydro-2,2,4-trimethyl-5H-chromeno[3,4-f]quinoline (compound 39);

(±)-(5l,1'l)-5-(3-methyl-2-cyclohexenyl)-9-fluoro-1,2-dihydro-2,2-dimethyl-5H-chromeno[3,4-f]quinoline (compound 41);

(±)-(5l,1'u)-5-(3-methyl-2-cyclohexenyl)-9-fluoro-1,2-dihydro-2,2-dimethyl-5H-chromeno[3,4-f]quinoline (compound 42);

(±)-(5l,1'l)-5-(3-methyl-2-cyclopentenyl)-9-fluoro-1,2-dihydro-2,2,4-trimethyl-5H-chromeno[3,4-f]quinoline (compound 44);

(±)-(5l,1'u)-5-(3-methyl-2-cyclopentenyl)-9-fluoro-1,2-dihydro-2,2,4-trimethyl-5H-chromeno[3,4-f]quinoline (compound 45);

(±)-(5l,1'l)-5-(3,5,5-trimethyl-2-cyclohexenyl)-9-fluoro-1,2-dihydro-2,2,4-trimethyl-5H-chromeno[3,4-f]quinoline (compound 47);

(±)-(5l,1'u)-5-(3,5,5-trimethyl-2-cyclohexenyl)-9-fluoro-1,2-dihydro-2,2,4-trimethyl-5H-chromeno[3,4-f]quinoline (compound 48);

(±)-(5l,1'l)-5-(3-methyl-2-cyclopentenyl)-7,9-difluoro-1,2-dihydro-2,2,4-trimethyl-5H-chromeno[3,4-f]quinoline (compound 50);

(±)-(5l,1'u)-5-(3-methyl-2-cyclopentenyl)-7,9-difluoro-1,2-dihydro-2,2,4-trimethyl-5H-chromeno[3,4-f]quinoline (compound 51);

(±)-5-(3-methyl-3-cyclopentenyl)-7,9-difluoro-1,2-dihydro-2,2,4-trimethyl-5H-chromeno[3,4-f]quinoline (compound 52);

(±)-5-(2-cyclopenta-1,3-dienyl)-9-fluoro-1,2-dihydro-2,2,4-trimethyl-5H-chromeno[3,4-f]quinoline (compound 53);

(±)-(5ll')-5-(3-ethyl-2-cyclohexenyl)-9-fluoro-1,2-dihydro-2,2,4-trimethyl-5H-chromeno[3,4-f]quinoline (compound 55);

(±)-(5l,1'u)-5-(3-ethyl-2-cyclohexenyl)-9-fluoro-1,2-dihydro-2,2,4-trimethyl-5H-chromeno[3,4-f]quinoline (compound 56);

(±)-(5l,1'l)-5-(3-methyl-2-cyclohexenyl)-7-fluoro-1,2-dihydro-2,2,4-trimethyl-5H-chromeno[3,4-f]quinoline (compound 58);

(±)-(5l,1'u)-5-(3-methyl-2-cyclohexenyl)-7-fluoro-1,2-dihydro-2,2,4-trimethyl-5H-chromeno[3,4-f]quinoline (compound 59);

(±)-(5l,1'l)-5-(3-ethyl-2-cyclohexenyl)-7,9-difluoro-1,2-dihydro-2,2,4-trimethyl-5H-chromeno[3,4-f]quinoline (compound 61);

(±)-(5l,1'l)-5-(3-ethylidenecyclohexyl)-7,9-difluoro-1,2-dihydro-2,2,4-trimethyl-5H-chromeno[3,4-f]quinoline (compound 62);

(±)-(5l,1'l)-5-(3-methyl-3-cyclohexenyl)-7,9-difluoro-1,2-dihydro-2,2,4-trimethyl-5H-chromeno[3,4-f]quinoline (compound 63);

(±)-(5l,1'l)-5-(3-methyl-2-cyclohexenyl)-9-fluoro-1,2-dihydro-8-methoxy-2,2,4-trimethyl-5H-chromeno[3,4-f]quinoline (compound 64);

(±)-(5l,1'u)-5-(3-methyl-2-cyclohexenyl)-9-fluoro-1,2-dihydro-8-methoxy-2,2,4-trimethyl-5H-chromeno[3,4-f]quinoline (compound 65);

(±)-(5l,1'l)-5-(2-cyclopentenyl)-7,9-difluoro-1,2-dihydro-2,2,4-trimethyl-5H-chromeno[3,4-f]quinoline (compound 67);

(±)-(5l,1'u)-5-(2-cyclopentenyl)-7,9-difluoro-1,2-dihydro-2,2,4-trimethyl-5H-chromeno[3,4-f]quinoline (compound 68);

(±)-5-(1-cyclopentenyl)-7,9-difluoro-1,2-dihydro-2,2,4-trimethyl-5H-chromeno[3,4-f]quinoline (compound 69);

(±)-(5l,1'l)-5-(2,3-dimethyl-2-cyclopentenyl)-7,9-difluoro-1,2-dihydro-2,2,4-trimethyl-5H-chromeno[3,4-f]quinoline (compound 71);

(+)-(5l,1'l)-5-(2,3-dimethyl-2-cyclopentenyl)-7,9-difluoro-1,2-dihydro-2,2,4-trimethyl-5H-chromeno[3,4-f]quinoline (compound 73);

(−)-(5l,1'l)-5-(2,3-dimethyl-2-cyclopentenyl)-7,9-difluoro-1,2-dihydro-2,2,4-trimethyl-5H-chromeno[3,4-f]quinoline (compound 74);

(±)-(5l,1'l)-5-(2-cyclohexenyl)-7,9-difluoro-1,2-dihydro-2,2,4-trimethyl-5H-chromeno[3,4-f]quinoline (compound 75);

(±)-(5l,1'u)-5-(2-cyclohexenyl)-7,9-difluoro-1,2-dihydro-2,2,4-trimethyl-5H-chromeno[3,4-f]quinoline (compound 76);

(±)-(5l,1'l)-5-(2-cyclohexenyl)-7,9-difluoro-1,2,3,4-tetrahydro-2,2-dimethyl-4-methylidene-5H-chromeno[3,4-f]quinoline (compound 77);

(±)-(5l,1'l)-5-(2-methylidenecyclohexyl)-9-fluoro-1,2-dihydro-2,2,4-trimethyl-5H-chromeno[3,4-f]quinoline (compound 79);

(±)-(5l,1'u)-5-(2-methylidenecyclohexyl)-9-fluoro-1,2-dihydro-2,2,4-trimethyl-5H-chromeno[3,4-f]quinoline (compound 80);

(±)-(5l,1'l)-5-(2-oxocyclohexyl)-9-fluoro-1,2-dihydro-2,2,4-trimethyl-5H-chromeno[3,4-f]quinoline (compound 81);

(±)-(5l,1'u)-5-(2-oxocyclohexyl)-9-fluoro-1,2-dihydro-2,2,4-trimethyl-5H-chromeno[3,4-f]quinoline (compound 82);

(±)-(5l,1'l)-5-(3-methyl-2-cyclohexenyl)-9-methoxy-1,2-dihydro-1,2,2,4-tetramethyl-5H-chromeno[3,4-f]quinoline (compound 83);

(±)-5-(2-cyclohexenyl)-9-fluoro-1,2-dihydro-2,2,4-trimethyl-5H-chromeno[3,4-f]-quinoline (compound 84);

(±)-(5l,1'l)-5-(2,3-dimethyl-2-cyclohexenyl)-7,9-difluoro-1,2-dihydro-2,2,4-trimethyl-5H-chromeno[3,4-f]quinoline (compound 85);

(±)-5-(3-methylidene-cyclohexyl)-7,9-difluoro-1,2-dihydro-2,2,4-trimethyl-5H-chromeno[3,4-f]quinoline (compound 87);

(±)-(5l,1'u)-5-(3-ethylidenecyclohexyl)-7,9-difluoro-1,2-dihydro-2,2,4-trimethyl-5H-chromeno[3,4-f]quinoline (compound 88);

(±)-(5l,1'l)-5-(2-cycloheptenyl)-7,9-difluoro-1,2-dihydro-2,2,4-trimethyl-5H-chromeno[3,4-f]quinoline (Compound 89);

(±)-(5l,1'l)-5-(2-cyclooctenyl)-7,9-difluoro-1,2-dihydro-2,2,4-trimethyl-5H-chromeno[3,4-f]quinoline (Compound 91);

(±)-(5l,1'u)-5-(2-cyclooctenyl)-7,9-difluoro-1,2-dihydro-2,2,4-trimethyl-5H-chromeno[3,4-f]quinoline (Compound 92);

(±)-(5l,1'l)-5-(2,3-epoxy-3-methylcyclohexyl)-7,9-difluoro-1,2-dihydro-2,2,4-trimethyl-5H-chromeno[3,4-f]quinoline (Compound 94);

(±)-(5l,1'l)-5-(3-methyl-2-cyclohexenyl)-7,9-difluoro-1,2,3,4-tetrahydro-2,2-dimethyl-4-methylene-5H-chromeno[3,4-f]quinolin-3-ol (Compound 95);

(±)-(5l,1'l)-5-(2,3-epoxy-2,3-dimethylcyclopentyl)-7,9-difluoro-1,2-dihydro-2,2,4-trimethyl-5H-chromeno[3,4-f]quinoline (Compound 96);

(±)-(5l,1'u)-5-(2,3-epoxy-3-methylcyclohexyl)-7,9-difluoro-1,2-dihydro-2,2,4-trimethyl-5H-chromeno[3,4-f]quinoline (Compound 97); and (±)-(5l,1'l)-5-(3-methyl-2-cyclohexenyl)-7,9-difluoro-1,2,3,4-tetrahydro-2,2-dimethyl-5H-chromeno[3,4-f]quinolin-4-one (Compound 98).

16. A compound selected from the group of:

(±)-(5l,1'l)-5-(3-methyl-2-cyclohexenyl)-9-fluoro-1,2-dihydro-2,2,4-trimethyl-5H-chromeno[3,4-f]quinoline (compound 24);

(−)-(5l,1'l)-5-(3-methyl-2-cyclohexenyl)-9-fluoro-1,2-dihydro-2,2,4-trimethyl-5H-chromeno[3,4-f]quinoline (compound 28);

(−)-(5l,1'l)-5-(3-methyl-2-cyclohexenyl)-9-hydroxy-1,2-dihydro-2,2,4-trimethyl-5H-chromeno[3,4-f]quinoline (compound 33);

(±)-(5l,1'l)-5-(3-methyl-2-cyclohexenyl)-7,9-difluoro-1,2-dihydro-2,2,4-trimethyl-5H-chromeno[3,4-f]quinoline (compound 34);

(±)-(5l,1'u)-5-(3-methyl-2-cyclohexenyl)-7,9-difluoro-1,2-dihydro-2,2,4-trimethyl-5H-chromeno[3,4-f]quinoline (compound 35);

(−)-(5l,1'l)-5-(3-methyl-2-cyclohexenyl)-7,9-difluoro-1,2-dihydro-2,2,4-trimethyl-5H-chromeno[3,4-f]quinoline (compound 38);

(±)-(5l,1'l)-5-(3-methyl-2-cyclopentenyl)-7,9-difluoro-1,2-dihydro-2,2,4-trimethyl-5H-chromeno[3,4-f]quinoline (compound 50);

(±)-(5l,1'u)-5-(3-methyl-2-cyclopentenyl)-7,9-difluoro-1,2-dihydro-2,2,4-trimethyl-5H-chromeno[3,4-f]quinoline (compound 51);

(±)-(5l,1'l)-5-(2,3-dimethyl-2-cyclopentenyl)-7,9-difluoro-1,2-dihydro-2,2,4-trimethyl-5H-chromeno[3,4-f]quinoline (compound 71);

(−)-(5l,1'l)-5-(2,3-dimethyl-2-cyclopentenyl)-7,9-difluoro-1,2-dihydro-2,2,4-trimethyl-5H-chromeno[3,4-f]quinoline (compound 74); and (±)-(5l,1'l)-5-(3-methyl-2-cyclohexenyl)-7,9-difluoro-1,2,3,4-tetrahydro-2,2-dimethyl-5H-chromeno[3,4-f]quinolin-4-one (Compound 98).

17. A compound of the formula:

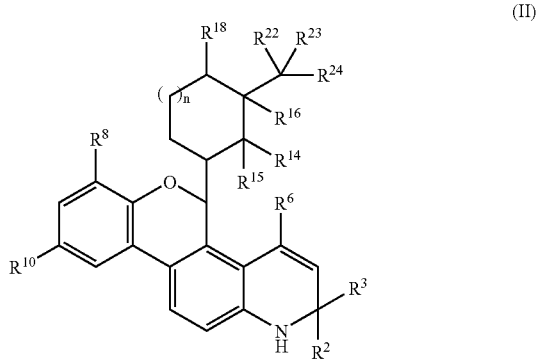

(II)

wherein:
$R^2$ and $R^3$ each independently is selected from the group of hydrogen, $C_1$–$C_4$ alkyl, and $C_1$–$C_4$ haloalkyl;

$R^6$ is selected from the group of hydrogen, F, Cl, Br, CN, $OR^{11}$, $C_1$–$C_4$ alkyl, and $C_1$–$C_4$ haloalkyl;

$R^8$ and $R^{10}$ each independently is selected from the group consisting of hydrogen, F, Cl, Br, CN, $OR^{11}$, $NR^{11}R^{12}$, $SR^{11}$, $COR^{11}$, $C_1$–$C_4$ alkyl, $C_1$–$C_4$ heteroalkyl, $C_1$–$C_4$ haloalkyl, allyl, and $C_2$–$C_4$ alkenyl;

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;

$R^{14}$, $R^{15}$, $R^{18}$, $R^{22}$, $R^{23}$, $R^{24}$ each independently is selected from the group of hydrogen, F, Cl, $OR^{11}$, $C_1$–$C_4$ alkyl, $C_1$–$C_4$ haloalkyl, and $C_1$–$C_4$ heteroalkyl;

$R^{22}$, $R^{23}$, $R^{24}$ together consists of not more than 3 carbon atoms;

$R^{16}$ taken together with one of $R^{14}$, $R^{18}$, and $R^{22}$ form a bond or "—O—" bridge;

n is 0, 1, 2, or 3;

or a pharmaceutically acceptable salt thereof.

18. A compound of the formula:

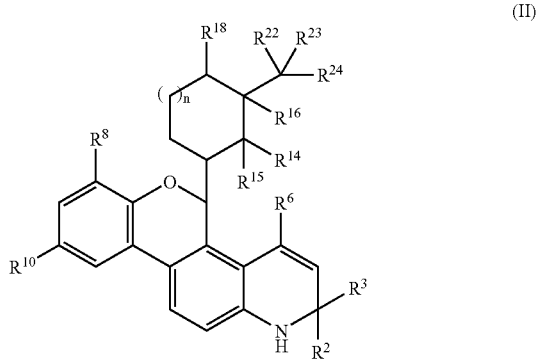

(II)

wherein:
$R^2$ and $R^3$ each independently is selected from the group of $C_1$–$C_4$ alkyl;

$R^6$ is selected from the group of F, Cl, Br, $C_1$–$C_4$ alkyl, and $C_1$–$C_4$ haloalkyl;

$R^8$ and $R^{10}$ each independently is selected from the group of hydrogen, F, Cl, Br, CN, $OR^{11}$, $C_1$–$C_4$ alkyl, and $C_1$–$C_4$ haloalkyl;

$R^{11}$ and $R^{12}$ each is independently selected from the group of hydrogen, $C_1$–$C_4$ alkyl;

$R^{14}$, $R^{15}$, $R^{18}$, $R^{22}$, $R^{23}$, $R^{24}$ each independently is selected from the group of hydrogen, F, $C_1$–$C_4$ alkyl;

$R^{16}$ taken together with one of $R^{14}$, $R^{18}$, and $R^{22}$ form a bond or "—O—" bridge;

$R^{22}$, $R^{23}$, $R^{24}$ together consists of not more than 3 carbon atoms; and n is 0, 1, or 2;

or a pharmaceutically acceptable salt thereof.

19. A compound according to claim 18, wherein $R^2$ and $R^3$ each independently is $CH_3$;

$R^6$ is selected from the group of F, Cl, Br, $CH_3$, $CH_2CH_3$, and $CF_3$;

$R^8$ is hydrogen or F;

$R^{10}$ is selected from the group of hydrogen, F, Cl, Br, CN, OH, $OCH_3$, $CH_3$, $CH_2CH_3$, and $CF_3$;

$R^{14}$ and $R^{16}$ taken together form a bond or "—O—" bridge;

$R^{15}$, $R^{18}$, $R^{22}$, $R^{23}$, and $R^{24}$ each independently is hydrogen or $CH_3$.

20. A pharmaceutical composition according to claim 4, wherein $R^1$ is selected from the group of hydrogen, $C_1$–$C_4$ alkyl, $COR^{11}$, $SO_2R^{11}$, and $CONR^{11}R^{12}$.

21. A pharmaceutical composition according to claim 4, wherein $R^2$ and $R^3$ each independently is selected from the group of $C_1$–$C_4$ alkyl, and $C_1$–$C_4$ haloalkyl.

22. A pharmaceutical composition according to claim 4, wherein $R^5$ and $R^7$ taken together form a bond;

$R^4$ and $R^6$ each independently is selected from the group of hydrogen, F, Cl, Br, CN, $OR^{11}$, $C_1$–$C_4$ alkyl, and $C_1$–$C_4$ haloalkyl.

23. A pharmaceutical composition according to claim 4, wherein $R^6$ and $R^7$ taken together are selected from the group of methylidene, and carbonyl;

$R^4$ and $R^5$ each independently is selected from the group of hydrogen, F, and $C_1$–$C_4$ alkyl.

24. A pharmaceutical composition according to claim 4, wherein $R^8$ through $R^{10}$ each independently is selected from the group of hydrogen, F, Cl, Br, $NO_2$, CN, $OR^{11}$, $SR^{11}$, $C_1$–$C_6$ alkyl, $C_1$–$C_6$ heteroalkyl, and $C_1$–$C_6$ haloalkyl.

25. A pharmaceutical composition according to claim 24, wherein $R^8$ through $R^{10}$ each independently is selected from the group of hydrogen, F, and $OR^{11}$.

26. A pharmaceutical composition according to claim 4, wherein $R^{11}$ through $R^{12}$ each independently is selected from the group of hydrogen, and $C_1$–$C_4$ alkyl.

27. A pharmaceutical composition, comprising a pharmaceutically acceptable carrier and a compound of formula:

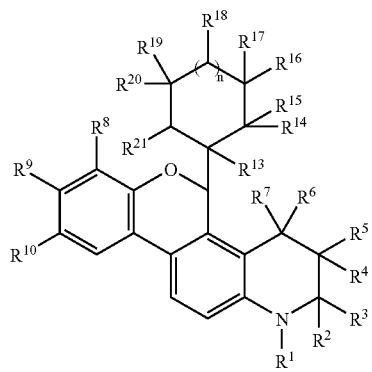

(I)

wherein:

$R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;

$R^2$ and $R^3$ each independently is selected from the group of hydrogen, $C_1$–$C_6$ alkyl, and $C_1$–$C_6$ haloalkyl; or $R^2$ and $R^3$ taken together form a cycloalkyl ring of from three to twelve carbons;

$R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or $R^5$ and $R^7$ taken together form a bond; or $R^6$ and $R^7$ taken together are selected from the group of methylidene, mono-substituted methylidene, di-substituted methylidene and carbonyl;

$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;

$R^{13}$ is hydrogen;

$R^{14}$ and $R^{16}$ taken together form a bond or "—O—" bridge;

$R^{15}$, $R^{17}$, $R^{18}$, $R^{19}$, $R^{20}$ each independently is selected from the group of hydrogen, F, Cl, $C_1$–$C_4$ alkyl, and $C_1$–$C_4$ haloalkyl;

$R^{21}$ is hydrogen; or $R^{21}$ and $R^{20}$ taken together form a bond; and n is 0, 1, 2, or 3;

or a pharmaceutically acceptable salt thereof.

28. A pharmaceutical composition, comprising a pharmaceutically acceptable carrier and a compound of formula:

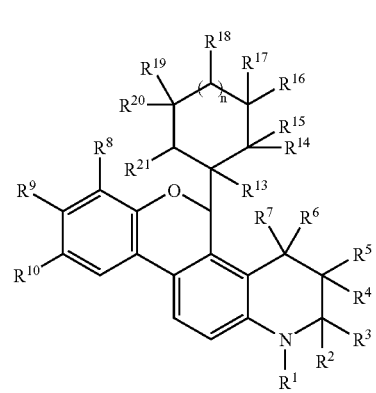

(I)

wherein:

$R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;

$R^2$ and $R^3$ each independently is selected from the group of hydrogen, $C_1$–$C_6$ alkyl, and $C_1$–$C_6$ haloalkyl; or $R^2$ and $R^3$ taken together form a cycloalkyl ring of from three to twelve carbons;

$R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or $R^5$ and $R^7$ taken together form a bond; or $R^6$ and $R^7$ taken together are selected from the group of methylidene, mono-substituted methylidene, di-substituted methylidene and carbonyl;

R[8] through R[10] each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;

R[11] and R[12] each is independently selected from the group of hydrogen, $C_1$–$C_4$ alkyl, $C_1$–$C_4$ heteroalkyl, and $C_1$–$C_4$ haloalkyl;

R[13] is hydrogen;

R[14], R[15], R[18], R[19], R[20] each independently is selected from the group of hydrogen, F, Cl, $C_1$–$C_4$ alkyl, and $C_1$–$C_4$ haloalkyl;

R[16] and R[17] taken together are selected from the group of methylidene, mono-substituted methylidene, and di-substituted methylidene;

R[21] is hydrogen; or

R[21] and R[20] taken together form a bond; and n is 0, 1, 2, or 3;

or a pharmaceutically acceptable salt thereof.

29. A pharmaceutical composition, comprising a pharmaceutically acceptable carrier and a compound of formula:

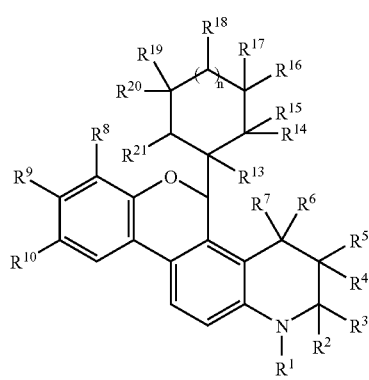

(I)

wherein:

R[1] is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;

R[2] and R[3] each independently is selected from the group of hydrogen, $C_1$–$C_6$ alkyl, and $C_1$–$C_6$ haloalkyl; or R[2] and R[3] taken together form a cycloalkyl ring of from three to twelve carbons;

R[4] through R[7] each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or R[5] and R[7] taken together form a bond; or R[6] and R[7] taken together are selected from the group of methylidene, mono-substituted methylidene, di-substituted methylidene and carbonyl;

R[8] through R[10] each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;

R[11] and R[12] each is independently selected from the group of hydrogen, $C_1$–$C_4$ alkyl, $C_1$–$C_4$ heteroalkyl, and $C_1$–$C_4$ haloalkyl;

R[13] is hydrogen;

R[14], R[15], R[17], R[20] each independently is selected from the group of hydrogen, F, Cl, $C_1$–$C_4$ alkyl, and $C_1$–$C_4$ haloalkyl;

R[16] and R[18] taken together form a bond when n is 1; or

R[16] and R[19] taken together form a bond when n is 0;

R[21] is hydrogen; and n is 0, 1, 2, or 3;

or a pharmaceutically acceptable salt thereof.

* * * * *

UNITED STATES PATENT AND TRADEMARK OFFICE
CERTIFICATE OF CORRECTION

PATENT NO.       : 7,071,205 B2
APPLICATION NO. : 10/684229
DATED            : July 4, 2006
INVENTOR(S)      : Lin Zhi et al.

It is certified that error appears in the above-identified patent and that said Letters Patent is hereby corrected as shown below:

IN THE TITLE PAGES:

In Item [56] References Cited, in U.S. PATENT DOCUMENTS:
please add the following reference: --6,001,846 A   12/1999   Edwards et al.   514/285--
in 6,566,358 please replace "Zhi et al." with --Zhang et al.--
in 6,566,372 please replace "West et al." with --Zhi et al.--

In Item [56] References Cited, in OTHER PUBLICATIONS:
in Hamann et al., please replace "dihyrdo" with --dihydro--

At column 8, Table A, row $R^1$, please replace "$C_1$-C haloalkyl" with --$C_1$-$C_4$ haloalkyl--
at column 9, Table A, row $R^9$, please replace "$CONR^H R^{12}$" with --$CONR^{11}R^{12}$--
at column 11, Table A, below row $R^{16}$, please replace "$R^{15}$" with --$R^{16}$--

Please replace Claims 12, 13, 14, and 15 with the following Claims:

Col. 40
12. A compound of the formula:

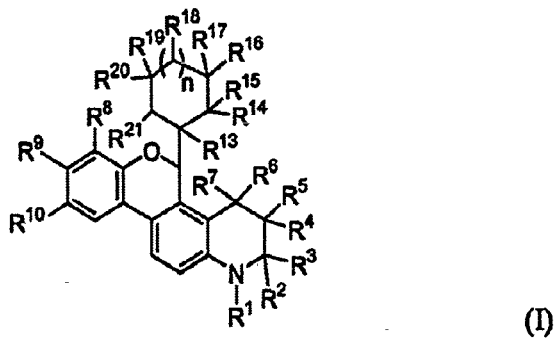

(I)

wherein:
  $R^1$ is selected from the group of hydrogen, $C_1$–$C_4$ alkyl, $C_1$–$C_4$ haloalkyl, $C_1$–$C_4$ heteroalkyl, $CO_2R^{11}$, $CO_2R^{11}$, $SO_2R^{11}$, and $CONR^{11}R^{12}$;
  $R^2$ and $R^3$ each independently is selected from the group of hydrogen, $C_1$–$C_6$ alkyl, and $C_1$–$C_6$ haloalkyl; or
  $R^2$ and $R^3$ taken together form a cycloalkyl ring of from three to twelve carbons;
  $R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or
  $R^5$ and $R^7$ taken together form a bond; or
  $R^6$ and $R^7$ taken together are selected from the group of methylidene, mono-substituted methylidene, di-substituted methylidene and carbonyl;

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;

$R^{13}$ is hydrogen;

$R^{14}$ and $R^{16}$ taken together form a bond or "–O–" bridge;

$R^{15}$, $R^{17}$, $R^{18}$, $R^{19}$, $R^{20}$ each independently is selected from the group of hydrogen, F, Cl, $C_1$–$C_4$ alkyl, and $C_1$–$C_4$ haloalkyl;

$R^{21}$ is hydrogen; and n is 0, 1, 2, or 3;

or a pharmaceutically acceptable salt thereof.

Col. 41
13. A compound of the formula:

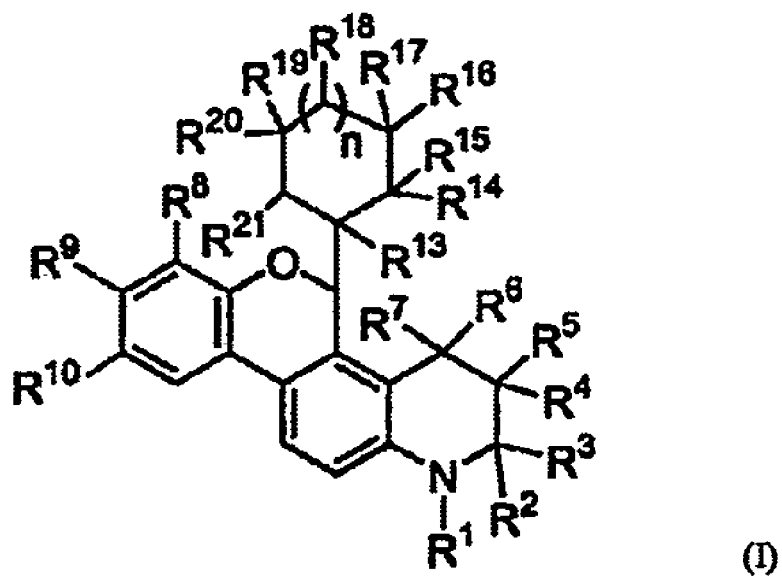

(I)

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

wherein:
$R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;
$R^2$ and $R^3$ each independently is selected from the group of hydrogen, $C_1$–$C_6$ alkyl, and $C_1$–$C_6$ haloalkyl; or
$R^2$ and $R^3$ taken together form a cycloalkyl ring of from three to twelve carbons;
$R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or
$R^5$ and $R^7$ taken together form a bond; or
$R^6$ and $R^7$ taken together are selected from the group of methylidene, mono-substituted methylidene, di-substituted methylidene and carbonyl;
$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;
$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;
$R^{13}$ is hydrogen;
$R^{14}$, $R^{15}$, $R^{18}$, $R^{19}$, $R^{20}$ each independently is selected from the group of hydrogen, F, Cl, $C_1$–$C_4$ alkyl, and $C_1$–$C_4$ haloalkyl;
$R^{16}$ and $R^{17}$ taken together are selected from the group of methylidene, mono-substituted methylidene, and di-substituted methylidene;
$R^{21}$ is hydrogen; or
$R^{21}$ and $R^{20}$ taken together form a bond;
n is 0, 1, 2, or 3;
or a pharmaceutically acceptable salt thereof.

UNITED STATES PATENT AND TRADEMARK OFFICE
CERTIFICATE OF CORRECTION

| | |
|---|---|
| PATENT NO. | : 7,071,205 B2 |
| APPLICATION NO. | : 10/684229 |
| DATED | : July 4, 2006 |
| INVENTOR(S) | : Lin Zhi et al. |

It is certified that error appears in the above-identified patent and that said Letters Patent is hereby corrected as shown below:

Col. 42
14. A compound of the formula:

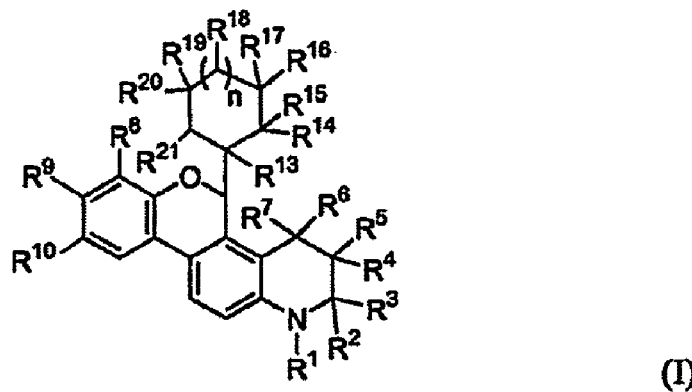

(I)

wherein:
  $R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;
  $R^2$ and $R^3$ each independently is selected from the group of hydrogen, $C_1$–$C_6$ alkyl, and $C_1$–$C_6$ haloalkyl; or
  $R^2$ and $R^3$ taken together form a cycloalkyl ring of from three to twelve carbons;
  $R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or
  $R^5$ and $R^7$ taken together form a bond; or
  $R^6$ and $R^7$ taken together are selected from the group of methylidene, mono-substituted methylidene, di-substituted methylidene and carbonyl;
  $R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;

UNITED STATES PATENT AND TRADEMARK OFFICE
CERTIFICATE OF CORRECTION

| | |
|---|---|
| PATENT NO. | : 7,071205 B2 |
| APPLICATION NO. | : 10/684229 |
| DATED | : July 4, 2006 |
| INVENTOR(S) | : Lin Zhi et al. |

It is certified that error appears in the above-identified patent and that said Letters Patent is hereby corrected as shown below:

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;
$R^{13}$ is hydrogen;
$R^{14}$, $R^{15}$, $R^{17}$, $R^{20}$ each independently is selected from the group of hydrogen, F, Cl, $C_1$–$C_4$ alkyl, and $C_1$–$C_4$ haloalkyl;
$R^{16}$ and $R^{18}$ taken together form a bond when n is 1;
$R^{16}$ and $R^{19}$ taken together form a bond when n is 0;
$R^{21}$ is hydrogen; and
n is 0, 1, 2, or 3;
or a pharmaceutically acceptable salt thereof.

Col. 42-45
15. A Compound selected from the group of:

(±)-(51,1'l)-5-(3-methyl-2-cyclohexenyl)-9-fluoro-1,2-dihydro-2,2,4-trimethyl-5H-chromeno[3,4-f]quinoline (compound 24);
(±)-(51,1'u)-5-(3-methyl-2-cyclohexenyl)-9-fluoro-1,2-dihydro-2,2,4-trimethyl-5H-chromeno[3,4-f]quinoline (compound 25);
(+)-(51,1'l)-5-(3-methyl-2-cyclohexenyl)-9-fluoro-1,2-dihydro-2,2,4-trimethyl-5H-chromeno[3,4-f]quinoline (compound 27);
(–)-(51,1'l)-5-(3-methyl-2-cyclohexenyl)-9-fluoro-1,2-dihydro-2,2,4-trimethyl-5H-chromeno[3,4-f]quinoline (compound 28);
(±)-(51,1'1)-5-(3-methyl-2-cyclohexenyl)-9-hydroxy-1,2-dihydro-2,2,4-trimethyl-5H-chromeno[3,4-f]quinoline (compound 29);

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

(±)-(51,1'u)-5-(3-methyl-2-cyclohexenyl)-9-hydroxy-1,2-dihydro-2,2,4-trimethyl-5H-chromeno[3,4-f]quinoline (compound 30);

(+)-(51,1'1)-5-(3-methyl-2-cyclohexenyl)-9-hydroxy-1,2-dihydro-2,2,4-trimethyl-5H-cbromeno[3,4-fjquinoline (compound 32);

(–)-(51,1'1)-5-(3-methyl-2-cyclohexenyl)-9-hydroxy-1,2-dihydro-2,2,4-trimethyl-5H-chromeno[3,4-fJquinoline (compound 33);

(±)-(51,1'1)-5-3-methyl-2-cyclohexenyl)-7,9-difluoro-1,2-dihydro-2,2,4-trimethyl-5H-chromeno[3,4-f]quinoline (compound 34);

(±)-(51,1'u)-5-(3-methyl-2-cyclohexenyl)-7,9-difluoro-1,2-dihydro-2,2,4-trimethyl-5H-chromeno[3,4-f]quinoline (compound 35);

(+)-(51,1'1)-5-(3-methyl-2-cyclohexenyl)-7,9-difluoro-1,2-dihydro-2,2,4-trimethyl-5H-chromeno[3,4-f]quinoline (compound 37);

(–)-(51,1'1)-5-(3-methyl-2-cyclohexenyl)-7,9-difluoro-1,2-dihydro-2,2,4-trimethyl-5H-chromeno[3,4-f]quinoline (compound 38);

(±)-(51,1'1)-5-(3-methyl-2-cyclohexenyl)-9-methoxy-1,2-dihydro-2,2,4-trimethyl-5H-chromeno[3,4-f]quinoline (compound 39);

(±)-(51,1'1)-5-(3-methyl-2-cyclohexenyl)-9-fluoro-1,2-dihydro-2,2-dimethyl-5H-chromeno[3,4-f]quinoline (compound 41);

(±)-(51,1'u)-5-(3-methyl-2-cyclohexenyl)-9-fluoro-1,2-dihydro-2,2-dimethyl-5H-chromeno[3,4-f]quinoline (compound 42);

(±)-(51,1'1)-5-(3-methyl-2-cyclopentenyl)-9-fluoro-1,2-dihydro-2,2,4-trimethyl-5H-chromeno[3,4-f]quinoline (compound 44);

(±)-(51,1'u)-5-(3-methyl-2-cyclopentenyl)-9-fluoro-1,2-dihydro-2,2,4-trimethy-5H-chromeno[3,4-f]quinoline (compound 45);

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

- (±)-(5l,1'1)-5-(3,5,5-trimethyl-2-cyclohexenyl)-9-fluoro-1,2-dihydro-2,2,4-trimethyl-5H-chromeno[3,4-f]quinoline (compound 47);
- (±)-(5l,1'u)-5-(3,5,5-trimethyl-2-cyclohexenyl)-9-fluoro-1,2-dihydro-2,2,4-trimethyl-5H-chromeno[3,4-f]quinoline (compound 48);
- (±)-(5l,1'1)-5-(3-methyl-2-cyclopentenyl)-7,9-difluoro-1,2-dihydro-2,2,4-trimethyl-5H-chromeno[3,4-f]quinoline (compound 50);
- (±)-(5l,1'u)-5-(3-methyl-2-cyclopentenyl)-7,9-difluoro-1,2-dihydro-2,2,4-trimethyl-5H-chromeno[3,4-f]quinoline (compound 51);
- (±)-5-(3-methyl-3-cyclopentenyl)-7,9-difluoro-1,2-dihydro-2,2,4-trimethyl-5H-chromeno[3,4-f]quinoline (compound 52);
- (±)-5-(2-cyclopenta-1,3-dienyl)-9-fluoro-1,2-dihydro-2,2,4-trimethyl-5H-chromeno[3,4-f]quinoline (compound 53);
- (±)-(5l,1'1)-5-(3-ethyl-2-cyclohexenyl)-9-fluoro-1,2-dihydro-2,2,4-trimethyl-5H-chromeno[3,4-f]quinoline (compound 55);
- (±)-(5l,1'u)-5-(3-ethyl-2-cyclohexenyl)-9-fluoro-1,2-dihydro-2,2,4-trimethyl-5H-chromeno[3,4-f]quinoline (compound 56);
- (±)-(5l,1'1)-5-(3-methyl-2-cyclohexenyl)-7-fluoro-1,2-dihydro-2,2,4-trimethyl-5H-chromeno[3,4-f]quinoline (compound 58);
- (±)-(5l,1'u)-5-(3-methyl-2-cyclohexenyl)-7-fluoro-1,2-dihydro-2,2,4-trimethyl-5H-chromeno[3,4-f]quinoline (compound 59);
- (±)-(5l,1'1)-5-(3-ethyl-2-cyclohexenyl)-7,9-difluoro-1,2-dihydro-2,2,4-trimethyl-5H-chromeno[3,4-f]quinoline (compound 61);
- (±)-(5l,1'1)-5-(3-ethylidenecyclohexyl)-7,9-difluoro-1,2-dihydro-2,2,4-trimethyl-5H-chromeno[3,4-f]quinoline (compound 62);

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

(±)-(5l,1'l)-5-(3-methyl-3-cyclohexenyl)-7,9-difluoro-1,2-dihydro-2,2,4-trimethyl-5H-chromeno[3,4-f]quinoline (compound 63);

(±)-(5l,1'l)-5-(3-methyl-2-cyclobexenyl)-9-fluoro-1,2-dihydro-8-methoxy-2,2,4-trimethyl-5H-chromeno[3,4-f]quinoline (compound 64);

(±)-(5l,1'u)-5-(3-methyl-2-cyclohexenyl)-9-fluoro-1,2-dihydro-8-methoxy-2,2,4-trimethyl-5H-chromeno[3,4-f]quinoline (compound 65);

(±)-(5l,1'1)-5-(2-cyclopentenyl)-7,9-difluoro-1,2-dihydro-2,2,4-trimethyl-5H-chromeno[3,4-f]quinoline (compound 67);

(±)-(5l,1'u)-5-(2-cyclopentenyl)-7,9-difluoro-1,2-dihydro-2,2,4-trimethyl-5H-chromeno[3,4-f]quinoline (compound 68);

(±)-5-(1-cyclopentenyl)-7,9-difluoro-1,2-dihydro-2,2,4-trimethy1-5H-chromeno[3,4-f]quinoline (compound 69);

(±)-(5l,1'1)-5-(2,3-dimethyl-2-cyclopentenyl)-7,9-difluoro-1,2-dihydro-2,2,4-trimethyl-5H-chromeno[3,4-f]quinoline (compound 71);

(+)-(5l,1'1)-5-(2,3-dimethyl-2-eyclopentenyl)-7,9-difluoro-1,2-dihydro-2,2,4-trimethyl-5H-chromeno[3,4-f]quinoline (compound 73);

(−)-(5l,1'1)-5-(2,3-dimethyl-2-cyclopentenyl)-7,9-difluoro-1,2-dihydro-2,2,4-trimethyl-5H-chromeno[3,4-f]quinoline (compound 74);

(±)-(5l,1'1)-5-(2-cyclohexenyl)-7,9-difluoro-1,2-dihydro-2,2,4-trimethyl-5H-chromeno[3,4-f]quinoline (compound 75);

(±)-(5l,1'u)-5-(2-cyclohexenyl)-7,9-difluoro-1,2-dihydro-2,2,4-trimethyl-5H-chromeno[3,4-f]quinoline (compound 76);

(±)-(5l,1'1)-5-(2-cyclohexenyl)-7,9-difluoro-1,2,3,4-tetrahydro-2,2-dimethyl-4-methylidene-5H-chromeno[3,4-f]quinoline (compound 77);

UNITED STATES PATENT AND TRADEMARK OFFICE
CERTIFICATE OF CORRECTION

PATENT NO.       : 7,071,205 B2
APPLICATION NO.  : 10/684229
DATED            : July 4, 2006
INVENTOR(S)      : Lin Zhi et al.

It is certified that error appears in the above-identified patent and that said Letters Patent is hereby corrected as shown below:

(±)-(51,1'l)-5-(2-methylidenecyclohexyl)-9-fluoro-1,2-dihydro-2,2,4-trimethyl-5H-chromeno[3,4-f]quinoline (compound 79);

(±)-(51,1'u)-5-(2-methylidenecyclohexyl)-9-fluoro-1,2-dihydro-2,2,4-trimethyl-5H-chromeno[3,4-f]quinoline (compound 80);

(±)-(51,1'1)-5-(2-oxocyclohexyl)-9-fluoro-1,2-dihydro-2,2,4-trimethyl-5H-chromeno[3,4-f]quinoline (compound 81);

(±)-(51,1'u)-5-(2-oxocyclohexyl)-9-fluoro-1,2-dihydro-2,2,4-trimethyl-5H-chromeno[3,4-f]quinoline (compound 82);

(±)-(51,1'1)-5-(3-methyl-2-cyclohexenyl)-9-methoxy-1,2-dihydro-1,2,2,4-tetramethyl-5H-chromeno[3,4-f]quinoline (compound 83);

(±)-5-(2-cyclohexenyl)-9-fluoro-1,2-dihydro-2,2,4-trimethyl-5H-chromeno[3,4-f]-quinoline (compound 84);

(±)-(51,1'l)-5-(2,3-dimethyl-2-cyclohexenyl)-7,9-difiuoro-1,2-dihydro-2,2,4-trimethyl-5H-chromeno[3,4-f]quinoline (compound 85);

(±)-5-(3-methylidene-cyclohexyl)-7,9-difluoro-1,2-dihydro-2,2,4-trimethyl-5H-chromeno[3,4-f]quinoline (compound 87);

(±)-(51,1'u)-5-(3-ethylidenecyclohexyl)-7,9-difluoro-1,2-dihydro-2,2,4-trimethyl-5H-chromeno[3,4-f]quinoline (compound 88);

(±)-(51,1'l)-5-(2-cyclohepteny1)-7,9-difluoro-1,2-dihydro-2,2,4-trimethy1-5H-chromeno[3,4-f]quinoline (Compound 89);

(±)-(51,1'1)-5-(2-cyclooctenyl)-7,9-difluoro-1,2-dihydro-2,2,4-trimethyl-5H-chromeno[3,4-f]quinoline (Compound 91);

(±)-(51,1'u)-5-(2-cyclooctenyl)-7,9-difluoro-1,2-dihydro-2,2,4-trimethyl-5H-chromeno[3,4-f]quinoline (Compound 92);

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

(±)-(51,1'1)-5-(2,3-epoxy-3-methylcyclohexyl)-7,9-difluoro-1,2-dihydro-2,2,4-trimethyl-5H-chromeno[3,4-f]quinoline (Compound 94);

(±)-(51,1'1)-5-(3-methyl-2-cyclohexenyl)-7,9-difluoro-1,2,3,4-tetrahydro-2,2-dimethyl-4-methylene-5H-chromeno[3,4-f]quinolin-3-ol (Compound 95);

(±)-(51,1'1)-5-(2,3-epoxy-2,3-dimethylcyclopentyl)-7,9-difluoro-1,2-dihydro-2,2,4-trimethyl-5H-chromeno[3,4-f]quinoline (Compound 96);

(±)-(51,1'u)-5-(2,3-epoxy-3-methylcyclohexyl)-7,9-difluoro-1,2-dihydro-2,2,4-trimethyl-5H-chromeno[3,4-f]quinoline (Compound 97); and (±)-(51,1'1)-5-(3-methyl-2-cyclohexenyl)-7,9-difluoro-1,2,3,4-tetrahydro-2,2-dimethyl-5H-chromeno[3,4-f]quinolin-4-one (Compound 98).

Signed and Sealed this

Twenty-eighth Day of November, 2006

JON W. DUDAS
*Director of the United States Patent and Trademark Office*

UNITED STATES PATENT AND TRADEMARK OFFICE
CERTIFICATE OF CORRECTION

PATENT NO.       : 7,071,205 B2
APPLICATION NO.  : 10/684229
DATED            : July 4, 2006
INVENTOR(S)      : Lin Zhi et al.

It is certified that error appears in the above-identified patent and that said Letters Patent is hereby corrected as shown below:

IN THE TITLE PAGES:

In Item [56] References Cited, in U.S. PATENT DOCUMENTS:
please add the following reference: --6,001,846 A   12/1999   Edwards et al.   514/285--
in 6,566,358 please replace "Zhi et al." with --Zhang et al.--
in 6,566,372 please replace "West et al." with --Zhi et al.--

In Item [56] References Cited, in OTHER PUBLICATIONS:
in Hamann et al., please replace "dihyrdo" with --dihydro--

At column 8, Table A, row $R^1$, please replace "$C_1$-C haloalkyl" with --$C_1$-$C_4$ haloalkyl--
at column 9, Table A, row $R^9$, please replace "$CONR^HR^{12}$" with --$CONR^{11}R^{12}$--
at column 11, Table A, below row $R^{16}$, please replace "$R^{15}$" with --$R^{16}$--

Please replace Claims 12, 13, 14, and 15 with the following Claims:

Col. 40
12. A compound of the formula:

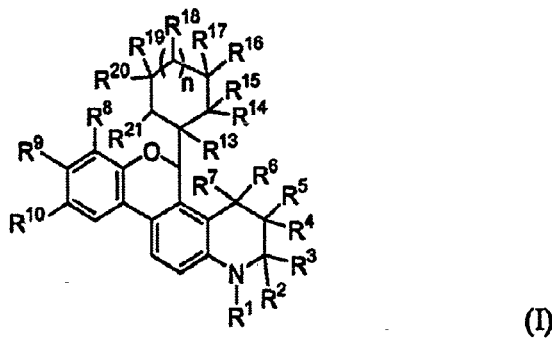

(I)

wherein:
  $R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;
  $R^2$ and $R^3$ each independently is selected from the group of hydrogen, $C_1$–$C_6$ alkyl, and $C_1$–$C_6$ haloalkyl; or
  $R^2$ and $R^3$ taken together form a cycloalkyl ring of from three to twelve carbons;
  $R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or
  $R^5$ and $R^7$ taken together form a bond; or
  $R^6$ and $R^7$ taken together are selected from the group of methylidene, mono-substituted methylidene, di-substituted methylidene and carbonyl;

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;

$R^{13}$ is hydrogen;

$R^{14}$ and $R^{16}$ taken together form a bond or "–O–" bridge;

$R^{15}$, $R^{17}$, $R^{18}$, $R^{19}$, $R^{20}$ each independently is selected from the group of hydrogen, F, Cl, $C_1$–$C_4$ alkyl, and $C_1$–$C_4$ haloalkyl;

$R^{21}$ is hydrogen; and n is 0, 1, 2, or 3;

or a pharmaceutically acceptable salt thereof.

Col. 41
13. A compound of the formula:

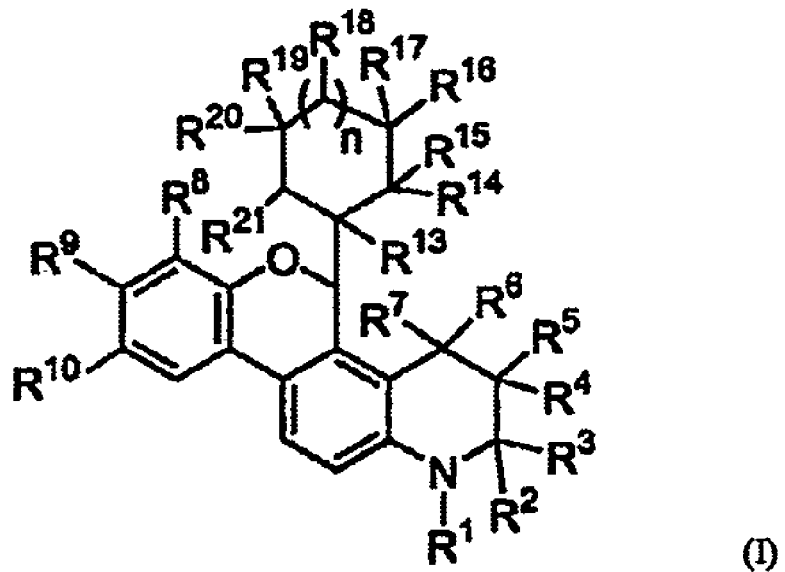

(I)

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

wherein:
$R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;
$R^2$ and $R^3$ each independently is selected from the group of hydrogen, $C_1$–$C_6$ alkyl, and $C_1$–$C_6$ haloalkyl; or
$R^2$ and $R^3$ taken together form a cycloalkyl ring of from three to twelve carbons;
$R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or
$R^5$ and $R^7$ taken together form a bond; or
$R^6$ and $R^7$ taken together are selected from the group of methylidene, mono-substituted methylidene, di-substituted methylidene and carbonyl;
$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;
$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;
$R^{13}$ is hydrogen;
$R^{14}$, $R^{15}$, $R^{18}$, $R^{19}$, $R^{20}$ each independently is selected from the group of hydrogen, F, Cl, $C_1$–$C_4$ alkyl, and $C_1$–$C_4$ haloalkyl;
$R^{16}$ and $R^{17}$ taken together are selected from the group of methylidene, mono-substituted methylidene, and di-substituted methylidene;
$R^{21}$ is hydrogen; or
$R^{21}$ and $R^{20}$ taken together form a bond;
n is 0, 1, 2, or 3;
or a pharmaceutically acceptable salt thereof.

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

Col. 42
14. A compound of the formula:

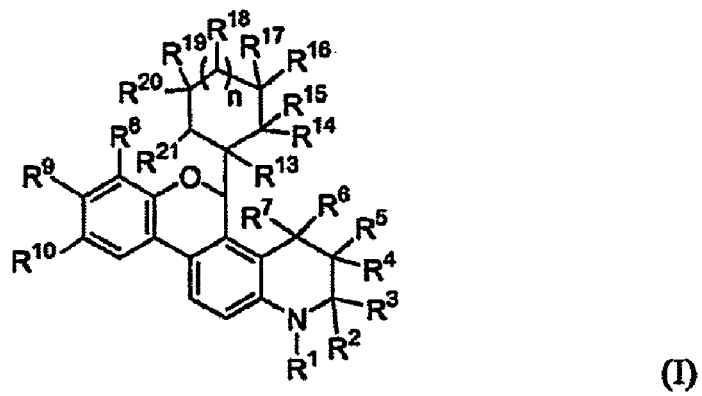

(I)

wherein:
$R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;
$R^2$ and $R^3$ each independently is selected from the group of hydrogen, $C_1$–$C_6$ alkyl, and $C_1$–$C_6$ haloalkyl; or
$R^2$ and $R^3$ taken together form a cycloalkyl ring of from three to twelve carbons;
$R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or
$R^5$ and $R^7$ taken together form a bond; or
$R^6$ and $R^7$ taken together are selected from the group of methylidene, mono-substituted methylidene, di-substituted methylidene and carbonyl;
$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;

UNITED STATES PATENT AND TRADEMARK OFFICE
CERTIFICATE OF CORRECTION

PATENT NO. : 7,071205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;
$R^{13}$ is hydrogen;
$R^{14}$, $R^{15}$, $R^{17}$, $R^{20}$ each independently is selected from the group of hydrogen, F, Cl, $C_1$–$C_4$ alkyl, and $C_1$–$C_4$ haloalkyl;
$R^{16}$ and $R^{18}$ taken together form a bond when n is 1;
$R^{16}$ and $R^{19}$ taken together form a bond when n is 0;
$R^{21}$ is hydrogen; and
n is 0, 1, 2, or 3;
or a pharmaceutically acceptable salt thereof.

Col. 42-45
15. A Compound selected from the group of:

(±)-(51,1'l)-5-(3-methyl-2-cyclohexenyl)-9-fluoro-1,2-dihydro-2,2,4-trimethyl-5H-chromeno[3,4-f]quinoline (compound 24);
(±)-(51,1'u)-5-(3-methyl-2-cyclohexenyl)-9-fluoro-1,2-dihydro-2,2,4-trimethyl-5H-chromeno[3,4-f]quinoline (compound 25);
(+)-(51,1'l)-5-(3-methyl-2-cyclohexenyl)-9-fluoro-1,2-dihydro-2,2,4-trimethyl-5H-chromeno[3,4-f]quinoline (compound 27);
(–)-(51,1'l)-5-(3-methyl-2-cyclohexenyl)-9-fluoro-1,2-dihydro-2,2,4-trimethyl-5H-chromeno[3,4-f]quinoline (compound 28);
(±)-(51,1'1)-5-(3-methyl-2-cyclohexenyl)-9-hydroxy-1,2-dihydro-2,2,4-trimethyl-5H-chromeno[3,4-f]quinoline (compound 29);

UNITED STATES PATENT AND TRADEMARK OFFICE
CERTIFICATE OF CORRECTION

PATENT NO.       : 7,071,205 B2
APPLICATION NO.  : 10/684229
DATED            : July 4, 2006
INVENTOR(S)      : Lin Zhi et al.

It is certified that error appears in the above-identified patent and that said Letters Patent is hereby corrected as shown below:

(±)-(51,1'u)-5-(3-methyl-2-cyclohexenyl)-9-hydroxy-1,2-dihydro-2,2,4-trimethy1-5H-chromeno[3,4-f]quinoline (compound 30);
(+)-(51,1'1)-5-(3-methyl-2-cyclohexenyl)-9-hydroxy-1,2-dihydro-2,2,4-trimethyl-5H-cbromeno[3,4-fjquinoline (compound 32);
(–)-(51,1'1)-5-(3-methyl-2-cyclohexenyl)-9-hydroxy-1,2-dihydro-2,2,4-trimethyl-5H-chromeno[3,4-fJquinoline (compound 33);
(±)-(51,1'1)-5-3-methy1-2-cyc1ohexeny1)-7,9-difluoro-1,2-dihydro-2,2,4-trimethyl-5H-chromeno[3,4-f]quinoline (compound 34);
(±)-(51,1'u)-5-(3-methyl-2-cyclohexenyl)-7,9-difluoro-1,2-dihydro-2,2,4-trimethyl-5H-chromeno[3,4-f]quinoline (compound 35);
(+)-(51,1'1)-5-(3-methyl-2-cyclohexenyl)-7,9-difluoro-1,2-dihydro-2,2,4-trimethyl-5H-chromeno[3,4-f]quinoline (compound 37);
(–)-(51,1'1)-5-(3-methyl-2-cyclohexenyl)-7,9-difluoro-1,2-dihydro-2,2,4-trimethyl-5H-chromeno[3,4-f]quinoline (compound 38);
(±)-(51,1'1)-5-(3-methyl-2-cyclohexenyl)-9-methoxy-1,2-dihydro-2,2,4-trimethyl-5H-chromeno[3,4-f]quinoline (compound 39);
(±)-(51,1'1)-5-(3-methyl-2-cyclohexenyl)-9-fluoro-1,2-dihydro-2,2-dimethyl-5H-chromeno[3,4-f]quinoline (compound 41);
(±)-(51,1'u)-5-(3-methyl-2-cyclohexenyl)-9-fluoro-1,2-dihydro-2,2-dimethyl-5H-chromeno[3,4-f]quinoline (compound 42);
(±)-(51,1'1)-5-(3-methy1-2-cyc1openteny1)-9-fluoro-1,2-dihydro-2,2,4-trimethyl-5H-chromeno[3,4-f]quinoline (compound 44);
(±)-(51,1'u)-5-(3-methyl-2-cyclopentenyl)-9-fluoro-1,2-dihydro-2,2,4-trimethy-5H-chromeno[3,4-f]quinoline (compound 45);

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

- (±)-(51,1'1)-5-(3,5,5-trimethyl-2-cyclohexenyl)-9-fluoro-1,2-dihydro-2,2,4-trimethyl-5H-chromeno[3,4-f]quinoline (compound 47);
- (±)-(51,1'u)-5-(3,5,5-trimethyl-2-cyclohexenyl)-9-fluoro-1,2-dihydro-2,2,4-trimethyl-5H-chromeno[3,4-f]quinoline (compound 48);
- (±)-(51,1'1)-5-(3-methyl-2-cyclopentenyl)-7,9-difluoro-1,2-dihydro-2,2,4-trimethyl-5H-chromeno[3,4-f]quinoline (compound 50);
- (±)-(51,1'u)-5-(3-methyl-2-cyclopentenyl)-7,9-difluoro-1,2-dihydro-2,2,4-trimethyl-5H-chromeno[3,4-f]quinoline (compound 51);
- (±)-5-(3-methyl-3-cyclopentenyl)-7,9-difluoro-1,2-dihydro-2,2,4-trimethyl-5H-chromeno[3,4-f]quinoline (compound 52);
- (±)-5-(2-cyclopenta-1,3-dienyl)-9-fluoro-1,2-dihydro-2,2,4-trimethyl-5H-chromeno[3,4-f]quinoline (compound 53);
- (±)-(51,1'1)-5-(3-ethyl-2-cyclohexenyl)-9-fluoro-1,2-dihydro-2,2,4-trimethyl-5H-chromeno[3,4-f]quinoline (compound 55);
- (±)-(51,1'u)-5-(3-ethyl-2-cyclohexenyl)-9-fluoro-1,2-dihydro-2,2,4-trimethyl-5H-chromeno[3,4-f]quinoline (compound 56);
- (±)-(51,1'1)-5-(3-methyl-2-cyclohexenyl)-7-fluoro-1,2-dihydro-2,2,4-trimethyl-5H-chromeno[3,4-f]quinoline (compound 58);
- (±)-(51,1'u)-5-(3-methyl-2-cyclohexenyl)-7-fluoro-1,2-dihydro-2,2,4-trimethyl-5H-chromeno[3,4-f]quinoline (compound 59);
- (±)-(51,1'1)-5-(3-ethyl-2-cyclohexenyl)-7,9-difluoro-1,2-dihydro-2,2,4-trimethyl-5H-chromeno[3,4-f]quinoline (compound 61);
- (±)-(51,1'1)-5-(3-ethylidenecyclohexyl)-7,9-difluoro-1,2-dihydro-2,2,4-trimethyl-5H-chromeno[3,4-f]quinoline (compound 62);

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

(±)-(5l,1'l)-5-(3-methyl-3-cyclohexenyl)-7,9-difluoro-1,2-dihydro-2,2,4-trimethyl-5H-chromeno[3,4-f]quinoline (compound 63);

(±)-(5l,1'l)-5-(3-methyl-2-cyclobexenyl)-9-fluoro-1,2-dihydro-8-methoxy-2,2,4-trimethyl-5H-chromeno[3,4-f]quinoline (compound 64);

(±)-(5l,1'u)-5-(3-methyl-2-cyclohexenyl)-9-fluoro-1,2-dihydro-8-methoxy-2,2,4-trimethyl-5H-chromeno[3,4-f]quinoline (compound 65);

(±)-(5l,1'1)-5-(2-cyclopentenyl)-7,9-difluoro-1,2-dihydro-2,2,4-trimethyl-5H-chromeno[3,4-f]quinoline (compound 67);

(±)-(5l,1'u)-5-(2-cyclopentenyl)-7,9-difluoro-1,2-dihydro-2,2,4-trimethyl-5H-chromeno[3,4-f]quinoline (compound 68);

(±)-5-(1-cyclopentenyl)-7,9-difluoro-1,2-dihydro-2,2,4-trimethy1-5H-chromeno[3,4-f]quinoline (compound 69);

(±)-(5l,1'1)-5-(2,3-dimethyl-2-cyclopentenyl)-7,9-difluoro-1,2-dihydro-2,2,4-trimethyl-5H-chromeno[3,4-f]quinoline (compound 71);

(+)-(5l,1'1)-5-(2,3-dimethyl-2-eyclopentenyl)-7,9-difluoro-1,2-dihydro-2,2,4-trimethyl-5H-chromeno[3,4-f]quinoline (compound 73);

(−)-(5l,1'1)-5-(2,3-dimethyl-2-cyclopentenyl)-7,9-difluoro-1,2-dihydro-2,2,4-trimethyl-5H-chromeno[3,4-f]quinoline (compound 74);

(±)-(5l,1'1)-5-(2-cyclohexenyl)-7,9-difluoro-1,2-dihydro-2,2,4-trimethyl-5H-chromeno[3,4-f]quinoline (compound 75);

(±)-(5l,1'u)-5-(2-cyclohexenyl)-7,9-difluoro-1,2-dihydro-2,2,4-trimethyl-5H-chromeno[3,4-f]quinoline (compound 76);

(±)-(5l,1'1)-5-(2-cyclohexenyl)-7,9-difluoro-1,2,3,4-tetrahydro-2,2-dimethyl-4-methylidene-5H-chromeno[3,4-f]quinoline (compound 77);

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

- (±)-(51,1'l)-5-(2-methylidenecyclohexyl)-9-fluoro-1,2-dihydro-2,2,4-trimethyl-5H-chromeno[3,4-f]quinoline (compound 79);
- (±)-(51,1'u)-5-(2-methylidenecyclohexyl)-9-fluoro-1,2-dihydro-2,2,4-trimethyl-5H-chromeno[3,4-f]quinoline (compound 80);
- (±)-(51,1'1)-5-(2-oxocyclohexyl)-9-fluoro-1,2-dihydro-2,2,4-trimethyl-5H-chromeno[3,4-f]quinoline (compound 81);
- (±)-(51,1'u)-5-(2-oxocyclohexyl)-9-fluoro-1,2-dihydro-2,2,4-trimethyl-5H-chromeno[3,4-f]quinoline (compound 82);
- (±)-(51,1'1)-5-(3-methyl-2-cyclohexenyl)-9-methoxy-1,2-dihydro-1,2,2,4-tetramethyl-5H-chromeno[3,4-f]quinoline (compound 83);
- (±)-5-(2-cyclohexenyl)-9-fluoro-1,2-dihydro-2,2,4-trimethyl-5H-chromeno[3,4-f]-quinoline (compound 84);
- (±)-(51,1'l)-5-(2,3-dimethyl-2-cyclohexenyl)-7,9-difluoro-1,2-dihydro-2,2,4-trimethyl-5H-chromeno[3,4-f]quinoline (compound 85);
- (±)-5-(3-methylidene-cyclohexyl)-7,9-difluoro-1,2-dihydro-2,2,4-trimethyl-5H-chromeno[3,4-f]quinoline (compound 87);
- (±)-(51,1'u)-5-(3-ethylidenecyclohexyl)-7,9-difluoro-1,2-dihydro-2,2,4-trimethyl-5H-chromeno[3,4-f]quinoline (compound 88);
- (±)-(51,1'l)-5-(2-cycloheptenyl)-7,9-difluoro-1,2-dihydro-2,2,4-trimethyl-5H-chromeno[3,4-f]quinoline (Compound 89);
- (±)-(51,1'1)-5-(2-cyclooctenyl)-7,9-difluoro-1,2-dihydro-2,2,4-trimethyl-5H-chromeno[3,4-f]quinoline (Compound 91);
- (±)-(51,1'u)-5-(2-cyclooctenyl)-7,9-difluoro-1,2-dihydro-2,2,4-trimethyl-5H-chromeno[3,4-f]quinoline (Compound 92);

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

(±)-(51,1'1)-5-(2,3-epoxy-3-methylcyclohexyl)-7,9-difluoro-1,2-dihydro-2,2,4-trimethyl-5H-chromeno[3,4-f]quinoline (Compound 94);

(±)-(51,1'1)-5-(3-methyl-2-cyclohexenyl)-7,9-difluoro-1,2,3,4-tetrahydro-2,2-dimethyl-4-methylene-5H-chromeno[3,4-f]quinolin-3-ol (Compound 95);

(±)-(51,1'1)-5-(2,3-epoxy-2,3-dimethylcyclopentyl)-7,9-difluoro-1,2-dihydro-2,2,4-trimethyl-5H-chromeno[3,4-f]quinoline (Compound 96);

(±)-(51,1'u)-5-(2,3-epoxy-3-methylcyclohexyl)-7,9-difluoro-1,2-dihydro-2,2,4-trimethyl-5H-chromeno[3,4-f]quinoline (Compound 97); and (±)-(51,1'1)-5-(3-methyl-2-cyclohexenyl)-7,9-difluoro-1,2,3,4-tetrahydro-2,2-dimethyl-5H-chromeno[3,4-f]quinolin-4-one (Compound 98).

This certificate supersedes Certificate of Correction issued November 28, 2006.

Signed and Sealed this

Third Day of April, 2007

JON W. DUDAS
*Director of the United States Patent and Trademark Office*

UNITED STATES PATENT AND TRADEMARK OFFICE
CERTIFICATE OF CORRECTION

PATENT NO.      : 7,071,205 B2
APPLICATION NO. : 10/684229
DATED           : July 4, 2006
INVENTOR(S)     : Lin Zhi et al.

It is certified that error appears in the above-identified patent and that said Letters Patent is hereby corrected as shown below:

IN THE TITLE PAGES:

In Item [56] References Cited, in U.S. PATENT DOCUMENTS:
please add the following reference: --6,001,846 A   12/1999   Edwards et al.   514/285--
in 6,566,358 please replace "Zhi et al." with --Zhang et a1.--
in 6,566,372 please replace "West et al." with --Zhi et al.--

In Item [56] References Cited, in OTHER PUBLICATIONS:
in Hamann et al., please replace "dihyrdo" with --dihydro--

At column 8, Table A, row $R^1$, please replace "$C_1$-C haloalkyl" with --$C_1$-$C_4$ haloalkyl--
at column 9, Table A, row $R^9$, please replace "$CONR^H R^{12}$" with --$CONR^{11}R^{12}$--
at column 11, Table A, below row $R^{16}$, please replace "$R^{15}$" with --$R^{16}$--

Please replace Claims 12, 13, 14, and 15 with the following Claims:

Col. 40
12. A compound of the formula:

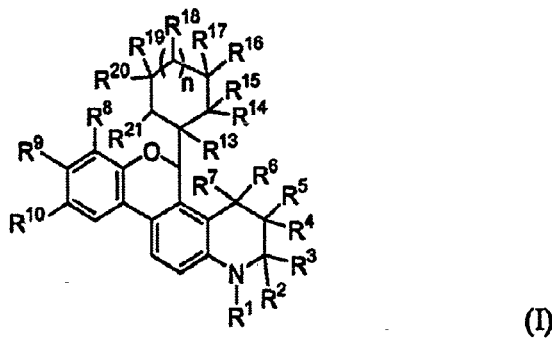

(I)

wherein:
  $R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;
  $R^2$ and $R^3$ each independently is selected from the group of hydrogen, $C_1$–$C_6$ alkyl, and $C_1$–$C_6$ haloalkyl; or
  $R^2$ and $R^3$ taken together form a cycloalkyl ring of from three to twelve carbons;
  $R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or
  $R^5$ and $R^7$ taken together form a bond; or
  $R^6$ and $R^7$ taken together are selected from the group of methylidene, mono-substituted methylidene, di-substituted methylidene and carbonyl;

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;

$R^{13}$ is hydrogen;

$R^{14}$ and $R^{16}$ taken together form a bond or "–O–" bridge;

$R^{15}$, $R^{17}$, $R^{18}$, $R^{19}$, $R^{20}$ each independently is selected from the group of hydrogen, F, Cl, $C_1$–$C_4$ alkyl, and $C_1$–$C_4$ haloalkyl;

$R^{21}$ is hydrogen; and n is 0, 1, 2, or 3;

or a pharmaceutically acceptable salt thereof.

Col. 41
13. A compound of the formula:

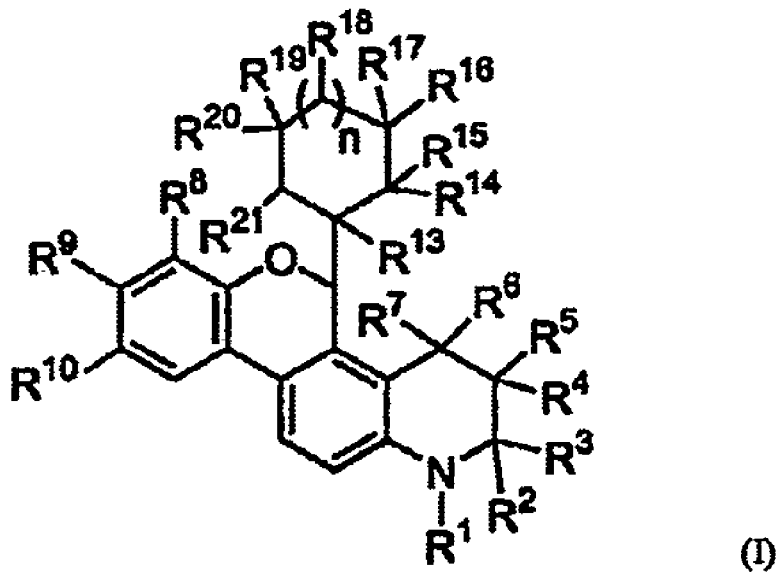

(I)

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

wherein:
$R^1$ is selected from the group of hydrogen, $C_1$–$C_4$ alkyl, $C_1$–$C_4$ haloalkyl, $C_1$–$C_4$ heteroalkyl, $COR^{11}$, $CO_2R^{11}$, $SO_2R^{11}$, and $CONR^{11}R^{12}$;
$R^2$ and $R^3$ each independently is selected from the group of hydrogen, $C_1$–$C_6$ alkyl, and $C_1$–$C_6$ haloalkyl; or
$R^2$ and $R^3$ taken together form a cycloalkyl ring of from three to twelve carbons;
$R^4$ through $R^7$ each independently is selected from the group of hydrogen, F, Cl, Br, CN, $OR^{11}$, $C_1$–$C_4$ alkyl, $C_1$–$C_4$ haloalkyl, and $C_1$–$C_4$ heteroalkyl; or
$R^5$ and $R^7$ taken together form a bond; or
$R^6$ and $R^7$ taken together are selected from the group of methylidene, mono-substituted methylidene, di-substituted methylidene and carbonyl;
$R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1$–$C_8$ alkyl, $C_1$–$C_8$ heteroalkyl, $C_1$–$C_8$ haloalkyl, allyl, $C_2$–$C_8$ alkenyl and $C_2$–$C_8$ alkynyl;
$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;
$R^{13}$ is hydrogen;
$R^{14}$, $R^{15}$, $R^{18}$, $R^{19}$, $R^{20}$ each independently is selected from the group of hydrogen, F, Cl, $C_1$–$C_4$ alkyl, and $C_1$–$C_4$ haloalkyl;
$R^{16}$ and $R^{17}$ taken together are selected from the group of methylidene, mono-substituted methylidene, and di-substituted methylidene;
$R^{21}$ is hydrogen; or
$R^{21}$ and $R^{20}$ taken together form a bond;
n is 0, 1, 2, or 3;
or a pharmaceutically acceptable salt thereof.

UNITED STATES PATENT AND TRADEMARK OFFICE
CERTIFICATE OF CORRECTION

PATENT NO.       : 7,071,205 B2
APPLICATION NO.  : 10/684229
DATED            : July 4, 2006
INVENTOR(S)      : Lin Zhi et al.

It is certified that error appears in the above-identified patent and that said Letters Patent is hereby corrected as shown below:

Col. 42
14. A compound of the formula:

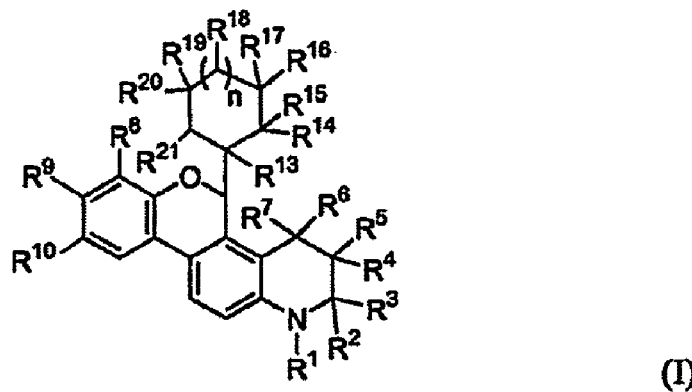

(I)

wherein:
  $R^1$ is selected from the group of hydrogen, $C_1-C_4$ alkyl, $C_1-C_4$ haloalkyl, $C_1-C_4$ heteroalkyl, $COR^{11}$, $CO_2R^{11}$, $SO_2R^{11}$, and $CONR^{11}R^{12}$;
  $R^2$ and $R^3$ each independently is selected from the group of hydrogen, $C_1-C_6$ alkyl, and $C_1-C_6$ haloalkyl; or
  $R^2$ and $R^3$ taken together form a cycloalkyl ring of from three to twelve carbons;
  $R^4$ through $R^7$ each independently is selected from the group of hydrogen, F, Cl, Br, CN, $OR^{11}$, $C_1-C_4$ alkyl, $C_1-C_4$ haloalkyl, and $C_1-C_4$ heteroalkyl; or
  $R^5$ and $R^7$ taken together form a bond; or
  $R^6$ and $R^7$ taken together are selected from the group of methylidene, mono-substituted methylidene, di-substituted methylidene and carbonyl;
  $R^8$ through $R^{10}$ each independently is selected from the group of hydrogen, F, Cl, Br, I, $NO_2$, CN, $OR^{11}$, $NR^{11}R^{12}$, $SR^{11}$, $COR^{11}$, $CO_2R^{11}$, $CONR^{11}R^{12}$, $C_1-C_8$ alkyl, $C_1-C_8$ heteroalkyl, $C_1-C_8$ haloalkyl, allyl, $C_2-C_8$ alkenyl and $C_2-C_8$ alkynyl;

UNITED STATES PATENT AND TRADEMARK OFFICE
CERTIFICATE OF CORRECTION

| | | |
|---|---|---|
| PATENT NO. | : 7,071205 B2 | |
| APPLICATION NO. | : 10/684229 | |
| DATED | : July 4, 2006 | |
| INVENTOR(S) | : Lin Zhi et al. | |

It is certified that error appears in the above-identified patent and that said Letters Patent is hereby corrected as shown below:

$R^{11}$ and $R^{12}$ each is independently selected from the group of hydrogen, $C_1$–$C_4$ alkyl, $C_1$–$C_4$ heteroalkyl, and $C_1$–$C_4$ haloalkyl;
$R^{13}$ is hydrogen;
$R^{14}$, $R^{15}$, $R^{17}$, $R^{20}$ each independently is selected from the group of hydrogen, F, Cl, $C_1$–$C_4$ alkyl, and $C_1$–$C_4$ haloalkyl;
$R^{16}$ and $R^{18}$ taken together form a bond when n is 1;
$R^{16}$ and $R^{19}$ taken together form a bond when n is 0;
$R^{21}$ is hydrogen; and
n is 0, 1, 2, or 3;
or a pharmaceutically acceptable salt thereof.

Col. 42-45
15. A Compound selected from the group of:

(±)-(51,1'l)-5-(3-methyl-2-cyclohexenyl)-9-fluoro-1,2-dihydro-2,2,4-trimethyl-5H-chromeno[3,4-f]quinoline (compound 24);
(±)-(51,1'u)-5-(3-methyl-2-cyclohexenyl)-9-fluoro-1,2-dihydro-2,2,4-trimethyl-5H-chromeno[3,4-f]quinoline (compound 25);
(+)-(51,1'l)-5-(3-methyl-2-cyclohexenyl)-9-fluoro-1,2-dihydro-2,2,4-trimethyl-5H-chromeno[3,4-f]quinoline (compound 27);
(−)-(51,1'l)-5-(3-methyl-2-cyclohexenyl)-9-fluoro-1,2-dihydro-2,2,4-trimethyl-5H-chromeno[3,4-f]quinoline (compound 28);
(±)-(51,1'1)-5-(3-methyl-2-cyclohexenyl)-9-hydroxy-1,2-dihydro-2,2,4-trimethyl-5H-chromeno[3,4-f]quinoline (compound 29);

UNITED STATES PATENT AND TRADEMARK OFFICE
CERTIFICATE OF CORRECTION

PATENT NO.        : 7,071,205 B2
APPLICATION NO. : 10/684229
DATED             : July 4, 2006
INVENTOR(S)      : Lin Zhi et al.

It is certified that error appears in the above-identified patent and that said Letters Patent is hereby corrected as shown below:

(±)-(51,1'u)-5-(3-methyl-2-cyclohexenyl)-9-hydroxy-1,2-dihydro-2,2,4-trimethyl-5H-chromeno[3,4-f]quinoline (compound 30);

(+)-(51,1'1)-5-(3-methyl-2-cyclohexenyl)-9-hydroxy-1,2-dihydro-2,2,4-trimethyl-5H-cbromeno[3,4-fjquinoline (compound 32);

(−)-(51,1'1)-5-(3-methyl-2-cyclohexenyl)-9-hydroxy-1,2-dihydro-2,2,4-trimethyl-5H-chromeno[3,4-fJquinoline (compound 33);

(±)-(51,1'1)-5-3-methyl-2-cyclohexenyl)-7,9-difluoro-1,2-dihydro-2,2,4-trimethyl-5H-chromeno[3,4-f]quinoline (compound 34);

(±)-(51,1'u)-5-(3-methyl-2-cyclohexenyl)-7,9-difluoro-1,2-dihydro-2,2,4-trimethyl-5H-chromeno[3,4-f]quinoline (compound 35);

(+)-(51,1'1)-5-(3-methyl-2-cyclohexenyl)-7,9-difluoro-1,2-dihydro-2,2,4-trimethyl-5H-chromeno[3,4-f]quinoline (compound 37);

(−)-(51,1'1)-5-(3-methyl-2-cyclohexenyl)-7,9-difluoro-1,2-dihydro-2,2,4-trimethyl-5H-chromeno[3,4-f]quinoline (compound 38);

(±)-(51,1'1)-5-(3-methyl-2-cyclohexenyl)-9-methoxy-1,2-dihydro-2,2,4-trimethyl-5H-chromeno[3,4-f]quinoline (compound 39);

(±)-(51,1'1)-5-(3-methyl-2-cyclohexenyl)-9-fluoro-1,2-dihydro-2,2-dimethyl-5H-chromeno[3,4-f]quinoline (compound 41);

(±)-(51,1'u)-5-(3-methyl-2-cyclohexenyl)-9-fluoro-1,2-dihydro-2,2-dimethyl-5H-chromeno[3,4-f]quinoline (compound 42);

(±)-(51,1'1)-5-(3-methyl-2-cyclopentenyl)-9-fluoro-1,2-dihydro-2,2,4-trimethyl-5H-chromeno[3,4-f]quinoline (compound 44);

(±)-(51,1'u)-5-(3-methyl-2-cyclopentenyl)-9-fluoro-1,2-dihydro-2,2,4-trimethy-5H-chromeno[3,4-f]quinoline (compound 45);

UNITED STATES PATENT AND TRADEMARK OFFICE
CERTIFICATE OF CORRECTION

PATENT NO.       : 7,071,205 B2
APPLICATION NO.  : 10/684229
DATED            : July 4, 2006
INVENTOR(S)      : Lin Zhi et al.

It is certified that error appears in the above-identified patent and that said Letters Patent is hereby corrected as shown below:

- (±)-(51,1'1)-5-(3,5,5-trimethyl-2-cyclohexenyl)-9-fluoro-1,2-dihydro-2,2,4-trimethyl-5H-chromeno[3,4-f]quinoline (compound 47);
- (±)-(51,1'u)-5-(3,5,5-trimethyl-2-cyclohexenyl)-9-fluoro-1,2-dihydro-2,2,4-trimethyl-5H-chromeno[3,4-f]quinoline (compound 48);
- (±)-(51,1'1)-5-(3-methyl-2-cyclopentenyl)-7,9-difluoro-1,2-dihydro-2,2,4-trimethyl-5H-chromeno[3,4-f]quinoline (compound 50);
- (±)-(51,1'u)-5-(3-methyl-2-cyclopentenyl)-7,9-difluoro-1,2-dihydro-2,2,4-trimethyl-5H-chromeno[3,4-f]quinoline (compound 51);
- (±)-5-(3-methyl-3-cyclopentenyl)-7,9-difluoro-1,2-dihydro-2,2,4-trimethyl-5H-chromeno[3,4-f]quinoline (compound 52);
- (±)-5-(2-cyclopenta-1,3-dienyl)-9-fluoro-1,2-dihydro-2,2,4-trimethyl-5H-chromeno[3,4-f]quinoline (compound 53);
- (±)-(51,1'1)-5-(3-ethyl-2-cyclohexenyl)-9-fluoro-1,2-dihydro-2,2,4-trimethyl-5H-chromeno[3,4-f]quinoline (compound 55);
- (±)-(51,1'u)-5-(3-ethyl-2-cyclohexenyl)-9-fluoro-1,2-dihydro-2,2,4-trimethyl-5H-chromeno[3,4-f]quinoline (compound 56);
- (±)-(51,1'1)-5-(3-methyl-2-cyclohexenyl)-7-fluoro-1,2-dihydro-2,2,4-trimethyl-5H-chromeno[3,4-f]quinoline (compound 58);
- (±)-(51,1'u)-5-(3-methyl-2-cyclohexenyl)-7-fluoro-1,2-dihydro-2,2,4-trimethyl-5H-chromeno[3,4-f]quinoline (compound 59);
- (±)-(51,1'1)-5-(3-ethyl-2-cyclohexenyl)-7,9-difluoro-1,2-dihydro-2,2,4-trimethyl-5H-chromeno[3,4-f]quinoline (compound 61);
- (±)-(51,1'1)-5-(3-ethylidenecyclohexyl)-7,9-difluoro-1,2-dihydro-2,2,4-trimethyl-5H-chromeno[3,4-f]quinoline (compound 62);

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

(±)-(51,1'l)-5-(3-methyl-3-cyclohexenyl)-7,9-difluoro-1,2-dihydro-2,2,4-trimethyl-5H-chromeno[3,4-f]quinoline (compound 63);

(±)-(51,1'l)-5-(3-methyl-2-cyclobexenyl)-9-fluoro-1,2-dihydro-8-methoxy-2,2,4-trimethyl-5H-chromeno[3,4-f]quinoline (compound 64);

(±)-(51,1'u)-5-(3-methyl-2-cyclohexenyl)-9-fluoro-1,2-dihydro-8-methoxy-2,2,4-trimethyl-5H-chromeno[3,4-f]quinoline (compound 65);

(±)-(51,1'1)-5-(2-cyclopentenyl)-7,9-difluoro-1,2-dihydro-2,2,4-trimethyl-5H-chromeno[3,4-f]quinoline (compound 67);

(±)-(51,1'u)-5-(2-cyclopentenyl)-7,9-difluoro-1,2-dihydro-2,2,4-trimethyl-5H-chromeno[3,4-f]quinoline (compound 68);

(±)-5-(1-cyclopentenyl)-7,9-difluoro-1,2-dihydro-2,2,4-trimethy1-5H-chromeno[3,4-f]quinoline (compound 69);

(±)-(51,1'1)-5-(2,3-dimethyl-2-cyclopentenyl)-7,9-difluoro-1,2-dihydro-2,2,4-trimethyl-5H-chromeno[3,4-f]quinoline (compound 71);

(+)-(51,1'1)-5-(2,3-dimethyl-2-cyclopentenyl)-7,9-difluoro-1,2-dihydro-2,2,4-trimethyl-5H-chromeno[3,4-f]quinoline (compound 73);

(−)-(51,1'1)-5-(2,3-dimethyl-2-cyclopentenyl)-7,9-difluoro-1,2-dihydro-2,2,4-trimethyl-5H-chromeno[3,4-f]quinoline (compound 74);

(±)-(51,1'1)-5-(2-cyclohexenyl)-7,9-difluoro-1,2-dihydro-2,2,4-trimethyl-5H-chromeno[3,4-f]quinoline (compound 75);

(±)-(51,1'u)-5-(2-cyclohexenyl)-7,9-difluoro-1,2-dihydro-2,2,4-trimethyl-5H-chromeno[3,4-f]quinoline (compound 76);

(±)-(51,1'1)-5-(2-cyclohexenyl)-7,9-difluoro-1,2,3,4-tetrahydro-2,2-dimethyl-4-methylidene-5H-chromeno[3,4-f]quinoline (compound 77);

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

(±)-(51,1'l)-5-(2-methylidenecyclohexyl)-9-fluoro-1,2-dihydro-2,2,4-trimethyl-5H-chromeno[3,4-f]quinoline (compound 79);

(±)-(51,1'u)-5-(2-methylidenecyclohexyl)-9-fluoro-1,2-dihydro-2,2,4-trimethyl-5H-chromeno[3,4-f]quinoline (compound 80);

(±)-(51,1'1)-5-(2-oxocyclohexyl)-9-fluoro-1,2-dihydro-2,2,4-trimethyl-5H-chromeno[3,4-f]quinoline (compound 81);

(±)-(51,1'u)-5-(2-oxocyclohexyl)-9-fluoro-1,2-dihydro-2,2,4-trimethyl-5H-chromeno[3,4-f]quinoline (compound 82);

(±)-(51,1'1)-5-(3-methyl-2-cyclohexenyl)-9-methoxy-1,2-dihydro-1,2,2,4-tetramethyl-5H-chromeno[3,4-f]quinoline (compound 83);

(±)-5-(2-cyclohexenyl)-9-fluoro-1,2-dihydro-2,2,4-trimethyl-5H-chromeno[3,4-f]-quinoline (compound 84);

(±)-(51,1'l)-5-(2,3-dimethyl-2-cyclohexenyl)-7,9-difluoro-1,2-dihydro-2,2,4-trimethyl-5H-chromeno[3,4-f]quinoline (compound 85);

(±)-5-(3-methylidene-cyclohexyl)-7,9-difluoro-1,2-dihydro-2,2,4-trimethyl-5H-chromeno[3,4-f]quinoline (compound 87);

(±)-(51,1'u)-5-(3-ethylidenecyclohexyl)-7,9-difluoro-1,2-dihydro-2,2,4-trimethyl-5H-chromeno[3,4-f]quinoline (compound 88);

(±)-(51,1'l)-5-(2-cycloheptenyl)-7,9-difluoro-1,2-dihydro-2,2,4-trimethyl-5H-chromeno[3,4-f]quinoline (Compound 89);

(±)-(51,1'1)-5-(2-cyclooctenyl)-7,9-difluoro-1,2-dihydro-2,2,4-trimethyl-5H-chromeno[3,4-f]quinoline (Compound 91);

(±)-(51,1'u)-5-(2-cyclooctenyl)-7,9-difluoro-1,2-dihydro-2,2,4-trimethyl-5H-chromeno[3,4-f]quinoline (Compound 92);

UNITED STATES PATENT AND TRADEMARK OFFICE
CERTIFICATE OF CORRECTION

PATENT NO. : 7,071,205 B2
APPLICATION NO. : 10/684229
DATED : July 4, 2006
INVENTOR(S) : Lin Zhi et al.

It is certified that error appears in the above-identified patent and that said Letters Patent is hereby corrected as shown below:

(±)-(51,1'1)-5-(2,3-epoxy-3-methylcyclohexyl)-7,9-difluoro-1,2-dihydro-2,2,4-trimethyl-5H-chromeno[3,4-f]quinoline (Compound 94);
(±)-(51,1'1)-5-(3-methyl-2-cyclohexenyl)-7,9-difluoro-1,2,3,4-tetrahydro-2,2-dimethyl-4-methylene-5H-chromeno[3,4-f]quinolin-3-ol (Compound 95);
(±)-(51,1'1)-5-(2,3-epoxy-2,3-dimethylcyclopentyl)-7,9-difluoro-1,2-dihydro-2,2,4-trimethyl-5H-chromeno[3,4-f]quinoline (Compound 96);
(±)-(51,1'u)-5-(2,3-epoxy-3-methylcyclohexyl)-7,9-difluoro-1,2-dihydro-2,2,4-trimethyl-5H-chromeno[3,4-f]quinoline (Compound 97); and
(±)-(51,1'1)-5-(3-methyl-2-cyclohexenyl)-7,9-difluoro-1,2,3,4-tetrahydro-2,2-dimethyl-5H-chromeno[3,4-f]quinolin-4-one (Compound 98).

This certificate supersedes Certificates of Correction issued November 28, 2006 and April 3, 2007.

Signed and Sealed this

Twenty-fourth Day of July, 2007

JON W. DUDAS
*Director of the United States Patent and Trademark Office*